US008735567B2

(12) United States Patent
Lu et al.

(10) Patent No.: US 8,735,567 B2
(45) Date of Patent: May 27, 2014

(54) MULTI-TARGETED RNAI THERAPEUTICS FOR SCARLESS WOUND HEALING OF SKIN

(76) Inventors: Patrick Y. Lu, Rockville, MD (US); Ling Li, Port St. Lucie, FL (US); Vera Simonenko, Germantown, MD (US)

( * ) Notice: Subject to any disclaimer, the term of this patent is extended or adjusted under 35 U.S.C. 154(b) by 249 days.

(21) Appl. No.: 12/741,645

(22) PCT Filed: Nov. 6, 2008

(86) PCT No.: PCT/US2008/012498
§ 371 (c)(1),
(2), (4) Date: Aug. 26, 2010

(87) PCT Pub. No.: WO2009/061417
PCT Pub. Date: May 14, 2009

(65) Prior Publication Data
US 2010/0319074 A1    Dec. 16, 2010

Related U.S. Application Data

(60) Provisional application No. 60/985,820, filed on Nov. 6, 2007.

(51) Int. Cl.
*C07H 21/04* (2006.01)
*C07H 21/02* (2006.01)
*A61K 48/00* (2006.01)

(52) U.S. Cl.
USPC ........................... 536/24.5; 536/23.1; 514/44

(58) Field of Classification Search
None
See application file for complete search history.

(56) References Cited

U.S. PATENT DOCUMENTS

| 2005/0176024 | A1 | 8/2005 | McSwiggen et al. |
| 2006/0121514 | A1 | 6/2006 | Young et al. |
| 2006/0134787 | A1 | 6/2006 | Zamore et al. |
| 2006/0265765 | A1 | 11/2006 | Agatsuma et al. |
| 2007/0003519 | A1 | 1/2007 | Lu et al. |
| 2008/0241198 | A1 | 10/2008 | Liu et al. |
| 2008/0279920 | A1 | 11/2008 | Tang et al. |
| 2011/0165227 | A1 | 7/2011 | Yan et al. |
| 2012/0071540 | A1 | 3/2012 | Lu et al. |

FOREIGN PATENT DOCUMENTS

| WO | WO 0147496 A1 | 7/2001 |
| WO | WO 03040399 A2 | 5/2003 |
| WO | WO 03070918 A2 | 8/2003 |
| WO | WO 03090719 A1 | 11/2003 |
| WO | WO 2005076999 A2 | 8/2005 |
| WO | WO 2007079224 A2 | 7/2007 |

OTHER PUBLICATIONS

Kim et al. (Biochemical and Biophysical Research Communications 343 (2006) 1072-1078).*

International Search Report and Written Opinion of the International Searching Authority on International App. No. PCT/US2008/12498 (WO 2009/061417) of Sirnaomics, Inc., Feb. 23, 2009.
European Patent Office Search Report and Opinion for App. No. 08846548.9-2107 of Sirnaomics, Inc., Sep. 26, 2011.
Barik, Sailen, "Control of nonsegmented negative-strand RNA virus replication by siRNA," Virus Research, vol. 102, 2004, pp. 27-35.
Bitko, Vira, et al., "Phenotypic silencing of cytoplasmic genes using sequence-specific double-stranded short interfering RNA and its application in the reverse genetics of wild type negative-strand RNA viruses," BMC Microbiology, vol. 1, No. 34, Dec. 20, 2001, pp. 1-11.
Cheema, Sangeeta, et al., "Regulation and Guidance of Cell Behavior for Tissue Regeneration Via the Sirna Mechanism", Wound Repair and Regeneration, vol. 15, No. 3, 2007, pp. 286-295.
Choi, Byung-Min, et al., "Control of Scarring in Adult Wounds Using Antisense Transforming Growth Factor-Beta1 Oligodeoxynucleotides", Immunology and Cell Biology, vol. 74, 1996, pp. 144-150.
De Wolf, Holger, et al., "Effect of Cationic Carriers on the Pharmacokinetics and Tumor Localization of Nucleic Acids after Intravenous Administration," International Journal of Pharmaceutics, 331, 2007, pp. 167-175.
Leng, Qixin, et al., "Highly Branched HK Peptides Are Effective Carriers of siRNA," The Journal of Gene Medicine, 2005, 7, pp. 977-986.
Mack, Judith, et al., "Hoxb13 Knockout Adult Skin Exhibits High Levels of Hyaluronan and Enhanced Wound Healing", FASEB Journal, vol. 17, Jul. 2003, pp. 1352-1354.
Michels, Stephan, et al., "Promising New Treatments for Neovascular Age-Related Macular Degeneration," Expert Opin. Investig. Drugs, 2006, 15(7), pp. 779-793.
Pickering, Lulu, "Progress in RNA-based therapeutics," Spectrum Drug Discovery and Design, Decision Resources, Inc., Waltham, Massachusetts, Aug. 4, 2005, pp. 6-1 to 6-20.
Stelnicki, Eric, et al., "Modulation of the Human Homeobox Genes PRX-2 and HOXB13 in Scarless Fetal Wounds", Journal of Investigative Dermatology, vol. 111, 1998, pp. 57-63.
Whitmore, Mark, et al., "Synergistic Activation of Innate Immunity by Double-Stranded RNA and CpG DNA Promotes Enhanced Antitumor Activity," Cancer Research 64, 5850-5860, Aug. 15, 2004.
Wilgus, Traci, et al, "Reduction of Scar Formation in Full-Thickness Wounds With Topical Celecoxib Treatment", Wound Repair and Regeneration, Mosby-Year Book, St. Louis, Mo, US, vol. 11, 2003, pp. 25-34.

* cited by examiner

*Primary Examiner* — Amy Bowman
(74) *Attorney, Agent, or Firm* — Geoffrey M. Karny

(57) ABSTRACT

The present invention provides small interfering RNA (siRNA) molecules, compositions containing them, and methods of using them for improvement of skin scarless wound healing and other skin conditions, such as psoriasis and lupus-caused cutaneous lesions. The invention includes siRNA molecules and compositions containing them that inhibit the expression of one or more genes that promote pathological or undesired processes in wound healing and methods of using them.

12 Claims, 24 Drawing Sheets

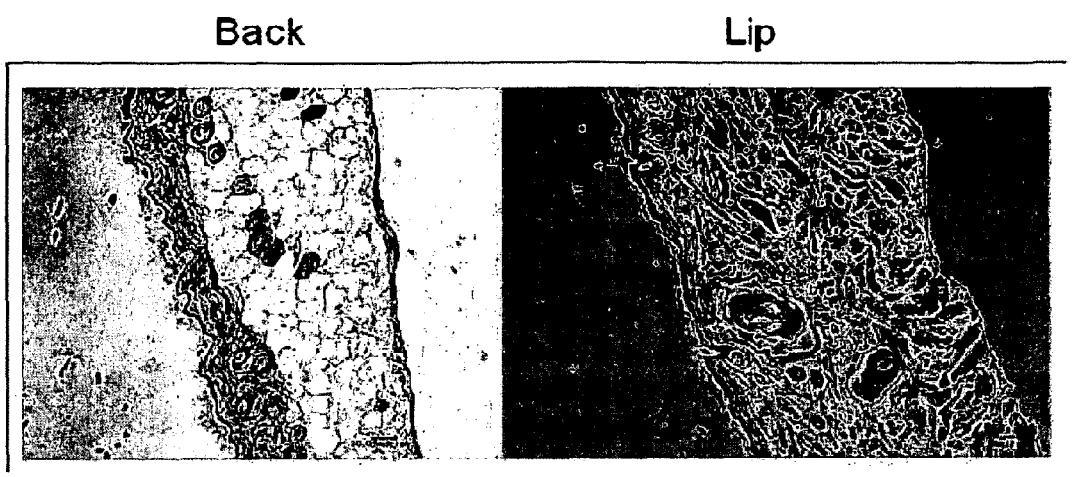
Figure 1. Hematoxylin and Eosin (H&E) staining wild type lip and back skin (scale bar=50μmicron).

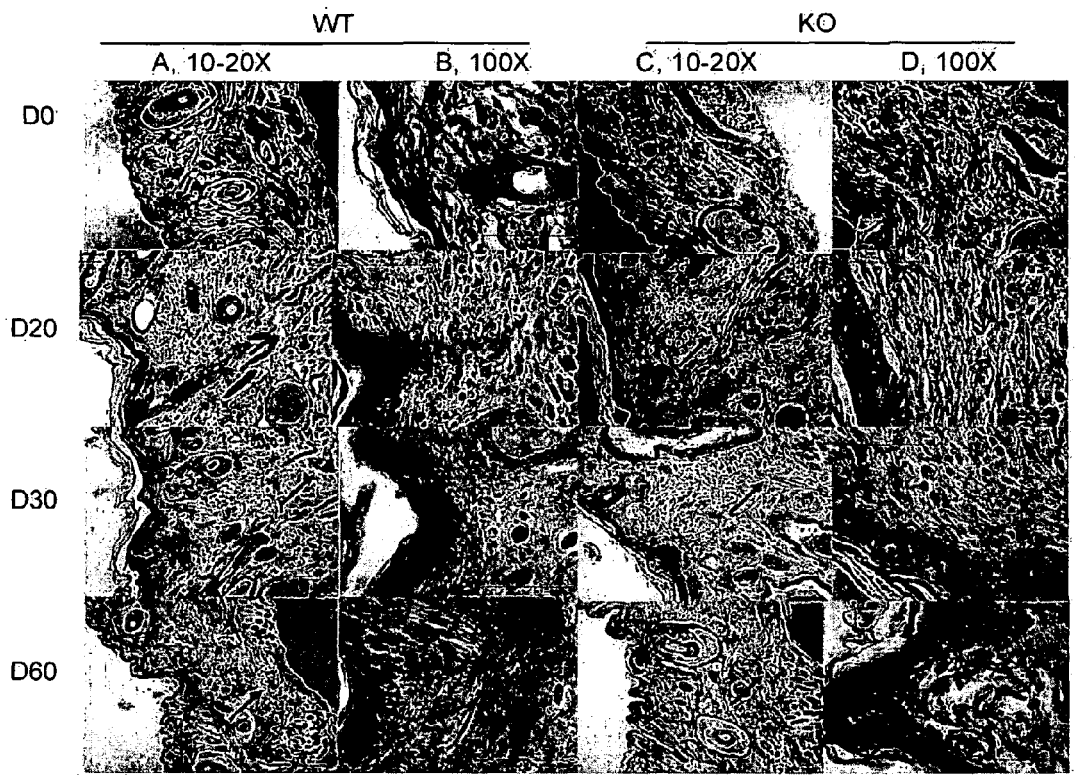

Figure 2. Collagen organization in WT and Hoxb13 KO wound biopsies (Scale bar = 50 μm). Column A, low magnification (10x or 20x lens) of WT mouse wound biopsies; Column B, high magnification (100x lens) of WT mouse wound biopsies; Column C, low magnification (10x or 20x lens) of Hoxb 13 KO mouse wound biopsies; Column D, high magnification (100x lens) of mouse wound biopsies. Row 1, unwounded skin; row 2, day 20 wound biopsies; row 3, day 30 wound biopsies; row 4, day 60 wound biopsies. Red arrows identify India ink location.

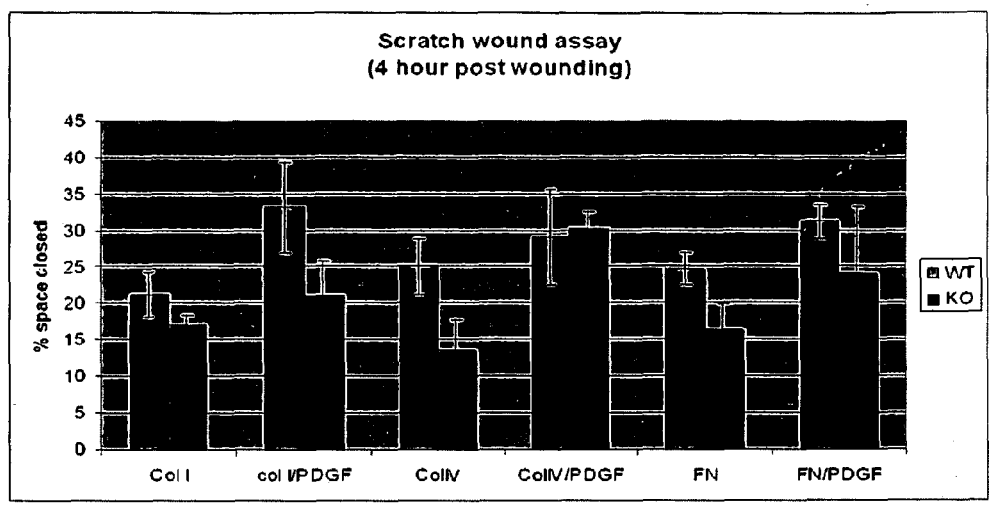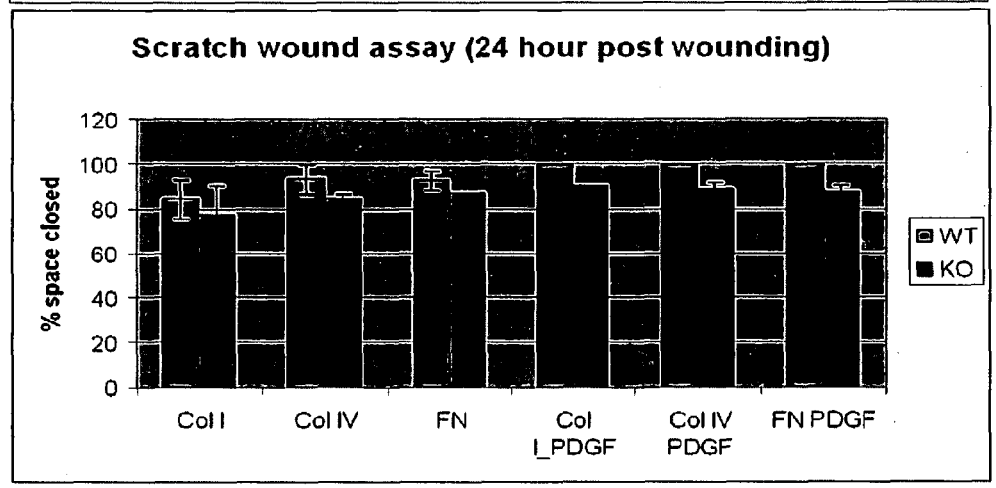
Figure 3. Scartch wound assays using primary dermal fibroblast isolated from WT and Hoxb13 KO mice (error bar calculated from six repeats).

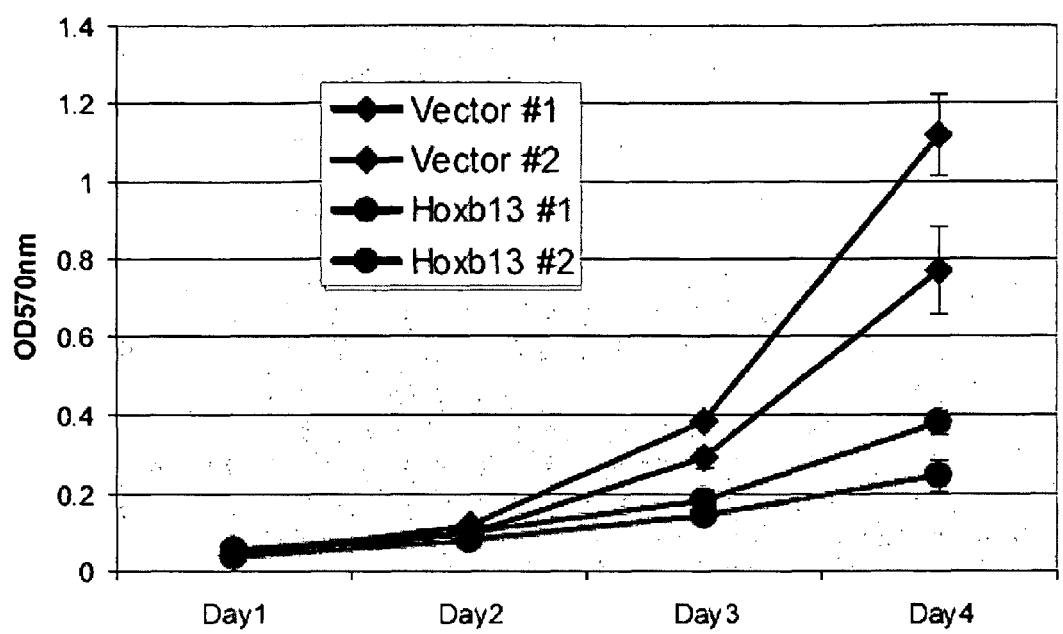
Figure 4. Reduced proliferation rate in HOXB13 expressing REK. 1x104 cells were seeded per well in 96 well plates. MTT assays were performed according to Molecular Probe's Instruction (n=4).

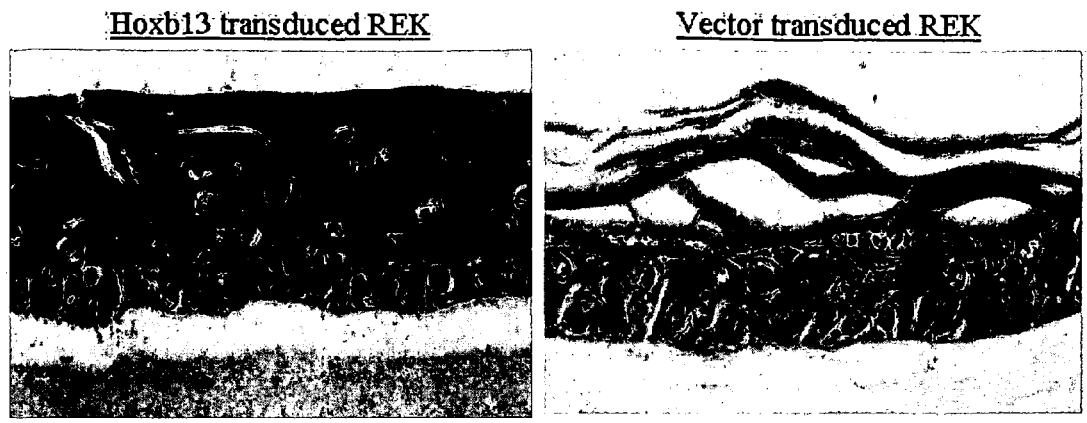
Figure 5. Overexpression of HOXB13 results in aberrant differentiation in day 5 lifted REK culture (H&E staining).
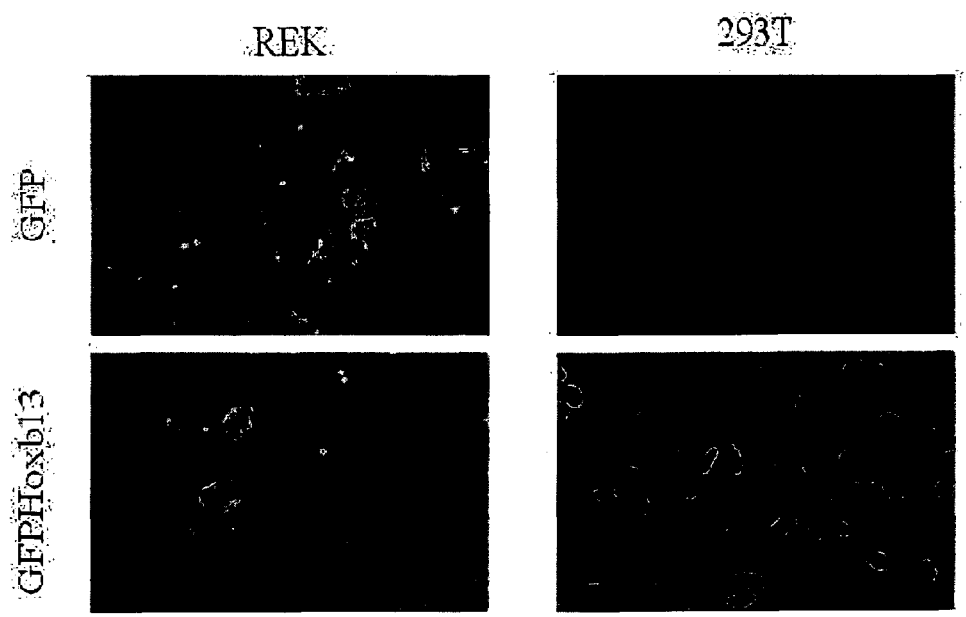
Figure 6. GFP-HOXB13 protein is localized to the nucleus in REK and 293T cells

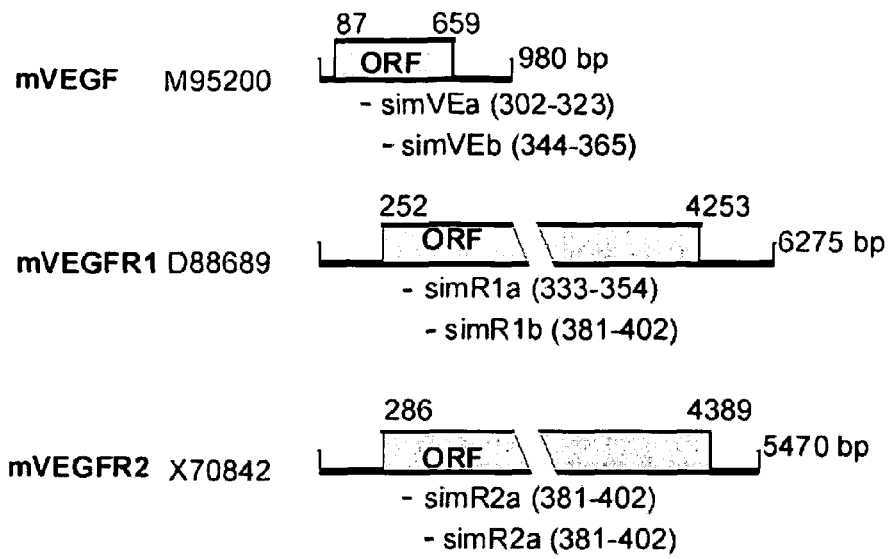
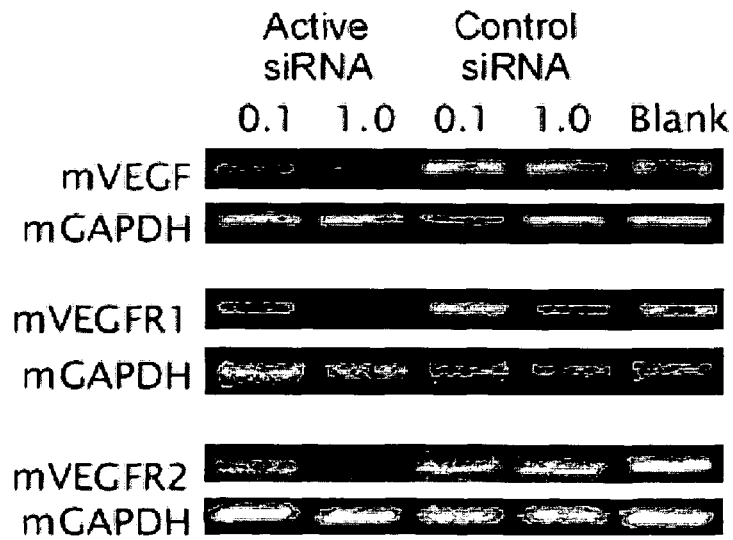
Figure 7. A. Locations of targeted sequences on mouse VEGF, VEGFR1 and VEGFR2 mRNAs. B. Measurements of mRNA knockdown after siRNA transfection *in vitro*.

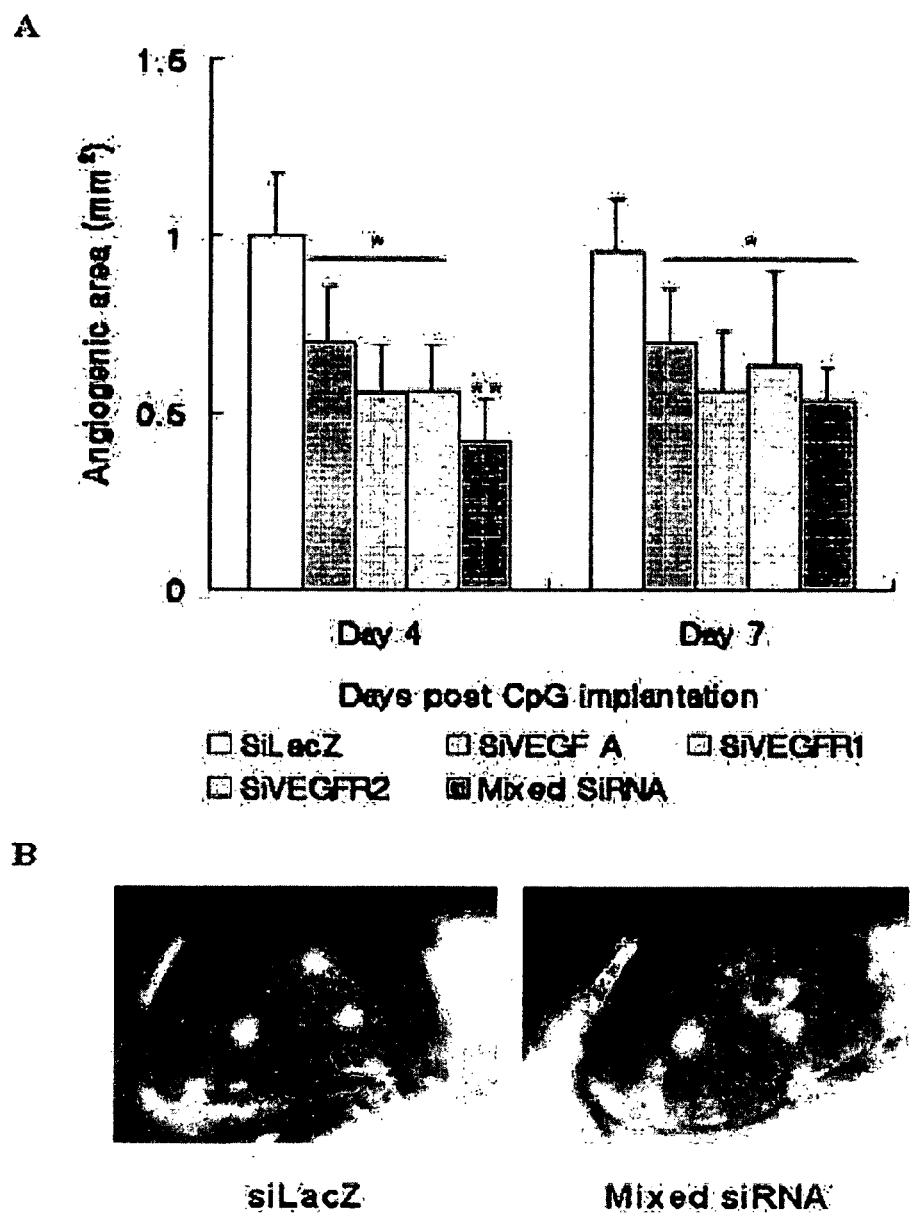
Figure 8. Local delivery of siRNAs targeting VEGF pathway genes inhibits the CpG ODN-induced angiogenesis.

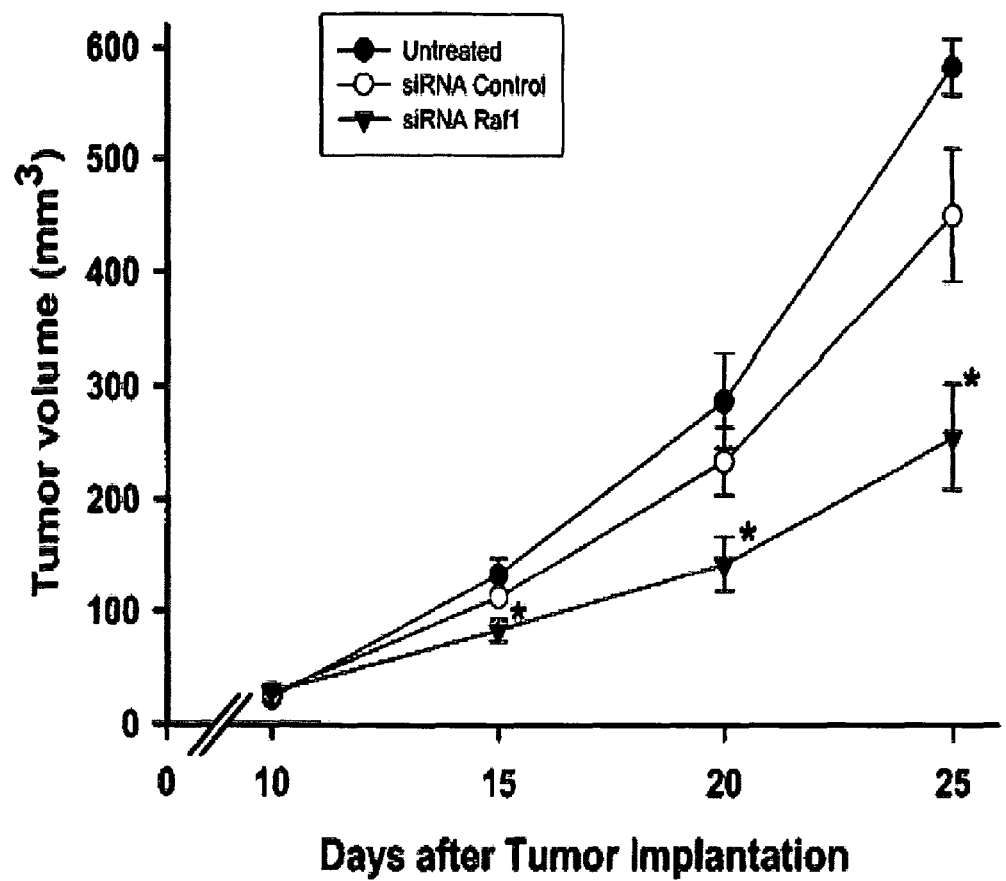
Figure 9. Raf-1 siRNA inhibits tumor growth *in vivo* after HK polymer mediated intratumoral delivery.

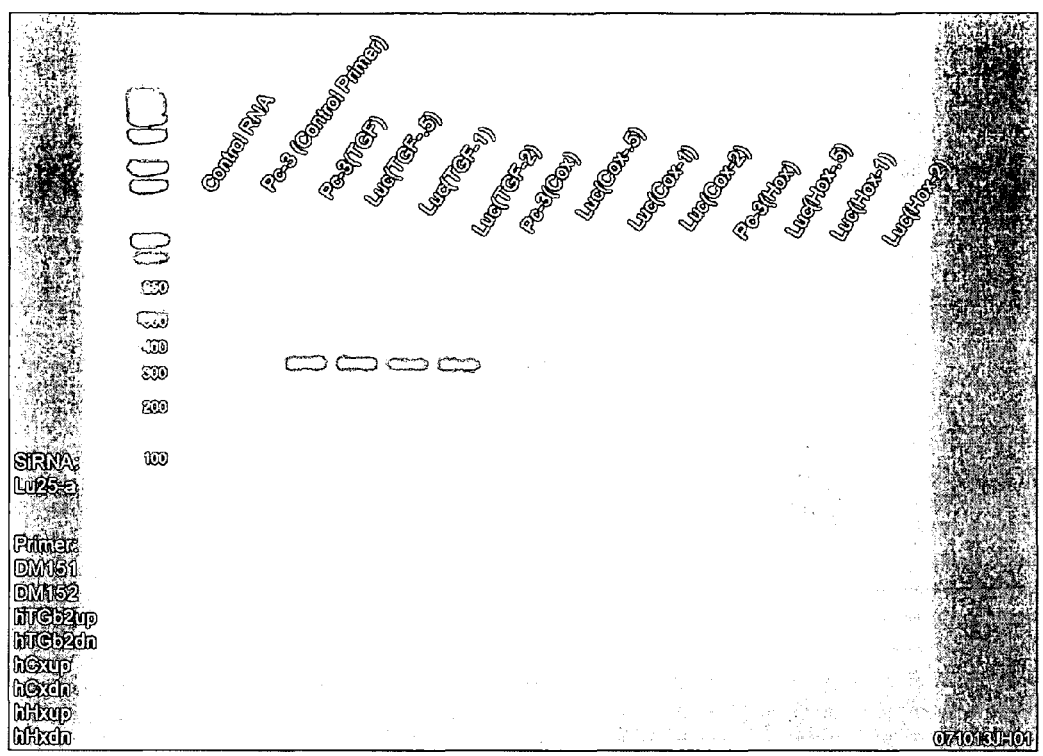
Figure 10. The primers used in the study are able to detect sequences of all three mRNA species in the PC3 cell total RNA samples. The RT-PCR primers used for analysis are shown in the column at the lower left. The targeting siRNA duplex shown in the column at the middle left.

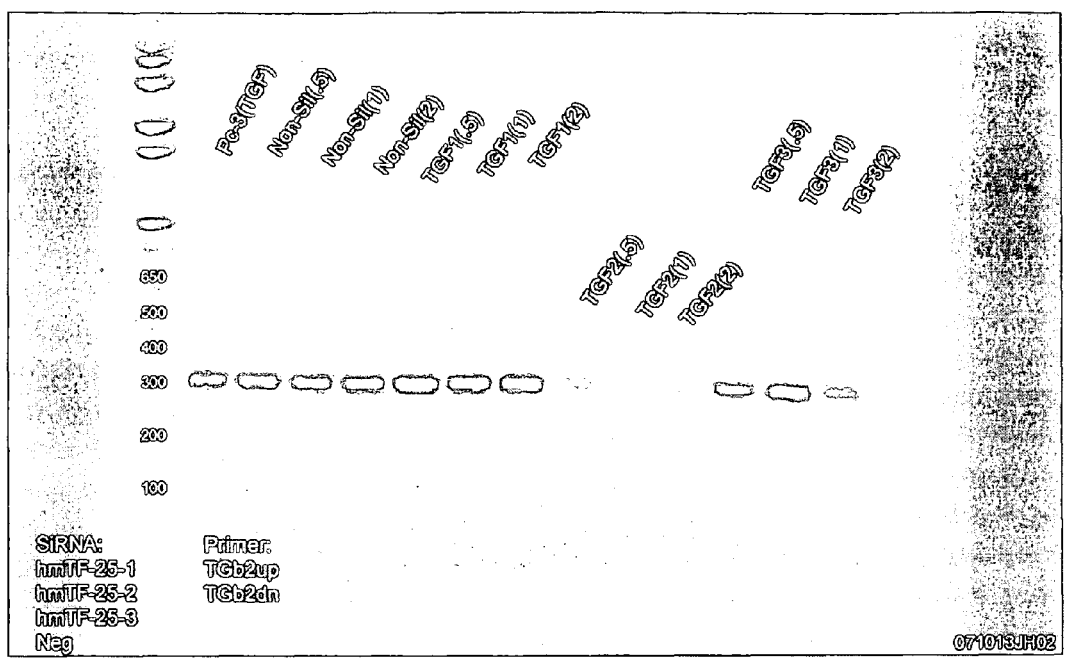
Figure 11. TGFbeta-2 siRNA (hmTF-25-2) is able to significantly knockdown targeted gene expression in the PC3 cell. The RT-PCR primers used for analysis are shown in the second column at the lower left. The targeting siRNA duplexes are shown in the first column at the lower left.

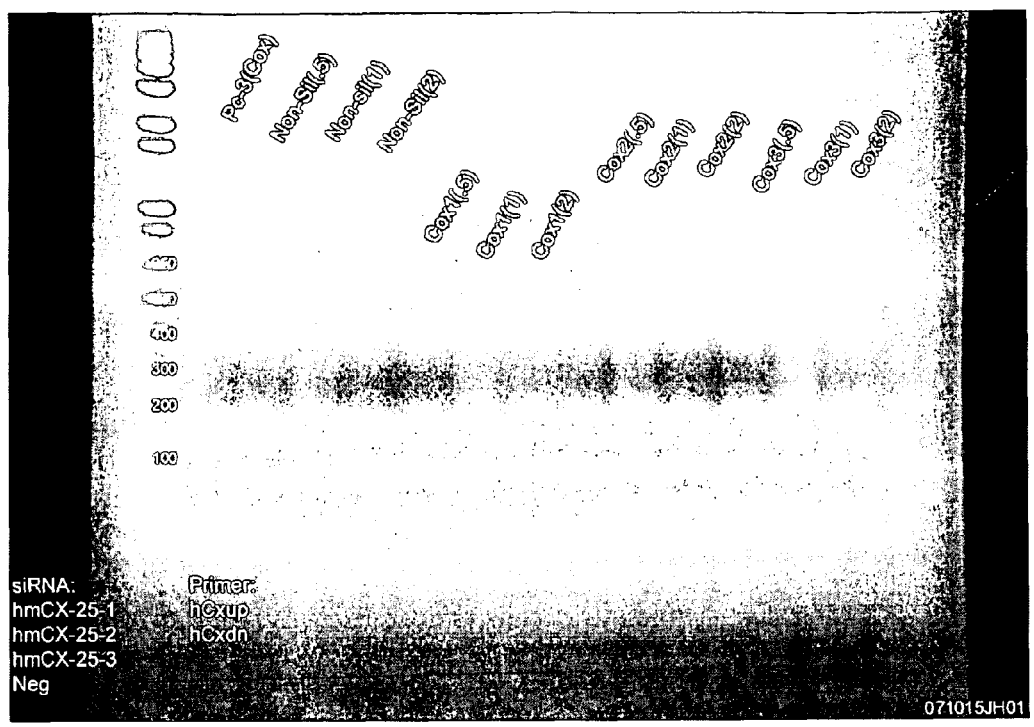
Figure 12. Cox1 siRNA (hmCX-25-1) is able to knockdown target gene expression in PC3 cell. The RT-PCR primers used for analysis are shown in the second column at the lower left. The targeting siRNA duplexes are shown in the first column at the lower left.

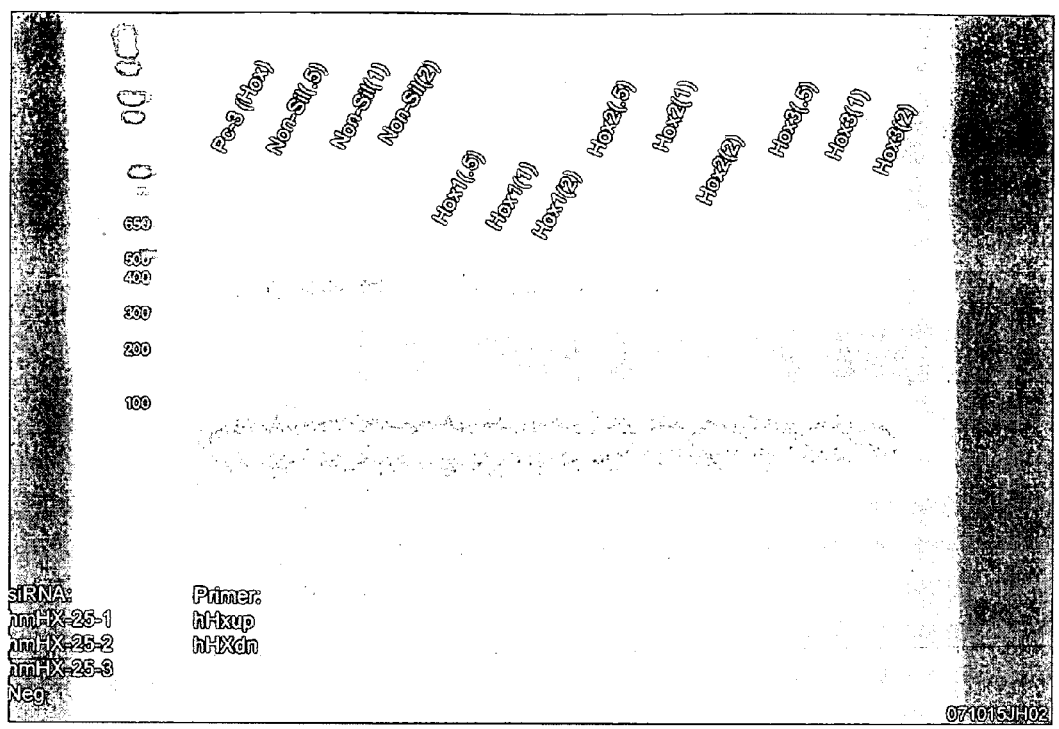
Figure 13. Hox1 siRNA (hmHX-25-1) is able to knockdown target gene expression in PC3 cell. The RT-PCR primers used for analysis are shown in the second column at the lower left. The targeting siRNA duplexes are shown in the first column at the lower left.

SEQUENCE LISTING

```
<160> NUMBER OF SEQ ID NOS: 333

<210> SEQ ID NO 1
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
caaggauauc gaaggcuugc uggga                                               25
```

```
<210> SEQ ID NO 2
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
ucccagcaag ccuucgauau ccuug                                               25

<210> SEQ ID NO 3
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3 gucuugguc uggugccugg ucuga                                                25

<210> SEQ ID NO 4
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
ucagaccagg caccagacca aagac                                               25

<210> SEQ ID NO 5
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
ccccggaggu gauuuccauc uacaa                                               25

<210> SEQ ID NO 6
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
uuguagaugg aaauccaccuc cgggg                                              25

<210> SEQ ID NO 7
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7 ggugggcugga acagccagau guguu                                              25

<210> SEQ ID NO 8
```

```
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
aacacaucug gcuguuccag ccacc                                              25

<210> SEQ ID NO 9
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
ggucuggugc cuggucugau gaugu                                              25

<210> SEQ ID NO 10
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
acaucaucag accaggcacc agacc                                              25

<210> SEQ ID NO 11
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
cccaagggcu accaugccaa cuucu                                              25

<210> SEQ ID NO 12
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
agaaguuggc augguagccc uuggg                                              25

<210> SEQ ID NO 13
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
cacgagccca agggcuacca ugcca                                              25

<210> SEQ ID NO 14
<211> LENGTH: 25
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 14
uggcauggua gcccuugggc ucgug                                              25

<210> SEQ ID NO 15
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
ccggagguga uuuccaucua caaca                                              25

<210> SEQ ID NO 16
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
uguuguagau ggaaaucacc uccgg                                              25

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ctccagctcc tgtgccttat                                                    20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
actggccata ggctggtatg                                                    20

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
aagccguccu gugugccgcu g                                                  21

<210> SEQ ID NO 20
<211> LENGTH: 21
<212> TYPE: RNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 20
aacgaugaag cccuggagug c                                              21

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
aaguuaaaag ugccugaacu g                                              21

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
aagcaggcca gacucucuuu c                                              21

<210> SEQ ID NO 23
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
aagcucagca cacagaaaga c                                              21

<210> SEQ ID NO 24
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
aaugcggcgg uggugacagu a                                              21

<210> SEQ ID NO 25
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
aagcuaugaa acgauauggg c                                              21

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
aaccgcugga gagcaacugc a                                                    21

<210> SEQ ID NO 27
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gaacatcgat gacaagctta ggtatcgata caagctgcct cgccttg                        47

<210> SEQ ID NO 28
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gaacatcgat gacaagctta ggtatcgata tagattgaag attccgc                        47

<210> SEQ ID NO 29
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gaacatcgat gacaagctta ggtatcgata ggtcactgac agaggcg                        47

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gaacatcgat gacaagctta ggtatcgata                                           30

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gatgtctacc agcgaagcta ctgccgtccg                                           30

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

```
gtcagctgct gggacaccgc ggtcttgcct                                              30
```

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33

```
ggcgctgcta gctgtcgctc tgtggttctg                                              30
```

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34

```
cctggtcacc agggctgctt                                                         20
```

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35

```
ccagccttct ccatggtggt                                                         20
```

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36

```
gcgggctgcc tcgcagtc                                                           18
```

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37

```
tcaccgcctt ggcttgtcac                                                         20
```

<210> SEQ ID NO 38
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38

```
gcuggaacag ccagaugugu ugcca                                                   25
```

<210> SEQ ID NO 39
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
uggcaacaca ucuggcuguu ccagc                                          25

<210> SEQ ID NO 40
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
cgccagauua ccaucugguu ucaga                                          25

<210> SEQ ID NO 41
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
ucugaaacca gaugguaauc uggcg                                          25

<210> SEQ ID NO 42
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
ggauccacga gcccaagggc uacca                                          25

<210> SEQ ID NO 43
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
ugguagcccu ugggcucgug gaucc                                          25

<210> SEQ ID NO 44
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
gagcccaagg gcuaccaugc caacu                                          25

```
<210> SEQ ID NO 45
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
aguuggcaug guagcccuug ggcuc                                       25

<210> SEQ ID NO 46
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
gagcaccauu cccuugaaa ggacu                                        25

<210> SEQ ID NO 47
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
aguccuuuca aggagaaugg ugcuc                                       25

<210> SEQ ID NO 48
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
ccucaauuca gucucucauc ugcaa                                       25

<210> SEQ ID NO 49
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
uugcagauga gagacugaau ugagg                                       25

<210> SEQ ID NO 50
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
gaggagccuu caggauuaca agauu                                       25

<210> SEQ ID NO 51
<211> LENGTH: 25
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
aaucuuguaa uccugaaggc uccuc                                           25

<210> SEQ ID NO 52
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 52
gcugacccug aaguucauct t                                               21

<210> SEQ ID NO 53
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 53
gaugaacuuc agggucagct t                                               21

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gcctctcgga gcgccagatt                                                 20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ctagtactgg ttatcgtgat                                                 20

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
cgggctgggc catggggtgg a                                               21
```

```
<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cctatcagta ttagcctgct t                                             21

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ggaagccttc tccaacctct                                               20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ggatacacct ctccaccaat                                               20

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gagtactacg ccaaggaggt t                                             21

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ccattcatga acagcatcag t                                             21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ctactgtgtg ctgagcacct t                                             21
```

```
<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
cgctgctcgg ccactctggc t                                             21

<210> SEQ ID NO 64
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
agggcggcau gggggaggcg gcgcc                                         25

<210> SEQ ID NO 65
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Lys His His His Lys His His His Lys His His His Lys His His His
1               5                   10                  15
Lys

<210> SEQ ID NO 66
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
ggcuccaugg agcccggcaa uuaug                                         25

<210> SEQ ID NO 67
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
ccauggagcc cggcaauuau gccac                                         25

<210> SEQ ID NO 68
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
ggagcccggc aauuaugcca ccuug                                         25
```

<210> SEQ ID NO 69
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
ggacaagagg cgcaagaucu cggca                                              25

<210> SEQ ID NO 70
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
gcaagaucuc ggcagccacc agccu                                              25

<210> SEQ ID NO 71
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
ccaucugguu ucagaaccgc cgggu                                              25

<210> SEQ ID NO 72
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
gauguuugca uucuuugccc agcac                                              25

<210> SEQ ID NO 73
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
caucaguuuu ucaagacaga ucaua                                              25

<210> SEQ ID NO 74
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
guuuuucaag acagaucaua agcga                                              25

<210> SEQ ID NO 75

<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
gugccugguc ugaugaugua ugcca                                             25

<210> SEQ ID NO 76
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
caccauucuc cuugaaagga cuuau                                             25

<210> SEQ ID NO 77
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
caauucaguc ucucaucugc aauaa                                             25

<210> SEQ ID NO 78
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
gcgggcagau ccugagcaag cugaa                                             25

<210> SEQ ID NO 79
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
ggcagauccu gagcaagcug aagcu                                             25

<210> SEQ ID NO 80
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
cagauccuga gcaagcugaa gcuca                                             25

<210> SEQ ID NO 81
<211> LENGTH: 25
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 81
cuccgaaaau gccaucccgc ccacu                                          25

<210> SEQ ID NO 82
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
gaaaaugcca ucccgcccac uuucu                                          25

<210> SEQ ID NO 83
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
cgcccacuuu cuacagaccc uacuu                                          25

<210> SEQ ID NO 84
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
cacuuucuac agacccuacu ucaga                                          25

<210> SEQ ID NO 85
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85 ccaggguga ucagaaaacu auaaa                                           25

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
ggtcacccgc gtgctaatgg t                                              21

<210> SEQ ID NO 87
<211> LENGTH: 21
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 87
cacccgcgtg ctaatggtgg a                                              21

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
ccaactattg cttcagctcc a                                              21

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
gcggcagctg tacattgact t                                              21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
ccacgagccc aagggctacc a                                              21

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
gcccaagggc taccatgcca a                                              21

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
ccaagggcta ccatgccaac t                                              21

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 93
cgcaagccca aggtggagca g                                           21

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
cgctcctgca agtgcagctg a                                           21

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
caagggctac catgccaact t                                           21

<210> SEQ ID NO 96
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
gaggtcaccc gcgtgctaat ggt                                         23

<210> SEQ ID NO 97
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
gtcacccgcg tgctaatggt gga                                         23

<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
gtgcggcagc tgtacattga ctt                                         23

<210> SEQ ID NO 99
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
cgagcccaag ggctaccatg cca                                           23

<210> SEQ ID NO 100
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
gcccaagggc taccatgcca act                                           23

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
caagggctac catgccaact tct                                           23

<210> SEQ ID NO 102
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
gtgcgctcct gcaagtgcag ctg                                           23

<210> SEQ ID NO 103
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
cccaagggct accatgccaa ctt                                           23

<210> SEQ ID NO 104
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
accaactatt gcttcagctc cac                                           23

<210> SEQ ID NO 105
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
ccgcccggcc cgctgcccga ggc                                           23

<210> SEQ ID NO 106
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
ggatccacga gcccaagggc tacca                                         25

<210> SEQ ID NO 107
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
gatccacgag cccaagggct accat                                         25

<210> SEQ ID NO 108
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
cacgagccca agggctacca tgcca                                         25

<210> SEQ ID NO 109
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
gagcccaagg gctaccatgc caact                                         25

<210> SEQ ID NO 110
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
cccaagggct accatgccaa cttct                                         25

<210> SEQ ID NO 111
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
gaggtcaccc gcgtgctaat ggtgg                                         25

<210> SEQ ID NO 112
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 112
gtacaacagc acccgcgacc gggtg                                              25

<210> SEQ ID NO 113
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 113
ggcgccgcct ccccatgcc gccct                                               25

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 114
cgggcagatc ctgagcaagc t                                                  21

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 115
gcagatcctg agcaagctga a                                                  21

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 116
ccatcccgcc cactttctac a                                                  21

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 117
ggcagatcct gagcaagctg a                                                  21

<210> SEQ ID NO 118
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
gatcctgagc aagctgaagc t                                              21

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
ggaggtgatt tccatctaca a                                              21

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
ccgaaaatgc catcccgccc a                                              21

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
cactttctac agaccctact t                                              21

<210> SEQ ID NO 122
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
cctgagcaag ctgaagctca cca                                            23

<210> SEQ ID NO 123
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
gagtactacg ccaaggaggt tta                                            23

<210> SEQ ID NO 124
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 124
ccatcccgcc cactttctac aga                                              23

<210> SEQ ID NO 125
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
ccgcccactt tctacagacc cta                                              23

<210> SEQ ID NO 126
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
cagatcctga gcaagctgaa gct                                              23

<210> SEQ ID NO 127
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
ccggaggtga tttccatcta caa                                              23

<210> SEQ ID NO 128
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
ctccgaaaat gccatcccgc cca                                              23

<210> SEQ ID NO 129
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
cactttctac agaccctact tca                                              23

<210> SEQ ID NO 130
<211> LENGTH: 23
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 130
ccagtggtga tcagaaaact ata                                              23

<210> SEQ ID NO 131
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
ggaagacccc acatctcctg cta                                              23

<210> SEQ ID NO 132
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
gcgggcagat cctgagcaag ctgaa                                            25

<210> SEQ ID NO 133
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
ggcagatcct gagcaagctg aagct                                            25

<210> SEQ ID NO 134
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
cagatcctga gcaagctgaa gctca                                            25

<210> SEQ ID NO 135
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
ccccggaggt gatttccatc tacaa                                            25

<210> SEQ ID NO 136
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 136
ccggaggtga tttccatcta caaca                                              25

<210> SEQ ID NO 137
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
ctccgaaaat gccatcccgc ccact                                              25

<210> SEQ ID NO 138
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
gaaaatgcca tcccgcccac tttct                                              25

<210> SEQ ID NO 139
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
cgcccacttt ctacagaccc tactt                                              25

<210> SEQ ID NO 140
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
cactttctac agaccctact tcaga                                              25

<210> SEQ ID NO 141
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
ccagtggtga tcagaaaact ataaa                                              25

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
```

```
caaaagctgg gaagccttct c                                              21
```

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143

```
gatgtttgca ttctttgccc a                                              21
```

<210> SEQ ID NO 144
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144

```
cattctttgc ccagcacttc a                                              21
```

<210> SEQ ID NO 145
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145

```
catcagtttt tcaagacaga t                                              21
```

<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146

```
cagtttttca agacagatca t                                              21
```

<210> SEQ ID NO 147
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147

```
gtttttcaag acagatcata a                                              21
```

<210> SEQ ID NO 148
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148

```
ctgcgccttt tcaaggatgg a                                              21
```

```
<210> SEQ ID NO 149
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
gtctttggtc tggtgcctgg t                                           21

<210> SEQ ID NO 150
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
ctttggtctg gtgcctggtc t                                           21

<210> SEQ ID NO 151
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
ggagcaccat tctccttgaa a                                           21

<210> SEQ ID NO 152
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
gatgtttgca ttctttgccc agc                                         23

<210> SEQ ID NO 153
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
catcagtttt tcaagacaga tca                                         23

<210> SEQ ID NO 154
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
cagtttttca agacagatca taa                                         23

<210> SEQ ID NO 155
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
ctgcgccttt tcaaggatgg aaa                                              23

<210> SEQ ID NO 156
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
gtctttggtc tggtgcctgg tct                                              23

<210> SEQ ID NO 157
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
ctttggtctg gtgcctggtc tga                                              23

<210> SEQ ID NO 158
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
ggtctggtgc ctggtctgat gat                                              23

<210> SEQ ID NO 159
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
ctggtgcctg gtctgatgat gta                                              23

<210> SEQ ID NO 160
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
gcctggtctg atgatgtatg cca                                              23

<210> SEQ ID NO 161
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 161
gagcaccatt ctccttgaaa gga                                              23

<210> SEQ ID NO 162
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
gatgtttgca ttctttgccc agcac                                            25

<210> SEQ ID NO 163
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
catcagtttt tcaagacaga tcata                                            25

<210> SEQ ID NO 164
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
gtttttcaag acagatcata agcga                                            25

<210> SEQ ID NO 165
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
gtctttggtc tggtgcctgg tctga                                            25

<210> SEQ ID NO 166
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
ggtctggtgc ctggtctgat gatgt                                            25

<210> SEQ ID NO 167
<211> LENGTH: 25
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 167
gtgcctggtc tgatgatgta tgcca                                              25

<210> SEQ ID NO 168
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
gagcaccatt ctccttgaaa ggact                                              25

<210> SEQ ID NO 169
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
caccattctc cttgaaagga cttat                                              25

<210> SEQ ID NO 170
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
cctcaattca gtctctcatc tgcaa                                              25

<210> SEQ ID NO 171
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
caattcagtc tctcatctgc aataa                                              25

<210> SEQ ID NO 172
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
ggctccatgg agcccggcaa t                                                  21

<210> SEQ ID NO 173
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 173
ccagcctatg gccagttacc t					21

<210> SEQ ID NO 174
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
ccatggagcc cggcaattat g					21

<210> SEQ ID NO 175
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
gcccggcaat tatgccacct t					21

<210> SEQ ID NO 176
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
caaggatatc gaaggcttgc t					21

<210> SEQ ID NO 177
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
gatatcgaag gcttgctggg a					21

<210> SEQ ID NO 178
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
gtggctggaa cagccagatg t					21

<210> SEQ ID NO 179
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179

```
gctggaacag ccagatgtgt t                                              21
```

<210> SEQ ID NO 180
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180

```
gatctcggca gccaccagcc t                                              21
```

<210> SEQ ID NO 181
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181

```
cgccagatta ccatctggtt t                                              21
```

<210> SEQ ID NO 182
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182

```
ggctccatgg agcccggcaa tta                                            23
```

<210> SEQ ID NO 183
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183

```
catggagccc ggcaattatg cca                                            23
```

<210> SEQ ID NO 184
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184

```
ggagcccggc aattatgcca cct                                            23
```

<210> SEQ ID NO 185
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185

```
gtggctggaa cagccagatg tgt                                            23
```

<210> SEQ ID NO 186
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
cgccagatta ccatctggtt tca                                          23

<210> SEQ ID NO 187
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
ccagattacc atctggtttc aga                                          23

<210> SEQ ID NO 188
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
atctggtttc agaaccgccg ggt                                          23

<210> SEQ ID NO 189
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
aagatctcgg cagccaccag cct                                          23

<210> SEQ ID NO 190
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
ggctccatgg agcccggcaa ttatg                                        25

<210> SEQ ID NO 191
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
ccatggagcc cggcaattat gccac                                        25

<210> SEQ ID NO 192
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 192
ggagcccggc aattatgcca ccttg    25

<210> SEQ ID NO 193
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 193
caaggatatc gaaggcttgc tggga    25

<210> SEQ ID NO 194
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 194
ggtggctgga acagccagat gtgtt    25

<210> SEQ ID NO 195
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 195
gctggaacag ccagatgtgt tgcca    25

<210> SEQ ID NO 196
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 196
ggacaagagg cgcaagatct cggca    25

<210> SEQ ID NO 197
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 197
gcaagatctc ggcagccacc agcct    25

<210> SEQ ID NO 198
<211> LENGTH: 25

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
cgccagatta ccatctggtt tcaga                                          25

<210> SEQ ID NO 199
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
ccatctggtt tcagaaccgc cgggt                                          25

<210> SEQ ID NO 200
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
caccctcctc cgggccgcgc t                                              21

<210> SEQ ID NO 201
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
ctcctccggg ccgcgctccc t                                              21

<210> SEQ ID NO 202
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
gtactgaatt tcgccgccac a                                              21

<210> SEQ ID NO 203
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
ctgaatttcg ccgccacagg a                                              21

<210> SEQ ID NO 204
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 204
ggagcgcccg ccccgcggcc t                                              21

<210> SEQ ID NO 205
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
ctgctgctcc tcggctgcgg a                                              21

<210> SEQ ID NO 206
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
gctgctcctc ggctgcggat a                                              21

<210> SEQ ID NO 207
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
gatccacagc atccgggacc t                                              21

<210> SEQ ID NO 208
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
ccacagcatc cgggacctcc a                                              21

<210> SEQ ID NO 209
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
catccgggac ctccagcgac t                                              21

<210> SEQ ID NO 210
<211> LENGTH: 23
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 210
gccaccctcc tccgggccgc gct                                              23

<210> SEQ ID NO 211
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
ccctcctccg ggccgcgctc cct                                              23

<210> SEQ ID NO 212
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
gatggtactg aatttcgccg cca                                              23

<210> SEQ ID NO 213
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
ctggagcgcc cgccccgcgg cct                                              23

<210> SEQ ID NO 214
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
gcgcccgccc cgcggcctcg cct                                              23

<210> SEQ ID NO 215
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
gcctcgggac gcgatgagga cct                                              23

<210> SEQ ID NO 216
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 216
ggcttgcctg ctgctcctcg gct                                            23

<210> SEQ ID NO 217
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
gcctgctgct cctcggctgc gga                                            23

<210> SEQ ID NO 218
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
cagatccaca gcatccggga cct                                            23

<210> SEQ ID NO 219
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
gaccaggacg gtcatttacg aga                                            23

<210> SEQ ID NO 220
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
gcgccaccct cctccgggcc gcgct                                          25

<210> SEQ ID NO 221
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
caccctcctc cgggccgcgc tccct                                          25

<210> SEQ ID NO 222
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
```
gggatggtac tgaatttcgc cgcca                          25

<210> SEQ ID NO 223
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
gatggtactg aatttcgccg ccaca                          25

<210> SEQ ID NO 224
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
ggtactgaat tcgccgcca cagga                           25

<210> SEQ ID NO 225
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
ggctggagcg cccgccccgc ggcct                          25

<210> SEQ ID NO 226
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
gagcgcccgc cccgcggcct cgcct                          25

<210> SEQ ID NO 227
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
ccagcgcctc gggacgcgat gagga                          25

<210> SEQ ID NO 228
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
gcgcctcggg acgcgatgag gacct                          25

```
<210> SEQ ID NO 229
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
gcctgctgct cctcggctgc ggata                                             25

<210> SEQ ID NO 230
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
ggagacggag aacagcgcgc t                                                 21

<210> SEQ ID NO 231
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
ggagaacagc gcgctgcagc t                                                 21

<210> SEQ ID NO 232
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
gaacagcgcg ctgcagctgc a                                                 21

<210> SEQ ID NO 233
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
gaggctggga gatgatcaga a                                                 21

<210> SEQ ID NO 234
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
ggctgggaga tgatcagaaa a                                                 21

<210> SEQ ID NO 235
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
gagccttact gaggacttgg a                                                   21

<210> SEQ ID NO 236
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
cagttagcag atgaaacttt a                                                   21

<210> SEQ ID NO 237
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
gttagcagat gaaactttac t                                                   21

<210> SEQ ID NO 238
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
caatgggagg ctgggagatg a                                                   21

<210> SEQ ID NO 239
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
ctggagacgg agaacagcgc gct                                                 23

<210> SEQ ID NO 240
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
gagaacagcg cgctgcagct gca                                                 23

<210> SEQ ID NO 241
<211> LENGTH: 23
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 241
gagccttact gaggacttgg agt                                            23

<210> SEQ ID NO 242
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
gggaggctgg gagatgatca gaa                                            23

<210> SEQ ID NO 243
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
cagagcctta ctgaggactt gga                                            23

<210> SEQ ID NO 244
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
cgacacggcc cgcgagcgcg cca                                            23

<210> SEQ ID NO 245
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
cagttagcag atgaaacttt act                                            23

<210> SEQ ID NO 246
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
gttagcagat gaaactttac tta                                            23

<210> SEQ ID NO 247
<211> LENGTH: 23
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 247
ccaatgggag gctgggagat gat                                              23

<210> SEQ ID NO 248
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
gaagatgtga aggttatatt gaa                                              23

<210> SEQ ID NO 249
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
gcctggagac ggagaacagc gcgct                                            25

<210> SEQ ID NO 250
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
cggagaacag cgcgctgcag ctgca                                            25

<210> SEQ ID NO 251
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
gagccttact gaggacttgg agttt                                            25

<210> SEQ ID NO 252
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
gggaggctgg gagatgatca gaaaa                                            25

<210> SEQ ID NO 253
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
gtcagagcct tactgaggac ttgga                                              25

<210> SEQ ID NO 254
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
gacgacacgg cccgcgagcg cgcca                                              25

<210> SEQ ID NO 255
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
gacacggccc gcgagcgcgc caagc                                              25

<210> SEQ ID NO 256
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
cagttagcag atgaaacttt actta                                              25

<210> SEQ ID NO 257
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
gatcaaccaa tgggaggctg ggaga                                              25

<210> SEQ ID NO 258
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
ccaatgggag gctgggagat gatca                                              25

<210> SEQ ID NO 259
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
gtgtgcgcag acagtgctcc a                                         21

<210> SEQ ID NO 260
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
ccaccatgcc aagtggtccc a                                         21

<210> SEQ ID NO 261
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
cctggtggac atcttccagg a                                         21

<210> SEQ ID NO 262
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
gcacatagga gagatgagct t                                         21

<210> SEQ ID NO 263
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
caagatccgc agacgtgtaa a                                         21

<210> SEQ ID NO 264
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
ggcgaggcag cttgagttaa a                                         21

<210> SEQ ID NO 265
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
cttgagttaa acgaacgtac t                                         21

<210> SEQ ID NO 266
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
ggaaggagcc tccctcaggg t                                              21

<210> SEQ ID NO 267
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
cactttgggt ccggagggcg a                                              21

<210> SEQ ID NO 268
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
cagtattctt ggttaatatt t                                              21

<210> SEQ ID NO 269
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
gcctccgaaa ccatgaactt tct                                            23

<210> SEQ ID NO 270
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
ctccaccatg ccaagtggtc cca                                            23

<210> SEQ ID NO 271
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
cctggtggac atcttccagg agt                                            23

<210> SEQ ID NO 272
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
cagcacatag gagagatgag ctt                                           23

<210> SEQ ID NO 273
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
gcttgagtta aacgaacgta ctt                                           23

<210> SEQ ID NO 274
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
gttaaacgaa cgtacttgca gat                                           23

<210> SEQ ID NO 275
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
ggaaggagcc tccctcaggg ttt                                           23

<210> SEQ ID NO 276
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
ctccctcagg gtttcgggaa cca                                           23

<210> SEQ ID NO 277
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
ctaatgttat tggtgtcttc act                                           23

<210> SEQ ID NO 278
<211> LENGTH: 23

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
gagaaagtgt tttatatacg gta                                          23

<210> SEQ ID NO 279
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
cctccgaaac catgaacttt ctgct                                        25

<210> SEQ ID NO 280
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
ccaccatgcc aagtggtccc aggct                                        25

<210> SEQ ID NO 281
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
ccctggtgga catcttccag gagta                                        25

<210> SEQ ID NO 282
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
gatccgcaga cgtgtaaatg ttcct                                        25

<210> SEQ ID NO 283
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
cgcagacgtg taaatgttcc tgcaa                                        25

<210> SEQ ID NO 284
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 284
gtaaatgttc ctgcaaaaac acaga                                           25

<210> SEQ ID NO 285
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
cagcttgagt taaacgaacg tactt                                           25

<210> SEQ ID NO 286
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
gttaaacgaa cgtacttgca gatgt                                           25

<210> SEQ ID NO 287
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
ccatgccaag tggtcccagg ctgca                                           25

<210> SEQ ID NO 288
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
cttcaaggac cccaagcggc t                                               21

<210> SEQ ID NO 289
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
ggccacttca aggaccccaa g                                               21

<210> SEQ ID NO 290
<211> LENGTH: 21
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 290
ggcttcttcc tgcgcatcca t                                            21

<210> SEQ ID NO 291
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
caagcagaag agagaggagt t                                            21

<210> SEQ ID NO 292
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
cagaagagag aggagttgtg t                                            21

<210> SEQ ID NO 293
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
gagaggagtt gtgtctatca a                                            21

<210> SEQ ID NO 294
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
gaagagagag gagttgtgtc t                                            21

<210> SEQ ID NO 295
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
gaatctaata actacaatac t                                            21

<210> SEQ ID NO 296
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 296
cagttggtat gtggcactga a                                          21

<210> SEQ ID NO 297
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
cactgaaacg aactgggcag t                                          21

<210> SEQ ID NO 298
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
cacttcaagg accccaagcg gct                                        23

<210> SEQ ID NO 299
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
caagcagaag agagaggagt tgt                                        23

<210> SEQ ID NO 300
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
gcagaagaga gaggagttgt gtt                                        23

<210> SEQ ID NO 301
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
cagaagagag aggagttgtg tct                                        23

<210> SEQ ID NO 302
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
```

```
gaagagagag gagttgtgtc tat                                            23
```

<210> SEQ ID NO 303
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303

```
gagagaggag ttgtgtctat caa                                            23
```

<210> SEQ ID NO 304
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304

```
ggaatctaat aactacaata ctt                                            23
```

<210> SEQ ID NO 305
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305

```
ggtatgtggc actgaaacga act                                            23
```

<210> SEQ ID NO 306
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306

```
gttggtatgt ggcactgaaa cga                                            23
```

<210> SEQ ID NO 307
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307

```
gtggcactga aacgaactgg gca                                            23
```

<210> SEQ ID NO 308
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308

```
gccacttcaa ggaccccaag cggct                                          25
```

<210> SEQ ID NO 309
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
caagcagaag agagaggagt tgtgt                                               25

<210> SEQ ID NO 310
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
gaagagagag gagttgtgtc tatca                                               25

<210> SEQ ID NO 311
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
cagaagagag aggagttgtg tctat                                               25

<210> SEQ ID NO 312
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
ggaatctaat aactacaata cttac                                               25

<210> SEQ ID NO 313
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
ctaataacta caatacttac cggtc                                               25

<210> SEQ ID NO 314
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
cagttggtat gtggcactga aacga                                               25

<210> SEQ ID NO 315

```
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
gtggcactga aacgaactgg gcagt                                             25

<210> SEQ ID NO 316
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
tcttccaatg tctgctaaga gctga                                             25

<210> SEQ ID NO 317
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 317
ccaugccaag uggucccagg cugca                                             25

<210> SEQ ID NO 318
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 318
caaggauauc gaaggcuugc u                                                 21

<210> SEQ ID NO 319
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 319
gucuuugguc uggugccugg u                                                 21

<210> SEQ ID NO 320
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 320
cacgagccca agggcuacca u                                                 21

<210> SEQ ID NO 321
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 321
ggaggugauu uccaucuaca a                                           21

<210> SEQ ID NO 322
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 322
gucuuugguc uggugccugg ucu                                         23

<210> SEQ ID NO 323
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 323 gggauggua c ugaauuucgc cgcca                                      25

<210> SEQ ID NO 324
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 324
gagccuuacu gaggacuugg aguuu                                       25

<210> SEQ ID NO 325
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 325
gucagagccu uacugaggac uugga                                       25

<210> SEQ ID NO 326
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Lys His His His Lys His His His Asn His His His Asn His His His
 1               5                  10                  15

Asn

<210> SEQ ID NO 327
<211> LENGTH: 25
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 327
ugccgagauc uugcgccucu ugucc                                          25

<210> SEQ ID NO 328
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 328
aggcuggugg cugccgagau cuugc                                          25

<210> SEQ ID NO 329
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 329
uaugaucugu cuugaaaaac ugaug                                          25

<210> SEQ ID NO 330
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 330
uggcauacau caucagacca ggcac                                          25

<210> SEQ ID NO 331
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 331
gauccacgag cccaagggcu accau                                          25

<210> SEQ ID NO 332
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 332
augguagccc uugggcucgu ggauc                                          25

<210> SEQ ID NO 333
<211> LENGTH: 25
<212> TYPE: RNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 333
ggcgccgccu cccccaugcc gcccu                                              25
```

MULTI-TARGETED RNAI THERAPEUTICS FOR SCARLESS WOUND HEALING OF SKIN

This application is a U.S. national phase application of, and claims priority to and the benefit of, International Patent Application No. PCT/US2008/012498, filed Nov. 6, 2008, and it claims priority to, and the benefit of, U.S. Provisional Patent Application No. 60/985,820, filed Nov. 6, 2007. The disclosures of these applications are expressly incorporated herein by reference in their entireties.

FIELD OF INVENTION

The present invention relates to compositions and methods for improvement of skin scarless wound healing and other skin conditions, such as psoriasis and lupus-caused cutaneous lesions, using compositions of small interfering RNA (siRNA) molecules with multiple oligonucleotide sequences targeting multiple disease causing genes.

BACKGROUND

Skin, the largest organ of the body, consists of an underlying mesenchymal (dermal) layer and an outer epithelial (epidermal) layer. The primary function of the skin is to serve as a protective barrier against the environment. Loss of the integrity of large portions of the skin as a result of injury or illness may lead to major disability or even death. Every year in the United States more than 1.25 million people have burns and 6.5 million have chronic skin ulcers caused by pressure, venous stasis, or diabetes mellitus. The primary goals of the treatment of wounds are rapid wound closure and a functional and aesthetically satisfactory scar (1). Recent advances in cellular and molecular biology have greatly expanded our understanding of the biologic processes involved in wound repair and tissue regeneration and have led to improvements in wound care (2).

Wound Healing: A Response to Skin Injury

The response to injury is a phylogenetically primitive, yet essential innate host immune response for restoration of tissue integrity. Tissue disruption in higher vertebrates, unlike lower vertebrates, results not in tissue regeneration, but in a rapid repair process leading to a fibrotic scar. Wound healing, whether initiated by trauma, microbes or foreign materials, proceeds via an overlapping pattern of events including coagulation, inflammation, epithelialization, formation of granulation tissue, matrix and tissue remodeling. The process of repair is mediated in large part by interacting molecular signals, primarily cytokines, that motivate and orchestrate the manifold cellular activities which underscore inflammation and healing. Response to injury is frequently modeled in the skin (1), but parallel coordinated and temporally regulated patterns of mediators and cellular events occur in most tissues subsequent to injury. The initial injury triggers coagulation and an acute local inflammatory response followed by mesenchymal cell recruitment, proliferation and matrix synthesis. Failure to resolve the inflammation can lead to chronic nonhealing wounds, whereas uncontrolled matrix accumulation, often involving aberrant cytokine pathways, leads to excess scarring and fibrotic sequelae. Continuing progress in deciphering the role of cytokines in wound healing provides opportunities to explore pathways to inhibit/enhance appropriate cytokines to control or modulate pathologic healing.

Fetal Wounds are Healed Faster without Scar

Wound healing is a dynamic, interactive process involving soluble mediators, blood cells, extracellular matrix, and parenchymal cells. Wound healing has three phases—inflammation, tissue formation, and tissue remodeling—that overlap in time (1,2). During embryonic skin development, keratinocytes originate from a single-cell proliferating basal layer, undergo growth arrest, and migrate upward in a tightly controlled program of differentiation to produce the morphologically distinct layers of the epidermis. Using a similar program, the epidermis is continually renewed during the life of the organism. Adult mammalian skin also has tremendous capacities for repair following injury. However, responses that have been optimized for rapid wound closure and prevention of infection result in an imperfect restoration of the skin as shown by epidermal and dermal scarring.

In contrast to repair of adult skin, mammalian fetal cutaneous wounds made early in gestation heal by a process of regeneration, in which the epidermal and dermal layers are perfectly reconstituted without scar formation (1, 2). There are several notable contrasts in the course of fetal vs. adult wound healing. Fetal wounds close faster, show little or no inflammatory response (3), and exhibit a different profile of cytokine/growth factor expression, with generally lower levels (4).

TGF-β Antibody Partially Reduced the Amount of Scarring

Evidence demonstrates that wound healing is regulated by a group of cytokines, growth factors and their receptors (5-7). They influence cell migration, growth and proliferation in a complex, orchestrated manner and are involved in neutrophil and macrophage infiltration, angiogenesis, fibroplasia, matrix deposition, scarring and reepithelialization. Besides platelets and macrophages, fibroblasts are the major cellular source of cytokines or growth factors during wound healing. The scarless wound healing in fetal skin at early gestation is a result of the unique cytokine or growth factor profile.

Of these, transforming growth factor-beta (TGF-β) has been most widely studied as it is implicated in the transition between scarless healing and repair with scar formation. Called growth factors for historical reasons, their main function is to control cell proliferation and differentiation and to stimulate the synthesis of extracellular matrix such as collagen. TGF-β has been found by immunohistochemistry in unwounded fetal skin, and high levels of TGF-β are expressed at gestational ages associated with scarless repair. Exogenous application of TGF-β to normally scarless fetal wounds resulted in scar formation and an adult-like inflammatory response was observed. The profibrotic nature of TGF-β was confirmed in wounds of adult rats as neutralizing TGF-β antibody partially reduced the amount of scarring. TGF-β stimulates collagen I production, which is the predominant collagen type in adult skin. On the other hand, TGF-β neutralizing antibodies do not entirely prevent scarring in the adult skin, and recent studies question the efficacy of TGF-β as an dominant Scar-forming factor (8-15).

Studies have also found that decreased and rapidly cleared TGF-beta 1 and -beta 2 expression accompanied by increased and prolonged TGF-beta 3 levels in wounded E16 animals correlated with organized collagen deposition. In contrast, increased and prolonged TGF-beta 1 and -beta 2 expression accompanied by decreased and delayed TGF-beta 3 expression in wounded E19 animals correlated with disorganized collagen architecture. This means that increased TGF-beta 1, -beta 2, and decreased TGF-beta 3 expression is responsible for the late gestation fetal scar formation. These observations have broad implications for understanding the role of TGF-β in the endogenous wound healing response, in that an excess of TGF-β may be a normal constituent of the response for rapid and optimal protection of the host. In the absence of infection, however, reduction of this overexuberant recruitment, inflammation and keratinocyte suppression may result in a more cosmetically acceptable scar.

COX-2 Inhibitor Reduces Scar Tissue Formation and Enhances Tensile Strength

While the interleukins IL-6, IL-8, and IL-10 have been studied in fetal wound repair, COX-2 has also received much attention recently as it is involved in diseases associated with dysregulated inflammatory conditions, such as rheumatoid and osteoarthritis, cardiovascular disease, and the carcinogenesis process (16-20). COX-2 undergoes immediate-early up-regulation in response to an inflammatory stimulus (20, 21), such as a wound. It functions by producing prostaglandins that control many aspects of the resulting inflammation, including the induction of vascular permeability and the infiltration and activation of inflammatory cells (22). Interest in the role of the COX-2 pathway and other aspects of inflammation in the adult wound repair process is increasing (35) as these early events have been shown to regulate the outcome of repair. Based on the involvement of COX-2 in inflammation and the recent demonstration that it contributes to several aspects of adult wound repair (23-25), the role of COX-2 in the fetal wound healing process has been examined. These studies demonstrate differential expression of the COX-2 enzyme in early and late gestation fetal wounds.

Furthermore, $PGE_2$, a COX-2 product shown to mediate many processes in the skin, caused a delay in healing and the production of a scar when introduced into early fetal wounds. The involvement of the COX-2 pathway in scar formation is further highlighted by the fact that increasing $PGE_2$ levels in scarless wounds results in the conversion of a scarless healing process into one of repair with the generation of a scar. The introduction of $PGE_2$ induced inflammation in fetal wounds (26), although their effect on collagen deposition or fibrosis was not examined. Whether $PGE_2$ displays immunosuppressive or anti-inflammatory properties or instead acts as a pro-inflammatory molecule most likely results from differences in the expression or activity of the receptors for $PGE_2$. There are several plausible mechanisms by which $PGE_2$ could be inducing scar formation in fetal wounds. $PGE_2$ could be enhancing acute inflammation, already known to interfere with scarless healing, thereby indirectly promoting scar formation through the recruitment and activation of inflammatory cells. $PGE_2$ treatment could be both delaying healing and promoting scar tissue deposition through increases in the pro-fibrotic TGFβ1 (27). Disruption of the TGFβ signaling pathway in smad3-deficient mice has been shown to speed the rate of healing, and extensive data demonstrates restricted TGFβ3 levels are crucial to scarless healing. Lastly, there are data demonstrating increased fibroblast proliferation in response to $PGE_2$ suggests that $PGE_2$ could be directly stimulating fibroblasts to proliferate, amplifying collagen production and scarring. This idea is also supported by previous studies demonstrating an increase in collagen deposition and proliferation by fibroblasts following exposure to $PGE_2$. The substantial data suggested the low levels of COX-2 expression and $PGE_2$ may be necessary for the scarless repair of fetal skin. The fact that $PGE_2$ induces scar formation in fetal skin further supporting a role for the COX-2 pathway in scar formation. Using a COX-2 inhibitor celecoxib to treat incisional wounds, the role of COX-2 in the wound healing process was examined with significant inhibition of several parameters of inflammation in the wound site (28). This decrease in the early inflammatory phase of wound healing had a profound effect on later events in the wound healing process, namely a reduction in scar tissue formation, without disrupting reepithelialization or decreasing tensile strength.

Skin Wounds of HoxB13 KO Mouse Heals Faster with Less Scar Tissue Formation

The evolutionarily conserved families of Hox transcription factors have been considered attractive candidates for regulation of fetal skin regeneration due to their critical roles for directing differentiation during organogenesis. Studies have identified one particular member of the Hox protein family, HoxB13, as the predominate Hox gene expressed in primary fibroblast cultures from second trimester skin (29). Subsequent wound healing studies using second trimester fetal skin (which heals without a scar) and human adult skin demonstrated that HoxB13 is differentially expressed in fetal vs. adult wounds. Interestingly, HoxB13 expression was significantly down-regulated in fetal wounds compared with unwounded controls. In contrast, there was no significant change in HoxB13 expression in adult wounds compared with unwounded controls. Together, these results suggest that down-regulation of HoxB13 expression may be necessary for fetal scarless wound healing. It also raises the possibility that reducing or eliminating HoxB13 from adult skin could improve wound healing.

Studies on cutaneous excisional and incisional wound healing in adult HoxB13 knockout (KO) mice demonstrated that HoxB13 KO wounds exhibit several characteristics of early gestational fetal wounds, including faster closure, increased tensile strength, and less dermal scarring when compared with wounds from their wild-type (WT) counterparts. Biochemical evaluation revealed that levels of epidermal and dermal HA are significantly higher in unwounded adult HoxB13 KO skin compared with WT skin. Using a histological comparison, HoxB13 KO incisional wounds exhibit enhanced healing with better restored dermal integrity of HoxB13 KO wounds than in WT wounds. HoxB13 KO adult excisional wounds also close faster than WT excisional wounds. In the HoxB13 KO wound, the collagen aggregation is looser and more reticulate, resembling that of unwounded skin, indicating that collagen remodeling in HoxB13 KO wounds is reconstituting a more normal dermal architecture. Microarray analysis of gene expression in adult WT and HoxB13 KO whole skin revealed that the expression levels of several epidermal differentiation markers were significantly reduced in unwounded HoxB13 KO adult skin compared with unwounded WT adult skin. Studies on Hoxb 13 KO mouse wound healing further confirmed Hoxb 13 as a potential target for improvement of scarless wound healing (29-31).

Other Factors Involved in the Skin Wound Healing Process

The fetal response to cutaneous injury differs markedly from that of the adult, proceeding with only minimal inflammation, minimal fibroblast proliferation, and only essential collagen deposition. The effect of platelet-derived growth factor (PDGF) on both cellular and extracellular matrix events at a fetal wound site has been investigated because PDGF is known to play an important role in adult wound healing regulation. SILASTIC wound implants were harvested after either 1, 3, or 5 days in utero. The specimens underwent standard histological processing and were evaluated. PDGF-treated implants had a marked increase in acute inflammation, fibroblast recruitment, and collagen and hyaluronic acid deposition. These differences appeared to be largely time- and PDGF dose-dependent, and the data suggest that fetal repair proceeds in the absence of PDGF.

A key feature of scarless fetal healing appears to be a lack of inflammation in response to the wounding event. In contrast, the early phases of wound healing in late fetal and adult skin are characterized by a robust inflammatory response, and eventually a permanent scar in the wound area. While the interleukins IL-6 and IL-8 have been studied in fetal wound repair, the role of other classic inflammatory mediators in scarless healing is not known. Smad3 protein is involved in mediating intracellular signaling by members of the transforming growth factor-beta superfamily and plays a critical role in the cellular proliferation, differentiation, migration, and elaboration of matrix pivotal to cutaneous wound healing. Cross-talk between Smad3 and hormone signaling in vitro has been suggested as an important control mechanism regulating cell activities; however, its relevance in vivo is unknown. Ashcroft G S et al. reported that Smad3 plays a role in androgen-mediated inhibition of wound healing but not in the responses to estrogen modulation in vivo. Both wild-type and Smad3 null female mice exhibited delayed healing following ovariectomy, which could be reversed by estrogen replacement. By contrast, castration accelerated healing in wild-type male mice and was reversible by exogenous androgen treatment. Intriguingly, modulation of androgen levels resulted in no discernible perturbation in the healing response in the Smad3 null mice. Mutant monocytes could be lipopolysaccharide stimulated to produce specific pro-inflammatory agents (macrophage monocyte inhibitory factor) in a fashion similar to wild-type cells, but exhibited a muted response to androgen-mediated stimulation while maintaining a normal response to estrogen-induced macrophage inhibitory factor inhibition. These data suggest that Smad3 plays a role in mediating androgen signaling during the normal wound healing response and implicate Smad3 in the modulation of inflammatory cell activity by androgens.

Fibronectin (FN) is a multi-functional, adhesion protein and involved in multi-steps of the wound healing process. Strong evidence suggests that FN protein diversity is controlled by alternative RNA splicing; a coordinated transcription and RNA processing that is development-, age-, and tissue/cell type-regulated. Expression, regulation, and biological function of the FN gene and various spliced forms in this model are unknown. Airway and skin incisional wounds were made in fetal (gestation days 21-23), weanling (4-6 weeks) and adult (>6 months) rabbits. Expression profiles were obtained using mRNA differential display and cDNAs of interest were cloned, sequenced and validated by real-time PCR. The increased levels of both Fn1 and Sfrs3 transcripts were sustained up to 48 h in weanling airway mucosal wounds. The augmentations of the two genes in postnatal airway mucosal wounds were more prominent than that in skin wounds, indicating that the involvement of Sfrs3 and Fn1 genes in postnatal airway mucosal wounds is tissue-specific. There is evidence that SRp20 is indeed involved in the alternative splicing of FN and that the embryonic FN variants reappear during adult wound healing. A connection between the enhanced molecular activity of Sfrs3 and the regulation of the FN gene expression through alternative splicing during the early events of postnatal airway mucosal wound repair was proposed.

Multi-Targeted siRNA Compositions

RNA interference (RNAi) is a sequence-specific RNA degradation process that provides a relatively easy and direct way to knockdown, or silence, theoretically any gene (33, 34). In naturally occurring RNA interference, a double stranded RNA is cleaved by an RNase III/helicase protein, Dicer, into small interfering RNA (siRNA) molecules, a dsRNA of 19-23 nucleotides (nt) with 2-nt overhangs at the 3' ends. These siRNAs are incorporated into a multicomponent-ribonuclease called RNA-induced-silencing-complex (RISC). One strand of siRNA remains associated with RISC, and guides the complex towards a cognate RNA that has sequence complementary to the guider ss-siRNA in RISC. This siRNA-directed endonuclease digests the RNA, thereby inactivating it. Studies have revealed that the use of chemically synthesized 21-25-nt siRNAs exhibit RNAi effects in mammalian cells, and the thermodynamic stability of siRNA hybridization (at terminals or in the middle) plays a central role in determining the molecule's function (33, 36, 37).

Importantly, it is presently not possible to predict with a high degree of confidence which of many possible candidate siRNA sequences potentially targeting a mRNA sequence of a disease gene in fact exhibit effective RNAi activity. Instead, individually specific candidate siRNA polynucleotide or oligonucleotide sequences must be generated and tested in the mammalian cell culture to determine whether the intended interference with expression of a targeted gene has occurred. The unique advantage of siRNA makes it possible to be combined with multiple siRNA duplexes to target multiple disease causing genes in the same treatment, since all siRNA duplexes are chemically homogenous with same source of origin and same manufacturing process (33, 36-40).

In summary, the molecular targets involved in scarless wound healing of adult skin are well defined and evaluated. However, there is a pressing need to provide potent siRNA duplexes targeting the pro-inflammatory factor TGF-β, inflammation promoter COX-2 and differentiation regulator HoxB13 There further is a need to formulate such siRNA duplexes into multi-targeted siRNA compositions. There further remains a need to provide a therapeutic approach to improve the healing results of patients suffering cutaneous wounds caused by injury and many diseases. Thus, there is a strong need for multi-targeted RNAi therapeutics in the treatment of wound healing for use in patients suffering from various skin conditions.

SUMMARY

The invention relates to siRNA molecules for use in treating skin wounds. The invention provides a small interfering RNA (siRNA) molecule comprising a double stranded (duplex) oligonucleotide, wherein the oligonucleotide targets a complementary nucleotide sequence in a single stranded (ss) target RNA molecule. The ss target RNA target molecule is an mRNA encoding at least part of a peptide or protein whose activity promotes inflammation, wound healing, or scar formation in skin tissue, or it is a micro RNA (miRNA) functioning as a regulatory molecule whose activity promotes inflammation, wound healing, or scar formation in skin tissue.

The molecules are added to a pharmaceutically acceptable carrier to provide compositions for administering to a subject. In one embodiment, the composition comprises a pharmaceutically acceptable carrier and at least three siRNA molecules, wherein each siRNA molecule binds an mRNA molecule that encodes a gene selected from the group consisting of pro-inflammatory pathway genes, pro-angiogenesis pathway genes, and pro-cell proliferation pathway genes.

The invention also provides a method for treating a dermal or epidermal wound in a subject, wherein the wound is characterized at least in part by inflammation and neovascularization. The method comprises administering to the subject a composition comprising at least one siRNA molecule of the invention and a pharmaceutically acceptable carrier, wherein the molecule inhibits expression of at least one gene that promotes pathological or undesired processes in the healing of the wound.

The methods and compositions of this invention are useful for improvement of skin wound healing and other skin conditions.

BRIEF DESCRIPTION OF THE FIGURES

FIG. 1. Hematoxylin and Eosin staining of wild type lip and back skin.

FIG. 2. Collagen organization in WT and Hoxb13 KO wound biopsies.

FIG. 3. Scratch wound assays using primary dermal fibroblast isolated from WT and Hoxb13 KO mice.

FIG. 4. Reduced proliferation rate in HOXB13 expressing rat epithelial keratinocyte (REK).

FIG. 5. Overexpression of HOXB13 results in aberrant differentiation in day 5 lifted culture.

FIG. 6. GFP-HOXB13 protein is localized to the nucleus in REK and 293 cells (human epithelial cells).

FIG. 7. A. Locations of targeted sequences on mouse VEGF, VEGFR1, and VEGFR2 mRNAs. B. Measurements of mRNA knockdown after siRNA transfection in vitro.

FIG. 8. Local delivery of siRNAs targeting VEGF pathway genes inhibits the CpG ODN-induced angiogenesis.

FIG. 9. Raf-1 siRNA inhibits tumor growth in vivo after HK polymer mediated intratumoral delivery.

FIG. 10. Detection of sequences of all three mRNA species in PC3 cell total RNA samples.

FIG. 11. TGF-beta-1 siRNA is able to significantly knock down targeted gene expression in the PC3 cell.

FIG. 12. Cox1 siRNA is able to significantly knock down targeted gene expression in the PC3 cell.

FIG. 13. Hoxb13 siRNA is able to significantly knock down targeted gene expression in the PC3 cell.

DESCRIPTION OF THE INVENTION

Figure 14:
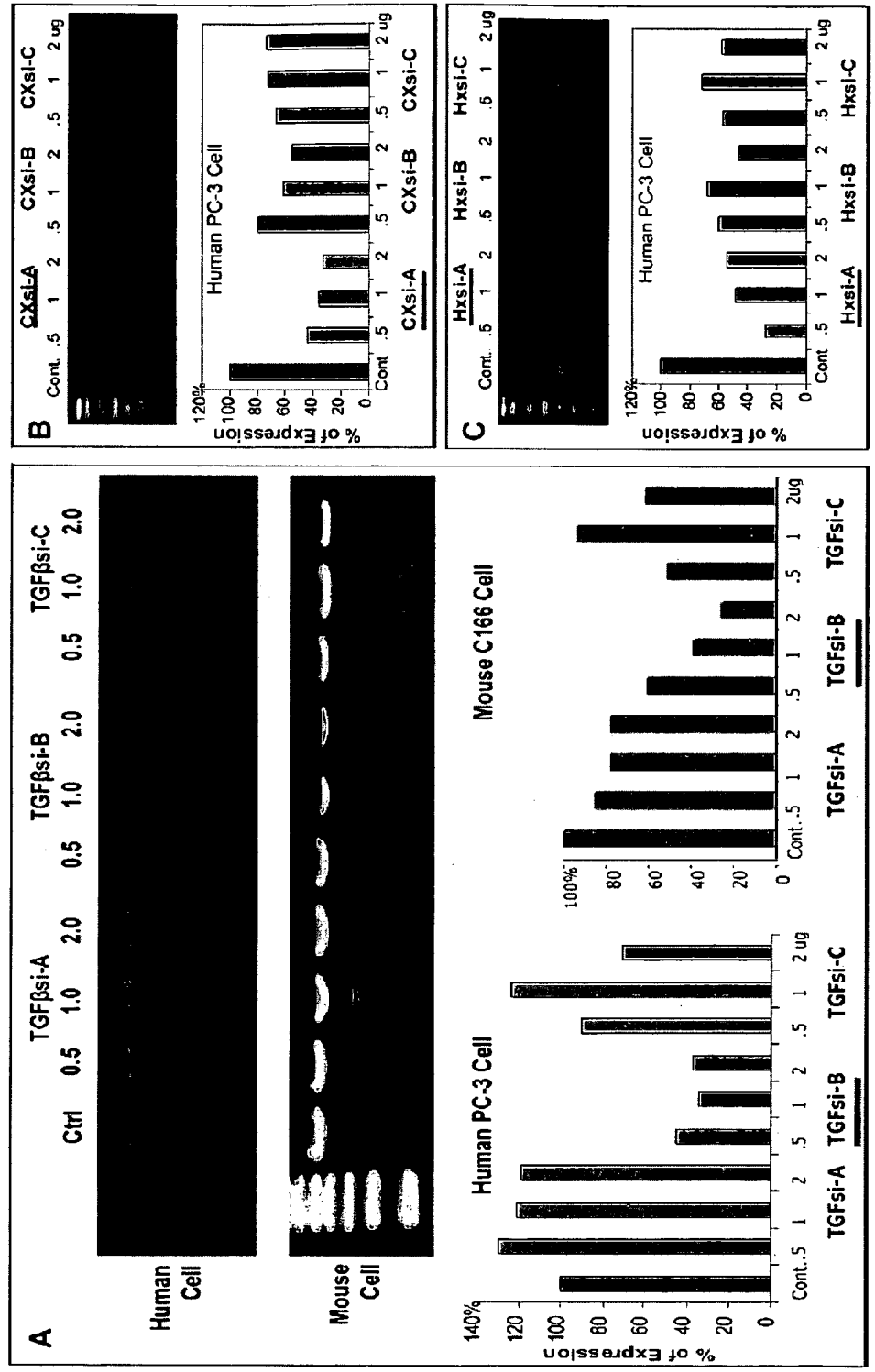
FIG. 14. RT-PCR analyses for selection of potent siRNA oligos. The silencing activities of three siRNA oligos targeting the corresponding gene were demonstrated through gel electrophoresis analyses. A. Potent siRNA oligo TGFsi-β targeting TGF-β was identified based on silencing activities in both human and mouse cells. B. Potent siRNA oligo CXsi-A targeting Cox-2 was identified based on silencing activity in human cell. C. Potent siRNA oligo Hxsi-A targeting Hoxb13 was identified based on silencing activity in human cell.

The present invention relates to various siRNA molecules, compositions containing the molecules, and their methods of use, which are directed to promoting wound healing in skin.

The invention provides a small interfering RNA (siRNA) molecule comprising a double stranded (duplex) oligonucleotide, wherein the oligonucleotide targets a complementary nucleotide sequence in a single stranded (ss) target RNA molecule. The ss target RNA target molecule is an mRNA encoding at least part of a peptide or protein whose activity promotes inflammation, wound healing, or scar formation in skin tissue, or it is a micro RNA (miRNA) functioning as a regulatory molecule whose activity promotes inflammation, wound healing, or scar formation in skin tissue. In one embodiment, a target mRNA molecule encodes a gene selected from the group of pro-inflammatory pathway genes, pro-angiogenesis pathway genes, and pro-cell proliferation pathway genes. Preferably, the genes are Hoxb13, TGF-β1, TGF-β2, or Cox-2. In another embodiment, the siRNA sequences are prepared in such way that each duplex can target and inhibit the same gene from, at least, both human and mouse, or non-human primates. In certain embodiments, an siRNA molecule binds to an mRNA molecule that encodes at least one protein. In further embodiments, an siRNA molecule binds to a mRNA molecule encodes at least one human protein. In still additional embodiments, an siRNA molecule binds to human mRNA molecule and to a homologous mouse mRNA molecule, i.e., mRNAs in the respective species that encode the same or similar protein. In various embodiments, the siRNA molecule are constructed with reference to the target mRNA coding sequences listed in Tables 2-9.

In one embodiment, the siRNA molecule has a length of 19-27 base pairs. The molecule can have blunt ends at both ends, or sticky ends at both ends, or one of each. The siRNA molecule may include a chemical modification at the individual nucleotide level or at the oligonucleotide backbone level, or it may have no modifications.

The molecules are added to a pharmaceutically acceptable carrier to provide compositions for administering to a subject. Preferably, the subject is a human.

In one embodiment, the composition comprises a pharmaceutically acceptable carrier and at least three siRNA molecules, wherein each siRNA molecule binds an mRNA molecule that encodes a gene selected from the group consisting of pro-inflammatory pathway genes, pro-angiogenesis pathway genes, and pro-cell proliferation pathway genes. In still another embodiment, each siRNA cocktail contains at least three siRNA duplexes that target at least three different gene sequences. Preferably, each gene is selected from a different pathway. A composition that is a mixture of siRNA molecules may be termed a "cocktail."

In several embodiments of a cocktail having at least three siRNA molecules, a cocktail mixture is chosen from a mixture listed in Tables A, B, C, or D. One particular embodiment is disclosed in Table A, wherein an siRNA (sense: 5'-caaggauaucgaaggcuugcuggga-3' (SEQ ID NO: 1), antisense: 5'-ucccagcaagccuucgauauccuug-3' (SEQ ID NO: 2)) binds to mRNA molecules that encode both human and mouse HoxB13 protein, an siRNA molecule (sense: 5'-gucuuuggu-cuggugccuggucuga-3' (SEQ ID NO: 3), antisense: 5'-ucagac-caggcaccagaccaaagac-3' (SEQ ID NO: 4)) binds to mRNA molecules that encode both human and mouse COX-2 protein, and an siRNA molecule (sense: 5'-ccccggaggugauuuc-caucuacaa-3' (SEQ ID NO: 5), antisense: 5'-uuguagaug-gaaaucaccuccgggg-3' (SEQ ID NO: 6)) binds to mRNA molecules that encode both human and mouse TGF-β1. In further particular embodiments disclosed in Table A, an siRNA (sense: 5'-GGUGGCUGGAACAGCCAGAUGU-GUU-3' (SEQ ID NO: 7), antisense: 5'-AACACAUCUG-GCUGUUCCAGCCACC-3' (SEQ ID NO: 8)) targets an mRNA molecule that encodes human and mouse both Hoxb13 protein, at least one siRNA molecule (sense: 5'-GGUCUGGUGCCUGGUCUGAUGAUGU-3' (SEQ ID NO: 9), antisense: 5'-ACAUCAUCAGACCAGGCACCA-GACC-3' (SEQ ID NO: 10)) targets an mRNA molecule that encodes both human and mouse Cox-2 protein, and at least one siRNA molecule (sense: 5'-CCCAAGGGCUAC-CAUGCCAACUUCU-3' (SEQ ID NO: 11), antisense: 5'-AGAAGUUGGCAUGGUAGCCCUUGGG-3' (SEQ ID NO: 12)) targets an mRNA molecule that encodes both human and mouse TGF-β1.

In other particular embodiments disclosed in Table C, an siRNA (sense: 5'-caaggauaucgaaggcuugcuggga-3' (SEQ ID NO: 1), antisense: 5'-ucccagcaagccuucgauauccuug-3' (SEQ ID NO: 2)) binds to mRNA molecules that encode both human and mouse HoxB13 protein, an siRNA molecule (sense: 5'-ggucuggugccuggucugaugaugu-3' (SEQ ID NO: 9), antisense: 5'-acaucaucagaccaggcaccagacc-3' (SEQ ID NO: 10)) binds to mRNA molecules that encode both human and mouse COX-2 protein, an siRNA molecule (5'-cacgagc-ccaagggcuaccaugcca-3' (SEQ ID NO: 13), antisense: 5'-ug-gcauggauagcccuugggcucgug-3' (SEQ ID NO: 14)) binds to mRNA molecules that encode both human and mouse TGF-β1 protein, and an siRNA molecule (sense: 5'-ccggagguga-uuuccaucuacaaca-3' (SEQ ID NO: 15), and antisense: 5'-ug-uuguagauggaaaucaccuccgg-3' (SEQ ID NO: 16)) binds to mRNA molecules that encode both human and mouse TGF-β2 protein.

In further embodiments, the mRNA molecules encode one or more HoxB13 pathway genes, COX-2 pathway genes, TGF-beta pathway genes, or a combination thereof. In still additional embodiments, the mRNA molecules encode one or more pro-angiogenesis genes, pro-inflammatory genes, or a combination thereof, and in yet further embodiments the mRNA molecules encode one or more pro-inflammation genes, or a combination thereof. In further embodiments of the cocktail, at least three siRNA molecules therein bind to at least two or more different mRNA molecules.

In still additional embodiments, the mixture of siRNA molecules is selected from mixtures presented in Tables E-H.

In yet additional embodiments, the siRNA cocktail inhibits expression of at least one gene selected from the group consisting of a pro-inflammatory pathway gene, a pro-angiogenesis pathway gene, and a pro-cell proliferation pathway gene. In particular embodiments, the siRNA cocktail inhibits expression of multiple genes. In additional embodiments, the siRNA cocktail contains sequences that target those listed in Tables 2, 3, 4 and 5 and that inhibit expression of HoxB13, TGF-beta1, TGF-beta2, and COX-2 in both human and mouse cells. In yet further embodiments, the siRNA cocktail contains sequences presented in Tables 6, 7, and 9 that inhibit expression of PDGFa, VEGFA FGF-2, and Lamin B1 proteins in both human and mouse cells.

In still further embodiments, the siRNA cocktail contains at least three siRNA duplexes at a 1:1:1 ratio, or 1:1.5:0.5 ratio, or 0.5:0.5:2 ratio, or other ratios according to the potency of each siRNA duplex and therapeutic requirements for the application.

The invention further provides pharmaceutically effective carriers for enhancing the siRNA cocktail delivery into the disease tissues and cells.

In various embodiments of the composition, the carrier comprises one or more components selected from the group consisting of a saline solution, a sugar solution, a polymer, a lipid, a cream, a gel, and a micellar material. Further components or carriers include a polycationic binding agent, cationic lipid, cationic micelle, cationic polypeptide, hydrophilic polymer grafted polymer, non-natural cationic polymer, cationic polyacetal, hydrophilic polymer grafted polyacetal, ligand functionalized cationic polymer, and ligand functionalized-hydrophilic polymer grafted polymer, biodegradable polyesters, such as poly(lactic acid) (PLA), poly(glycolic acid) (PGA), and poly(lactic-co-glycolic acid) (PLGA), PEG-PEI (polyethylene glycol and polyethylene imine), Poly-Spermine (Spermidine), and polyamidoamine (PAMAM) dendrimers. In further embodiments of the composition, the carrier is a histidine-lysine copolymer that is believed to form a nanoparticle containing an siRNA molecule, wherein the nanoparticle has a size of about 100-400 nm in diameter formulated with Methylcellulose gel for topical administration.

The siRNA molecules may be identified by the following steps: 1) creating a collection of siRNA duplexes designed to target a complementary nucleotide sequence in the ss target RNA molecule, wherein the targeting strands of said siRNA molecules comprise various sequences of nucleotides; 2) selecting the siRNA molecules that show the highest desired effect against said target molecules in vitro; 3) evaluating the selected siRNA molecules in an animal wound model; and 4) selecting the siRNA molecules that show the greatest efficacy in the model. A pharmaceutically acceptable carrier may be added to each of the siRNA molecules selected by step (2) to form pharmaceutical compositions, each of which is evaluated in the animal wound model. Preferably, the animal wound model is a lip excisional wound model in a Hoxb13 knockout mouse or a back excisional wound model in a Hoxb13 knockout mouse. More preferably, the siRNA molecules are evaluated in both animal models. Since the targeted genes may express in different cell types in the disease tissues, the efficacy of the particular siRNA cocktail is tested and confirmed not only in the cell culture but also in animal disease models. Preferably, the components of the siRNA cocktail are selected so that the therapeutic benefit of the cocktail is better than the therapeutic benefit of a single siRNA component by itself.

The invention also provides methods to prepare the proper ratio of each duplex in order to allow the siRNA cocktail to achieve the most potent synergistic effect. In one embodiment, the ratio is determined by determining the expression level of the target sequence compared to that of the control sequence. A higher expressing target sequence will require a higher ratio of the corresponding siRNA molecules.

The invention also provides a method for treating a dermal or epidermal wound in a subject. The wound may be caused by physical injury, a burn, an allergy, diabetic disease, inflammation, or a tumor. The wound may be characterized at least in part by inflammation and neovascularization. The method comprises administering to the subject a composition comprising at least one siRNA molecule of the invention and a pharmaceutically acceptable carrier, wherein the molecule inhibits expression of at least one gene that promotes pathological or undesired processes in the healing of the wound. The composition may be applied in a salve, spray, transdermal patch, or other ways known to those skilled in the art.

Successful siRNA-mediated therapy not only depends on identification of the targets and sequence of active siRNA molecules, but also on efficient in vivo delivery to the target tissues and into the cytoplasm (41-43). The routes of delivery of siRNA cocktail formulation for treatment of skin wound healing should be local and topical with appropriate clinically validated carriers. In addition to using imiquimod 5% cream as a carrier for siRNA cocktail topical application, three polymer-based carriers, including histidine-lysine polymers (HKP) (44), pegylated PEI (45) and PAMAM dendrimer (46) are particularly useful carriers.

The siRNA cocktail inhibits expression of a pro-angiogenesis gene, a pro-inflammatory gene, a gene that promotes scar formation, or a combination thereof. In still further embodiments of this method, an siRNA is employed against target sequences presented in Tables 2-9. In yet additional embodiments of this method, a cocktail employed in the method is one of the mixtures of siRNA molecules disclosed in Tables A-H.

EXAMPLES

Example 1

Lip Surgery Model for Wound Healing Analysis

There are results from previous studies showing that back skin wounds in HoxB13 KO mice healed with reduced scarring. The possible differences between back and lip skin raised the question whether lip wound in the KO mice would heal with reduced scar formation since muscle and fat layers of lip skin tissue are much less organized than that of upper dorsal back skin. We first compared the structure of the back and lip regions. Unlike the back skin structure, the muscle and fat layers of the lip region are not organized into distinct layers (FIG. 1). It was unclear whether the altered structure in the lip region would influence the wound healing process. To reveal the potential of using the mouse lip surgery model to study wound healing process, we have established a mouse lip surgery model to mimic cleft lip and palate surgery. Under general anesthesia and sterile conditions, HoxB13 KO and WT adult mice (8-16 week old) were given a single 0.5 cm full thickness skin incisional wound in parallel with their front teeth followed by suturing (6.0 Nylon) the wound, mimicking the cleft lip and palate surgery. 10% sterile India ink was administrated so the wound can be traced. Each animal was housed individually after the surgery. Lip wound biopsies were harvested for histological, immuno-histological and gene expression analysis at each desired time point. The expression of HoxB13 was confirmed in the mouse lip skin by RT-PCR with total RNA samples isolated from WT mouse lip skin tissue. Reverse transcription was carried out using a Bio-Rad iScript cDNA synthesis kit. PCR was performed with the forward primer, 5'-CTCCAGCTCCTGTGCCTTAT-3' (SEQ ID NO: 17) and the reverse primer, 5'-ACTGGCCAT-AGGCTGGTATG-3' (SEQ ID NO: 18). The HoxB13 product was detected and confirmed by sequencing (Seq Wright Inc).

Example 2

HoxB13 KO Mice Display Improved Wound Healing and Reduced Scar Formation

Following the establishment of the lip wound model, HoxB13 KO mice (kindly provided by Dr. Mario R. Capecchi) were subjected to the identical surgeries. The KO mice were back crossed with WT, C57BL6 mice for at least 10 generations to ensure that WT and KO mice have the same genetic background. Lip incisional wound biopsies were harvested from day 20, 30 and 60 wounds, and the collagen organization was determined by Masson Trichrome collagen staining (FIG. 2). Day 20 (B-Day20) and 30 (B-Day30) wounds showed more dense collagen staining and greater wound contractions in WT than in HoxB13 KO mice. In fact, the collagen contraction in wild type mice was so strong that we could not focus on the contracted collagen and surrounding collagen simultaneously in day 20 and day 30 wounds. At day 60, WT collagen is dense but the contraction is not as pronounced as day 20 and day 30 wounds. In contrast, HoxB13 KO mice displayed loose collagen organization at day 20, day 30 and day 60 wound biopsies, suggesting reduced scar formation in the lip region of the knockout mice, consistent with what was observed in the upper dorsal back.

Example 3

HoxB13 Knockout Fibroblasts Displayed a Reduced Proliferation Rate and Migration Activity We next compared WT and KO mouse primary fibroblast activity in vitro. Primary dermal fibroblasts were prepared from 3 day old newborn mice. Mice were euthanized by cervical dislocation and sterilized with 70% ethanol. Skin was harvested and soaked in PBS with 20 μg/ml gentamicin for 45 minutes. The skin was then floated in 25 unit/ml dispase solution (Sigma) overnight at 4° C. The epidermal layer was separated from the dermal layer using a fine tip forceps. The epidermal layer was further processed to isolate keratinocytes. The dermal layer was further processed in 100 unit/ml crude collagenase (Sigma) at 37° C. for one hour. After filtration through cell strainers (Falcon, 70 uM), cells were plated in tissue culture dishes in DMEM high glucose with 10% FBS and subcultured twice prior to being used for assays. For the proliferation assay, cells were seeded at 5000/well in 96 well plates. MTT further assays were performed daily (Molecular Probes, CA) and demonstrated reduced proliferation activity of HoxB13 knockout fibroblasts. This result was confirmed by a manual cell counting method using a hemocytometer (data not shown). It has been reported that HOXB13 is an inhibitor of neuronal cell proliferation activator of apoptotic pathways (Economides et al., 2003). Therefore, the proliferation rate of HoxB13 knockout fibroblasts was expected to be increased, which is in contrast with what we have observed. It is possible that roles of HoxB13 may be cell type specific. In fact, the over expression of HoxB13 has been correlated with prostate cancer and HoxB13 has been proposed to be a biomarker for prostate cancer (Edwards et al., 2005). In addition, we performed an in vitro scratch wound assay to mimic incisional wounds. For this assay, $2 \times 10^5$ primary dermal fibroblasts per well were seeded into six well plates, that were pre-coated with collagen type I, type IV or fibronectin. The cells were then incubated in DMEM high glucose with 0.2% FBS for 24 hours. Then a 1 ml Pipetman™ tip was used to scratch the cell monolayer to create a gap. The percentage of the gap closed after 4 hour and 24 hour incubation in DMEM/0.2% FBS was measured using Olympus Microsuite software. Platelet-derived growth factor B (10 ng/ml) was added to monitor its effect on migration of WT and KO fibroblasts. As demonstrated in FIG. 3, HoxB13 KO fibroblasts exhibited slower migration rate than WT fibroblasts in the absence of PDGF on collagen type I, type IV and fibronectin coated surface at 4 h post-wounding. Additionally, HoxB13 KO fibroblasts were responsive to PDGF stimulation. At 24 hour post-wounding, the difference in migration activity was not as pronounced.

Example 4

Overexpression of HoxB13 Inhibits Proliferation and Promotes Terminal Differentiation When Rat Epithelial Keratinocytes (REK) cells were raised to air liquid interface as described (Tammi et al. 2000), REK cells differentiate to all layers of epidermis. Using this as an in vitro keratinocyte differentiation model, we investigated the effect of HOXB13 on REK stratification. REK cell clones expressing HOXB13 were obtained by retroviral transduction and clonal selection. HoxB13 cDNA was subcloned into the MLV vector under the control of a CMV promoter. The retroviral particles were produced by three plasmid co-transfection (Li et al., 2001). REK cells were transduced by the retroviral particles with HoxB13 or vector only at MOI~10 and selected in 2 μg/ml puromycin (Note: 1 μg/ml puromycin is sufficient to kill all un-transduced cells). The puromycin resistant cells were seeded into three 96-well-dishes at one cell per well density. After two week's incubation, the cells in each well were visualized and individual clones were transferred, expanded and maintained in 1 μg/ml puromycin. The expression of HoxB13 or vector was confirmed by RT-PCR using one primer located in the vector and the other primer located in HoxB13 cDNA. REK cell expressing HoxB13 displayed reduced proliferation rate when compared with REK transduced with vector only using the MTT assay (FIG. 4). Overexpression of HoxB13 in REK resulted in excessive terminal differentiation when these REK cells were raised to air liquid interface (FIG. 5). This result was reproduced with two additional REK-HoxB13 clones. In conclusion, overexpression of HOXB13 affects keratinocyte cells' proliferation and stratification.

Example 5

HOXB13 is a Nuclear Protein

In order to determine subcellular location of HoxB13, a green fluorescent protein, GFP-HoxB13 fusion protein was generated by the removal of the termination codon of GFP and initiation codon of HoxB13. GFP-HoxB13 expression was driven by a CMV promoter. The plasmid containing GFP-HoxB13 cDNA was transfected into REK or 293T human kidney epithelial cells using Lipofectamine (Invitrogen, CA) and the expression of GFP was monitored under a fluorescent microscope at 24 hour post transfection. In contrast to a previous report that HoxB13 expression is cytoplasmic during fetal skin development (Komuves et al., 2003), we have found that the GFP-HxoB13 is localized to the nucleus, suggesting that HOXB13 is a nuclear protein (FIG. 6). The nuclear localization of HoxB13 makes it very difficult to be accessible by small molecule inhibitors and monoclonal antibody inhibitors. Therefore, application of siRNA inhibitor to silence its expression through mRNA degradation in the cytoplasm provides a logical therapeutic approach.

Example 6

Identify Potent siRNA Duplexes to Compose Multi-Targeted siRNA Cocktail

Double-stranded siRNAs were prepared to target the VEGF-pathway factors: mVEGF-A (XM_192823), mVEGFR1 (D88689), and mVEGFR-2 (MN_010612). Two target sequences were picked up from each gene. These sequences are (from 5' to 3'): mVEGF-A (1. AAGCCGUC-CUGUGUGCCGCUG (SEQ ID NO: 19); 2. AAC-GAUGAAGCCCUGGAGUGC (SEQ ID NO: 20)); mVEGFR1 (1. AAGUUAAAAGUGCCUGAACUG (SEQ ID NO: 21); 2. AAGCAGGCCAGACUCUCUUUC (SEQ ID NO: 22)); mVEGFR2 (1. AAGCUCAGCACACAGAAA-GAC (SEQ ID NO: 23); 2. AAUGCGGCGGUGGUGA-CAGUA (SEQ ID NO: 24)). As for unrelated controls, two siRNA sequences from firefly luciferase (Luc, AF434924) were selected as Luc (1. AAGCUAUGAAACGAUAUGGGC (SEQ ID NO: 25); 2. AACCGCUGGAGAGCAACUGCA (SEQ ID NO: 26)). Blast sequence searching confirmed the specificity of these siRNAs with their targeted sequences, and the mVEGF-A targets were designed to be shared by different mVEGF-A isomers. All siRNAs were custom-prepared as 21-nt double stranded RNA oligonucleotides with 19-nt duplex in the middle and dTdT overhang at the 3'-end of either RNA strand, synthesized by Qiagen. To get better RNAi effect, we routinely used a mixture of two double-stranded 21-nucleotide RNA duplexes targeting two different sequences on a single mRNA molecule. The RT-PCR was performed for detection of mRNA knockdown by siRNAs in vitro. Cytoplasmic RNA was isolated by RNAwiz (Ambion, #9736) according to manufacturer's instruction with additional DNAse treatment, and subjected to RT-PCR with specially prepared primers. The mRNA-specific reverse primers for the RT reaction were all 47-mer oligonucleotides with the 5'-end 30-mer of unique sequence (called "TS1" sequence, indicated in uppercase below) linked to a 17-mer sequence unique for each mRNA molecule (in lower case below). They were (from 5' to 3'): 1) mVEGFA Dn: GAACATCGATGA-CAAGCTTAGGTATCGATAcaagctgcctcgccttg (SEQ ID NO: 27); 2): mVEGFR1 Dn: GAACATCGATGACAAGCT-TAGGTATCGATAtagattgaagattccgc (SEQ ID NO: 28); 3) mVEGFR2 Dn: GAACATCGATGACAAGCTTAGGTATC-GATaggtcactgaca gaggcg (SEQ ID NO: 29). The PCR assays for all the tested genes, that follow the RT assay, used a same reverse primer, TS1: GAACATCGATGACAAGCTTAGG-TATCGATA (SEQ ID NO: 30). However, the forward primers for PCR, all were 30-mer oligonucleotides, unique for each gene: VEGFA Up: GATGTCTACCAGCGAAGCTACTGC-CGTCCG (SEQ ID NO: 31); 2) mVEGFR1 Up: GTCAGCT-GCTGGGACACCGCGGTCTTGCCT (SEQ ID NO: 32); 3) mVEGFR2 Up: GGCGCTGCTAGCTGTCGCTCTGTGGT TCTG (SEQ ID NO: 33). The RT-PCR of housekeeping gene GAPDH was used as control for RNA amount used in RS-PCR. An oligonucleotide dT primer (19-mer) was used for RT assay of GAPDH. The primers used for the followed PCR were 20-mer oligonucleotides: 1) GAPDH Up: CCTGGT-CACCAGGGCTGCTT (SEQ ID NO: 34); 2) GAPDH Dn: CCAGCCTTCTCCATGGTGGT (SEQ ID NO: 35). RT-PCR was also used according to the protocol described previously. For the detection of mVEGF-A expression the primers used were 5'-GCGGGCTGCCTCGCAGTC-3' (SEQ ID NO: 36) (sense) and 5'-TCACCGCCTTGGCTTGTCAC-3' (SEQ ID NO: 37) (antisense). FIG. 7. shows that all three siRNA pairs are effectively knocking down the target gene expression. To evaluate the potency of the siRNA cocktail with three pairs of siRNA duplexes, we used an ocular neovascularization mouse model with histidine-lysine polymer nanoparticle mediated in vivo delivery.

Example 7

Inhibition of Angiogenesis by Local Delivery of siRNA Cocktail

A previous study demonstrated that CpG-containing oligonucleotide nucleotide encapsulated in hydron pellets induce dVEGF-mediated angiogenesis when inserted into corneal micropockets. This system was used to measure the inhibitory effect of local administration of siRNA preparations prepared to target VEGF as well as two of its receptors (VEGFR1 and VEGFR2). A single dose of 10 µg of siRNA in with histidine-lysine polymer nanoparticles was used in all cases. This was administered by subconjunctival injection 24 hours after the establishment of micropockets containing CpG ODN. The siRNAs were tested individually as well as a 1:1:1 mixture of all three (siVEGFA, siVEGFR1, and siVEGFR2). New blood vessel formation in the corneal limbus was monitored at both days 4 and 7 after pellet implantation. As shown in FIG. 8, significant inhibition of corneal neovascularization resulted with all three test siRNAs compared to those given control siLacZ at day 4 after pellet implantation ($P<0.05$). The combination of the three tested siRNAs was the most effective inhibitor, providing an 60% reduction in neovascularization ($P<0.01$). The local siRNA delivery was carried out with histidine-lysine polymer nanoparticles though subconjunctival administration. The synergistic benefit of the multi-targeted siRNA cocktail was demonstrated in this ocular angiogenesis model. The data provide strong support to the use of multi-targeted siRNA cocktails as disclosed herein to improve adult skin wound healing with less scar tissue formation and stronger tensile strength.

Example 8

Twenty-Five-mer siRNAs Targeting both Human and Mouse Genes 25 mer siRNA sequences are prepared that target homologous sequences of both human and mouse in the orthologous genes. For example, the siRNA duplex sequence targeting HoxB13 is able to target both human HoxB13 and mouse HoxB13 genes. Table 1 provides sequences identified for siRNA therapeutics (36-37). Each sequence targets both human and mouse corresponding gene. Therefore, the potent sequences defined from the mouse cells can be confirmed again using human cells. If the particular siRNA duplex is potent in both tests, the silencing activity revealed in the mouse animal model could be assumed to be active in human. Using this approach, we can address a general concern about the species specificity of this type of inhibitors, such as the monoclonal antibody, have encountered. In addition, for the therapeutic candidates of siRNA duplexes, the efficacy and toxicity data achieved from the study using mouse model can be easily translated into the human setting.

Example 9

HK Polymer Enhances Local siRNA Delivery

The HK polymer-siRNA nanoparticle mediated local delivery has achieved potent anti-angiogenic activity. In a separate study using HK polymer to enhance siRNA delivery intratumorally, the tumor growth curves have shown significant anti-tumor efficacy with clear down regulation of the target gene expression. At 10 days after the injection of MDA-MB-435 cells into the mammary fat pad, mice with visible tumors were separated into treatment groups. Each group had four mice with eight tumors and tumor size was assessed in two dimensions and calculated. Mice received 4 µg/tumor of siRNA with each intratumoral injection every 5 days. To confirm the antitumor efficacy of siRNA Raf-1 with the optimal polymer in greater detail, mice with tumors were divided into these groups: untreated, b-galactosidase siRNA and Raf-1 siRNA. As seen in FIG. 9, Raf-1 siRNA inhibits tumor growth in vivo after HK polymer mediated intratumoral delivery. Clearly, HK polymer has been validated as an effective local siRNA delivery carrier. This led us to conclude that HK polymer would facilitate the local siRNA delivery onto the skin wounds with the appropriate formulations.

Over the past few decades, biodegradable polyesters, such as poly(lactic acid) (PLA), poly(glycolic acid) (PGA), and poly(lactic-co-glycolic acid) (PLGA), have been extensively studied for a wide variety of pharmaceutical and biomedical applications. The biodegradable polyester family has been regarded as one of the few synthetic biodegradable polymers with controllable biodegradability, excellent biocompatibility, and high safety. The need for a variety of drug formulations for different drugs and delivery pathways resulted in development of various types of block copolymers (e.g., diblock, triblock, multiblock, and star-shaped block) consisting of the biodegradable polyesters and poly(ethylene glycol) (PEG).

PAMAM dendrimers represent an exciting new class of macromolecular architecture called "dense star" polymers. Unlike classical polymers, dendrimers have a high degree of molecular uniformity, narrow molecular weight distribution, specific size and shape characteristics, and a highly functionalized terminal surface. The manufacturing process is a series of repetitive steps starting with a central initiator core. Each subsequent growth step represents a new "generation" of polymer with a larger molecular diameter, twice the number of reactive surface sites, and approximately double the molecular weight of the preceding generation. Polyamidoamine (PAMAM) dendrimers are the most common class of dendrimers suitable for many materials science and biotechnology applications. PAMAM dendrimers consist of alkyldiamine core and tertiary amine branches.

Example 10 siRNA Cocktails Reduce Expression of Target Genes in Cultured Cells 1. siRNA duplexes prepared: Three sequences have been prepared for targeting each of the three mRNAs, with 25-mer blunt end:

```
hmHX-    sense    5'-r(GGUGGCUGGAACAGCCAGAUGUGUU)-3'
25-1:             (SEQ ID NO: 7)
         antisense 5'-r(AACACAUCUGGCUGUUCCAGCCACC)-3'
                  (SEQ ID NO: 8)

hmHX-    sense    5'-r(GCUGGAACAGCCAGAUGUGUUGCCA)-3'
25-2:             (SEQ ID NO: 38)
         antisense 5'-r(UGGCAACACAUCUGGCUGUUCCAGC)-3'
                  (SEQ ID NO: 39)

hmHX-    sense    5'-r(CGCCAGAUUACCAUCUGGUUUCAGA)-3'
25-3:             (SEQ ID NO: 40)
         antisense 5'-r(UCUGAAACCAGAUGGUAAUCUGGCG)-3'
                  (SEQ ID NO: 41)

hmTF-    sense    5'-r(GGAUCCACGAGCCCAAGGGCUACCA)-3'
25-1:             (SEQ ID NO: 42)
         antisense 5'-r(UGGUAGCCCUUGGGCUCGUGGAUCC)-3'
                  (SEQ ID NO: 43)

hmTF-    sense    5'-r(CCCAAGGGCUACCAUGCCAACUUCU)-3'
25-2:             (SEQ ID NO: 11)
         antisense 5'-r(AGAAGUUGGCAUGGUAGCCCUUGGG)-3'
                  (SEQ ID NO: 12)

hmTF-    sense    5'-r(GAGCCCAAGGGCUACCAUGCCAACU)-3'
25-3:             (SEQ ID NO: 44)
         antisense 5'-r(AGUUGGCAUGGUAGCCCUUGGGCUC)-3'
                  (SEQ ID NO: 45)

hmCX-    sense    5'-r(GGUCUGGUGCCUGGUCUGAUGAUGU)-3'
25-1:             (SEQ ID NO: 9)
         antisense 5'-r(ACAUCAUCAGACCAGGCACCAGACC)-3'
                  (SEQ ID NO: 10)

hmCX-    sense    5'-r(GAGCACCAUUCUCCUUGAAAGGACU)-3'
25-2:             (SEQ ID NO: 46)
         antisense 5'-r(AGUCCUUUCAAGGAGAAUGGUGCUC)-3'
                  (SEQ ID NO: 47)

hmCX-    sense    5'-r(CCUCAAUUCAGUCUCUCAUCUGCAA)-3'
25-3:             (SEQ ID NO: 48)
         antisense 5'-r(UUGCAGAUGAGAGACUGAAUUGAGG)-3'
                  (SEQ ID NO: 49)
```

2. Two control sequences were also prepared and used in the study:

```
Lu25-a:
sense        5'-r(GAGGAGCCUUCAGGAUUACAAGAUU)-3'
             (SEQ ID NO: 50)

antisense    5'-r(AAUCUUGUAAUCCUGAAGGCUCCUC)-3'
             (SEQ ID NO: 51)
```

```
GF25-a
sense        5'-r(GCUGACCCUGAAGUUCAUC)dTdT
             (SEQ ID NO: 52)

antisense    5'-r(GAUGAACUUCAGGGUCAGC)dTdT
             (SEQ ID NO: 53)
```

3. Six pairs of the PCR primers for Hoxb13, Cox-2 and TGF-beta1 cDNA sequence detection were also prepared and synthesized for both human and mouse sequences:

```
hHxup:    5'-GCCTCTCGGAGCGCCAGATT-3'
          (SEQ ID NO: 54)
hHxdn:    5'-CTAGTACTGGTTATCGTGAT-3'
          (SEQ ID NO: 55)

mHxup:    5'-CTCCAGCTCCTGTGCCTTAT-3'
          (SEQ ID NO: 17)
mHxdn:    5'-ACTGGCCATAGGCTGGTATG-3'
          (SEQ ID NO: 18)

hCxup:    5'-CGGGCTGGGCCATGGGGTGGA-3'
          (SEQ ID NO: 56)
hCxdn:    5'-CCTATCAGTATTAGCCTGCTT-3'
          (SEQ ID NO: 57)

mCxup:    5'-GGAAGCCTTCTCCAACCTCT-3'
          (SEQ ID NO: 58)
mCxdn:    5'-GGATACACCTCTCCACCAAT-3'
          (SEQ ID NO: 59)

hTGb2up:  5'-GAGTACTACGCCAAGGAGGTT-3'
          (SEQ ID NO: 60)
hTGb2dn:  5'-CCATTCATGAACAGCATCAGT-3'
          (SEQ ID NO: 61)

mTGb2up:  5'-CTACTGTGTGCTGAGCACCTT-3'
          (SEQ ID NO: 62)
mTGb2dn:  5'-CGCTGCTCGGCCACTCTGGCT-3'
          (SEQ ID NO: 63)
```

4. Human prostate carcinoma cell-PC3 was used for detection of the gene expression knockdown. A series of standard transfection experiments were carried out using the protocol provided by the vendor (Invitrogen) with the siRNA duplexes identified in step 2 accordingly.
5. Total RNA samples were isolated and subjected to RT-PCR analysis using the respective PCR primers identified in step 3 above. The results are shown in FIGS. 10, 11, 12, and 13. It is seen that, as detected by RT-PCR, expression of the targeted genes is significantly reduced when the corresponding targeting siRNA is transfected, whereas various control (i.e., nontargeting) siRNAs have no effect on expression.

Example 11

Potent siRNA Duplexes for Silencing TGF-β1, COX-2 and HoxB13 Expression in vitro Table 1 provides 10 siRNA sequences for each of the targeted gene, HoxB13, COX-2 and TGF-β.
Selection of Four siRNA Duplexes for Each Target Gene
The siRNA control sequence was selected targeting a non-related sequence and without homologue in both human and mouse. It is Lu25-a: (sense, 5'-GAGGAGCCUUCAGGA-UUACAAGAUU-3' (SEQ ID NO: 50) and antisense, 5'-AAUCUUGUAAUCCU GAAGGCUCCUC-3' (SEQ ID NO: 51)). The four siRNA sequences targeting both human and mouse HoxB13 are: hmHX-1: (sense, 5'-GGUGGCUG-GAACAGCCAGAUGUGUU-3' (SEQ ID NO: 7) and antisense, 5'-AACACAUCUGGCUGUUCCAGCCACC-3'

(SEQ ID NO: 8)); hmHX-2: (sense, 5'-GCUGGAACAGC-CAGAUGUGUUGCCA-3' (SEQ ID NO: J and antisense, 5'-UGGCAACACAUCUGGCUGUUCCAGC-3' (SEQ ID NO: 39)); hmHX-3: (sense, 5'-CGCCAGAUUACCAUCUG-GUUUCAGA-3' (SEQ ID NO: 40) and antisense, 5'-UCUGAAACCAGAUGGUAAUCUGGCG-3' (SEQ ID NO: 41)); and hmHX-4: (sense, 5'-CAAGGAUAUCGAAG-GCUUGCUGGGA-3' (SEQ ID NO: 1) and antisense, 5'-UC-CCAGCAAGCCUUCGAUAUCCUUG-3' (SEQ ID NO: 2)). The four siRNA sequences targeting both human and mouse COX-2 and they are: hmCX-1: (sense, 5'-GGUCUGGUGC-CUGGUCUGAUGAUGU-3' (SEQ ID NO: 9) and antisense, 5'-ACAUCAUCAGACCAGGCACCAGACC-3' (SEQ ID NO: 10)); hmCX-2: (sense, 5'-GAGCACCAUUCUCCU-UGAAAGGACU-3' (SEQ ID NO: 46) and antisense, 5'-AGUCCUUUCAAGGAGAAUGGUGCUC-3' (SEQ ID NO: 47)); hmCX-3: (sense, 5'-CCUCAAUU CAGUCUCU-CAUCUGCAA-3' (SEQ ID NO: 48) and antisense, 5'-UUG-CAGAUGAGAGACUGAAUUGAGG-3' (SEQ ID NO: 49)); and hmCX-4: (sense, 5'-GUCUUUGGUCUGGUGC-CUGGUCUGA-3' (SEQ ID NO: 3) and antisense, 5'-UCA-GACCAGGCACCAGACCAAAGAC-3' (SEQ ID NO: 4)). The four siRNA sequences targeting both human and mouse TGF-β1 and they are: hmTF-1: (sense, 5'-GGAUCCAC-GAGCCCAAGGGCUACCA-3' (SEQ ID NO: 42) and antisense, 5'-UGGUAGCCCUUGGGCUCGUGGAUCC-3' (SEQ ID NO: 43)); hmTF-2: (sense, 5'-CCCAAGGGCUAC-CAUGCCAACUUCU-3' (SEQ ID NO: 11) and antisense, 5'-AGAAGUUGGCAUGGUAGCCCUUGGG-3' (SEQ ID NO: 12)); hmTF-3: (sense, 5'-GAGCCCAAGGGCUAC-CAUGCCAACU-3' (SEQ ID NO: 44) and antisense, 5'-AG-UUGGCAUGGUAGCCCUUGGGCUC-3' (SEQ ID NO: 45)); and hmTF-4: (sense, 5'-CCCCGGAGGUGAUUUC-CAUCUACAA-3' (SEQ ID NO: 5) and antisense, 5'-UU-GUAGAUGGAAAUCACCUCCGGGG-3' (SEQ ID NO: 6)).

Transfection of siRNA Duplexes into the Specific Cell Cultures

For measuring HoxB13 gene expression knockdown at both mRNA and protein levels using four selected siRNA duplexes, the REK cell expressing HOXB13 were transfected by four siRNA duplexes with LipofectAmine 2000. Similarly, for measurement of COX-2 gene expression knockdown at both mRNA and protein levels using four selected siRNA duplexes, human foreskin fibroblasts (HFF) obtained from American Type Culture Collection (Manassas, Va.) are cultured on 10-cm plates in DMEM supplemented with 10% fetal bovine serum (FBS), 100 µg/ml streptomycin, and 100 U/ml penicillin and transfected with the siRNA duplexes using LipofectAmine 2000. The cells should be washed twice with PBS and incubated in FBS-free medium for 24 h. FBS-free medium was replaced with medium containing 10% FBS to initiate the cell cycle. For measuring TGF-β1 gene expression knockdown at both mRNA and protein levels using four selected siRNA duplexes, the mouse embryonic endothelial cells (MEECs) should be transfected with siRNA-LipofectAmine 2000 followed by RT-PCR analysis. Potential pitfalls: the transfection of those cells with LipofectAmine 2000 may not always works efficiently, the alternative transfection methods should be applied such as electroporation or other transfection agents. The efficient transfection and following RT-PCR analysis may need to work in concert to achieve satisfactory data.

Measurement of mRNA Levels Using RT-PCR

Total RNA from each of those transfected cell lines including HoxB13 (mouse) expressing REK cells, COX-2 (human) expressing cells and mouse embryonic endothelial cells are isolated and purified for RT-PCR analysis. For detection of HoxB13 amplicon (mouse), an RT reaction is followed with a PCR reaction using forward primer, 5'-CTCCAGCTCCTGT-GCCTTAT-3' (SEQ ID NO: 17) and the reverse primer, 5'-ACT GGCCATAGGCTGGTATG-3' (SEQ ID NO: 18). For detection of COX-2 amplicon (human), an RT reaction is followed with a PCR reaction using forward primer, 5'-CGGGCTGGGCCATGGGGTGGA-3' (SEQ ID NO: 56) and the reverse primer, 5% CCTATCAGTATTAGCCT-GCTT-3' (SEQ ID NO: 57). For detection of TGF-β1 amplicon (mouse), an RT reaction is followed with a PCR reaction using forward primer, 5'-CTACTGTGTGCTGAGCAC-CT'"T-3' (SEQ ID NO: 62) and the reverse primer, 5'-CGCT-GCTCGGCCACTCTGGCT-3' (SEQ ID NO: 63). The PCR products should be loaded on a 1% agarose gel and stained with ethidium bromide. The PCR product should exhibit the levels of the knockdown of each particular mRNA using the particular siRNA duplexes. The result from this experiment is to determine the potency of each siRNA duplex and provide the first look if a particular siRNA duplex should be the most potent one. The RT-PCR analysis is closely coordinated with the transfection experiment so that proper conditions are optimized for efficient transfection for particular cell line, in order to achieve sufficient amount of total RNA for the PCR analysis. In addition, the selection of the most potent siRNA duplex for each gene should be based on three repeated experiments.

Measurement of Protein Levels Using ELISA

To measure protein levels of the cells transfected with corresponding siRNA duplexes, the Western blot analysis and ELISA analysis should be sufficient and satisfactory. The cell lysates or cell culture media would be used for the protein detection. Although the ELISA assay for detection of mouse HoxB13 is not commercial available, we can use the a rat polyclonal antibody to mouse HoxB13 (Aviva Systems Biologics, San Diego, Calif.) to detect siRNA-mediated knockdown in the HoxB13 expressing REK cells with a Western blot analysis. Rabbit anti-Hoxb 13 antibody was generated against the N-terminal (amino acids 1-7 9) portion of mouse HoxB13. This antibody should recognize both the WT and knockout HoxB13 protein. The latter is a truncated protein that stops at amino acid 33 of the homeodomain. Before use, the antisera should be positively affinity purified followed by negative affinity purification against mouse Hoxc13 and chicken Hoxd13 to eliminate possible cross-reactivity with the other Hox13 proteins. Staining should be viewed using a Leica DMLB microscope, and images should be captured using an Optronics DEI750D Digital System (Goleta, Calif.). The human COX-2 is analyzed using COX-2 ELISA kit (Zymed, San Francisco, Calif.) which is an enzyme-linked immunosorbent sandwich assay for quantitative detection of human COX-2 in cell culture supernatants and cell lysates. Since Cyclooxygenase (COX) is a membrane-bound enzyme, which has a molecular weight of 71 kDa, the cell lysate should be prepared for the ELISA analysis. The mouse TGF-β1 is analyzed using Human/Mouse TGFb1 (Transforming Growth Factor beta 1, TGF-beta1, TGF-b1) ELISA Ready-SET-Go Kit (with Pre-Coated Plates). The selection of the most potent siRNA duplex for each gene should be based on three repeated experiments. The potential pitfall is that sometime the most potent siRNA duplex selected from the mRNA knockdown is not correlated with the one selected from the protein knockdown. When that situation happens, we should relay on the data from the mRNA level knockdown, since that it is the direct reflection of RNAi mechanism of action. The discrepancy of the protein level knockdown some time may be due to the non-specific or so call "off-target" effect, which is not the result of the RNAi mechanism of action.

Example 12

Selection of the most Efficacious siRNA Cocktail in vivo

After selection of the most potent siRNA duplex for each of the following three genes, HoxB13, COX-2 and TGF-β1 based on the cell culture studies, they are combined together as the siRNA cocktail with several ratios of the combinations can be used such as 1:1:1, 2:1:1 and 3:1:1, etc. Because of the importance of HoxB13 in the adult skin wound healing, an appropriate ratio change of the siRNA duplex specific to HoxB13 is determined.

The Mouse Model for Evaluation of Multi-Targeted siRNA Cocktail

In order to evaluate the appropriate siRNA cocktail and most suitable formulation, we have access to the HoxB13 knockout (KO) adult mouse. We found that HoxB13 KO wounds exhibit several characteristics of early gestational fetal wounds, including faster closure, increased tensile strength, and less dermal scarring when compared with wounds from their wild-type (WT) counterparts. Biochemical evaluation revealed that levels of epidermal and dermal HA are significantly higher in unwounded adult HoxB13 KO skin compared with WT skin. Based on these results, we postulated that HoxB13 in adult skin promotes differentiation, whereas its absence creates a more fetal-like environment, and that one consequence of this fetal-like state is enhanced wound healing. In addition to a well accepted model using the back skin wounds in HoxB13 KO mice, we have also established a mouse lip surgery model to mimic cleft lip and palate surgery, performed under general anesthesia and sterile conditions. HoxB13 KO and WT adult mice (8-16 week old) are given a single 0.5 cm full thickness skin incisional wound in parallel with their front teeth followed by suturing (6.0 Nylon) the wound, mimicking the cleft lip and palate surgery.

The Formulations Used for Delivery of the Multi-Targeted siRNA Cocktail

To establish a polymer-siRNA nanoparticle, we decided to first test the Histidine-Lysine branched polymer for this formulation. The biopolymer core facility at the University of Maryland synthesizes polymers on a Ranin Voyager synthesizer (PTI, Tucson, Ariz.). The branched HK polymer, effective for in vivo siRNA transfer, was complexed with siRNA duplexes for local administration. The polymer is purified by HPLC (Beckman, Fullerton, Calif.). The second branched H (histidine) and K (Lysine) polymers used in this study should be R-KR-KR-KR, where R=[HHHKHHHKHHHKHHH] 2KH4NH4]. H3K4b is a branched polymer with the same core and structure described above except the R branches differ: R=KHHHKHHHKHHHKHHHK (SEQ ID NO: 65). The HKP can be dissolved in aqueous solution and then mixed with siRNA aqueous solution at a ratio of 4:1 by mass, forming nanoparticles of average size of 150-200 nm in diameter. The HKP-siRNA aqueous solutions were semi-transparent without noticeable aggregation of precipitate, and can be stored at 4° C. for at least three months. In addition to HK polymers, we may also test two different types of polymer carriers, pegylated PEI and PAMAM dendrimer, with our siRNA cocktail for efficient delivery into the surrounding areas of the skin wounds. All these siRNA polymer formulations are dissolved in the RNAse free D5W solution.

Administration of the Multi-Targeted siRNA Cocktail in the Skin Wounds

Various formulations are assessed in two different skin wound models, including fixed formulations with three different ratios of three different siRNA duplexes. The three ratios are siRNA duplexes targeting HoxB13, COX-2 and TGF-β1 at 1:1:1, 2:1:1 and 3:1:1 formulated with H3K4b polymer. The study groups are: G1: 20 μg of Control siRNA-HK polymer formulation (50 μL) for each lip surgery wound; G2: 20 μg of HoxB13 siRNA-HK polymer formulation (50 μL) for each lip surgery wound; G3: 20 μg of COX-2 siRNA-HK polymer formulation (50 μL) for each lip surgery wound; G4: 20 μg of TGF-β1 siRNA-HK polymer formulation (50 μL) for each lip surgery wound; G5: 20 μg of ratio one cocktail siRNA-HK polymer formulation (50 μL) for each lip surgery wound; G6: 20 μg of ratio two siRNA-HK polymer formulation (50 μL) for each lip surgery wound; and G7: 20 μg of ratio three siRNA-HK polymer formulation (50 μL) for each lip surgery wound. Four animals are in each group. The same administration is available to both HoxB13 KO and WT mouse. The outcome of this study is to demonstrate the synergistic benefit of the cocktail siRNA formulations comparing to the single siRNA formulation.

The Impacts of Different Formulations on Wound Healing

Three formulations are tested with the siRNA cocktail, using the mouse lip surgery model of HoxB13 WT mouse using a single ratio of siRNA combination such as 1:1:1. The experiment includes G1: 20 μg of control siRNA-HK polymer formulation (50 μL); G2: 20 μg of control siRNA-Pegylated PEI polymer formulation (50 μL); G3: 20 μg of control siRNA-PAMAM dendritic polymer formulation (50 μL); G4: 20 μg of cocktail siRNA-HK polymer formulation (50 μL); G5: 20 μg of cocktail siRNA-pegylated PEI polymer formulation (50 μL), and G6: 20 μg of cocktail siRNA-PAMAM dendritic polymer formulation (50 μL). Each group has four animals. The mRNA and protein level analyses are followed as other in vivo studies. The results provide an optimal formulation of the multi-targeted siRNA cocktail for a clinically viable protocol.

Target Gene Knockdown in vivo at both mRNA and Protein Levels

Skin samples are excised from both HoxB13 KO and WT mouse, either the back skin wound or lip surgery wounds, and immersed in high-glucose DMEM containing 10% FBS and antibiotics/fungizone, surface sterilized in 70% ethanol, dissected into -'5-mm$^2$ sections, and digested in dispase in DMEM (5 mg/ml) overnight at 4° C. Total RNA samples from tissue and cells are reverse transcribed using the RETROscript kit and protocol (Ambion). For antibody staining, paraformaldehyde-fixed adult WT and HoxB13 KO skin samples should be processed, embedded in paraffin, sectioned (6 μm), and baked overnight at 55°. The similar method of RNA isolation and sample preparation for immunohistochemistry can be used for COX-2 and TGF-β1 detections in vivo. The judgment of the most potent siRNA cocktail formulation should be made in consideration of the skin wound model, the genotype of HoxB13 and the ratio of each siRNA duplex. The same principle should be considered that mRNA level knockdown is the key indication of the potency of the multi-target siRNA cocktail.

The Potential Therapeutic Benefits of the Multi-Targeted siRNA Cocktail

To have an initial evaluation of the potential therapeutic benefits of the siRNA cocktail, we are going to carry out two analyses: Histological and HA analysis. Paraformaldehyde-fixed skin samples are processed, embedded in paraffin, and sectioned (6 μm). Slides should be baked overnight at 55° C. and stained with hematoxylin and eosin or Masson's trichrome for collagen, using standard protocols. For HA detection, skin sections are blocked in 2% FBS, incubated with biotinylated HA binding protein (bHABP, 1 μg/ml in PBS; Associates of Cape Cod, Inc., Falmouth, Mass.) overnight at 4° C., rinsed in PBS, incubated with Cy-3-streptavidin (1:500; Jackson Immunoresearch Laboratories) for 30 min at room temperature, rinsed in PBS, and mounted as previously described. As a negative control, tissue should be incubated in PBS alone. Immunofluoresence should be viewed using a Leica DMLB microscope and images captured using an Optronics DEI-750D Digital System. Histology analysis provides graphic information about the morphological difference between the treated and untreated skin wounds and the intensities of presence of the HA protein.

Example 13

Develop a Clinically Viable Protocol for the Multi-Targeted SiRNAs Cocktail A suitable ratio of siRNA duplexes in formulating a cocktail are defined with an optimized polymer formulation, and correlated with a particular mouse model. siRNAs, and cocktails thereof, are tested in the lip surgery model.

The Dose Dependent Curve of the Multi-Targeted siRNA Cocktail Formulation

To define the appropriate dosage of the defined therapeutic candidate siRNA cocktail formulations, 6 different dosages are tested in the mouse lip surgery model. The testing groups are going to be G1: apply 2 µg/50 µL onto the wound; G2: apply 10 µg/50 µL onto the wound; G3: apply 20 µg/50 µL onto the wound; G4: apply 30 µg/50 µL onto the wound, G5: apply 40 µg/50 µL onto the wound and G6: apply 60 µg/50 µL onto the wound. Each group contains four animals. The molecular biological and biochemical readouts should be measured along with the histology and morphology evaluation.

Histological and HA Analysis

Paraformaldehyde-fixed skin samples are processed, embedded in paraffin, and sectioned (6 µm). Slides are baked overnight at 55° C. and stained with hematoxylin and eosin or Masson's trichrome for collagen, using standard protocols. For HA detection, skin sections are blocked in 2% FBS, incubated with biotinylated HA binding protein (bHABP, 1 µg/ml in PBS; Associates of Cape Cod, Inc., Falmouth, Mass.) overnight at 4° C., rinsed in PBS, incubated with Cy-3-streptavidin (1:500; Jackson Immunoresearch Laboratories) for 30 min at room temperature, rinsed in PBS, and mounted as previously described. As a negative control, tissue should be incubated in PBS alone. Immunofluoresence should be viewed using a Leica DMLB microscope and images captured using an Optronics DEI-750D Digital System. The histology analysis provides graphic information about the morphological difference between the treated and untreated skin wounds and the intensities of presence of the HA protein.

Quantification of Collagen Content

Collagen content is determined by measuring hydroxyproline contents of samples. In brief, full-thickness dorsal skin samples (≈16 mg) harvested from 8- to 16-wk-old adult mice (n=6 each for WT and HoxB13 KO) are lyophilized overnight and hydrolyzed in 6 N HCl for 18 h at 110° C. (use enough to cover the tissue), and the pH are then adjusted to between 6 and 7 with NaOH. The samples are diluted to 5 ml with $H_2O$ and filtered using Whatman filter paper. The following solutions are added successively to 1.0 ml of each sample: chloramine T solution (1.0 ml, 0.05 M, room temperature for 20 min), perchloric acid (1.0 ml, 3.15 M, room temperature for 5 min), and 20% p-dimethylaminobenzaldehyde (1.0 ml).

The samples should be incubated at 60° C. for 20 min and cooled to room temperature. Absorbances are going to be read at a wavelength of 557.5 nm, and hydroxyproline concentrations are going to be determined using a standard curve. The following calculation should be used to determine collagen content: µg of hydroxyproline×7.46=µg of collagen. Values are reported as µg/mg dry weight.

Measurement of Tensiometry

For this study, the incisional wound plus surrounding skin is carefully excised and the tissue is fixed in 4% paraformaldehyde overnight. All tissue need to be fixed for the same time, and tensiometry at all time points is conducted the day after wound collection. Before tensiometric analysis, samples should be carefully cut to a uniform length and width, and the thickness of the skin at the wound site is determined. Tensiometry studies are conducted using an Instron testing system. Results should be reported as Y-modulus and the Y-modulus is derived by calculating stress/strain and is representative of the overall wound strength. Stress is the amount of force required to break the wound apart/cross-sectional area of the wound. Strain is the original length of the sample/length at breaking. The raw strain values and cross-sectional areas will not vary significantly at any time point postwounding between WT and HoxB13 KO wounds (data not shown). Thus, the differences in the Y-modulus values are primarily due to the force component of the stress value.

Example 14

Preparing siRNA Inhibitors

The present invention provides a novel approach to prepare siRNA targeting sequences. There are three important aspects that differ from other approaches:

(1) the sequences targeted by siRNA duplexes have homology to both human and mouse sequences of the same gene. That means each of the siRNA duplexes knockdown the same gene target in either human or mouse cells. For example, a potent siRNA specific to HoxB13 gene knocks down both human HoxB13 and mouse HoxB13 gene expression.

(2) the sequences were prepared in three different lengths: 21-mer, 23-mer and 25-mer. Optimal lengths of a given siRNA targeting sequence are identified in various model systems.

(3) the siRNA oligonucleotides are prepared in either blunt end or sticky end form. As used herein, "oligonucleotides" and similar terms based on this relate to short oligonucleotides composed of naturally occurring nucleotides as well as to oligonucleotides composed of synthetic or modified nucleotides. The terms "polynucleotide" and "oligonucleotide" are used synonymously herein.

An oligonucleotide that is an siRNA may have any number of nucleotides between 19 and 30 nucleotides. In a preferred embodiment, an siRNA may have any number of nucleotides between 19 and 27 nucleotides. The siRNA may have two blunt ends, or two sticky ends, or one blunt end with one sticky end. The overhang nucleotides of a sticky end can range from one to four or more.

In a particularly preferred embodiment, the invention provides siRNA of 21, 23 and 25 base pairs with blunt ends.

TABLE 1

Sequences of siRNA duplexes targeting HoxB13, COX-2 and TGF-beta 2 genes in both human and mouse genomes (SEQ ID NOS 66-68, 1, 7, 38, 69-70, 40, 71-74, 3, 9, 75, 46, 76, 48, 77-80, 5, 15 and 81-85, respectively in order of appearance).

| Gene | | No. | Sequence |
|---|---|---|---|
| HoxB13 | | 1 | ggcuccauggagcccggcaauuaug |
| Human | | 2 | ccauggagcccggcaauuaugccac |
| Mouse | | 3 | ggagcccggcaauuaugccaccuug |
| 5' to 3' | | 4 | caaggauaucgaaggcuugcuggga |
| | | 5 | gguggcuggaacagccagauguguu |
| | | 6 | gcuggaacagccagauguguugcca |
| | | 7 | ggacaagaggcgcaagaucucggca |
| | | 8 | gcaagaucucggcagccaccagccu |
| | | 9 | cgccagauuaccaucugguuucaga |
| | | 10 | ccaucugguuucagaaccgccgggu |
| COX-2 | | 1 | gauguuugcauucuuugcccagcac |
| Human | | 2 | caucaguuuuucaagacagaucaua |
| Mouse | | 3 | guuuuucaagacagaucauaagcga |
| 5' to 3' | | 4 | gucuuuggucuggugccuggucuga |
| | | 5 | ggucuggugccuggucugaugaugu |
| | | 6 | gugccuggucugaugauguaugcca |
| | | 7 | gagcaccauucuccuugaaaggacu |
| | | 8 | caccauucuccuugaaaggacuuau |
| | | 9 | ccucaauucagucucucaucugcaa |
| | | 10 | caauucagucucucaucugcaauaa |
| TGF- | | 1 | gcgggcagauccugagcaagcugaa |
| beta | | 2 | ggcagauccugagcaagcugaagcu |
| Human | | 3 | cagauccugagcaagcugaagcuca |
| Mouse | | 4 | ccccggaggugauuuccaucuacaa |
| 5' to 3' | | 5 | ccggaggugauuuccaucuacaaca |
| | | 6 | cuccgaaaaugccaucccgcccacu |
| | | 7 | gaaaaugccaucccgcccacuuucu |
| | | 8 | cgcccacuuucuacagacccuacuu |
| | | 9 | cacuuucuacagacccuacuucaga |
| | | 10 | ccaguggugaucagaaaacuauaaa |

The sequences listed in Tables 2-9 are the target mRNA coding sequences which can be used for siRNA sequences by changing the "t" into "u", such as the sequences listed in Table 1.

TABLE 2

Sequences for Transforming Growth Factor-beta 1 (SEQ ID NOS 86-113, respectively in order of appearance):

| Organism | Gene | homology | Length | No. | Sense Sequences |
|---|---|---|---|---|---|
| Human | TGF-b1 | Human | 21-mer | 1 | ggtcacccgcgtgctaatggt |
| Mouse | | Mouse | | 2 | cacccgcgtgctaatggtgga |
| | | | | 3 | ccaactattgcttcagctcca |
| | | | | 4 | gcggcagctgtacattgactt |
| | | | | 5 | ccacgagcccaagggctacca |
| | | | | 6 | gcccaagggctaccatgccaa |
| | | | | 7 | ccaagggctaccatgccaact |
| | | | | 8 | cgcaagcccaaggtggagcag |
| | | | | 9 | cgctcctgcaagtgcagctga |
| | | | | 10 | caagggctaccatgccaactt |
| | | | 23-mer | 1 | gaggtcacccgcgtgctaatggt |
| | | | | 2 | gtcacccgcgtgctaatggtgga |
| | | | | 3 | gtgcggcagctgtacattgactt |
| | | | | 4 | cgagcccaagggctaccatgcca |
| | | | | 5 | gcccaagggctaccatgccaact |
| | | | | 6 | caagggctaccatgccaacttct |
| | | | | 7 | gtgcgctcctgcaagtgcagctg |
| | | | | 8 | cccaagggctaccatgccaactt |
| | | | | 9 | accaactattgcttcagctccac |
| | | | | 10 | ccgcccggcccgctgcccgaggc |
| | | | 25-mer | 1 | ggatccacgagcccaagggctacca |
| | | | | 2 | gatccacgagcccaagggctaccat |
| | | | | 3 | cacgagcccaagggctaccatgcca |
| | | | | 4 | gagcccaagggctaccatgccaact |
| | | | | 5 | cccaagggctaccatgccaacttct |
| | | | | 6 | gaggtcacccgcgtgctaatggtgg |
| | | | | 7 | gtacaacagcacccgcgaccgggtg |
| | | | | 8 | ggcgccgcctcccccatgccgccct |
| | | | | 9 | |
| | | | | 10 | |

TABLE 3

Sequences for Transforming Growth Factor-beta 2 (SEQ ID NOS 114-115, 60, 116-188, 116 and 119-141, respectively in order of appearance):

| Organism | Gene | homology | Length | No. | Sense Sequences |
|---|---|---|---|---|---|
| Human | TGFb2 | Human | 21-mer | 1 | cgggcagatcctgagcaagct |
| Mouse | | Mouse | | 2 | gcagatcctgagcaagctgaa |

TABLE 3-continued

Sequences for Transforming Growth Factor-beta 2
(SEQ ID NOS 114-115, 60, 116-188, 116 and 119-141,
respectively in order of appearance):

| Organism | Gene | homology | Length | No. | Sense Sequences |
|---|---|---|---|---|---|
| | | | | 3 | gagtactacgccaaggaggtt |
| | | | | 4 | ccatcccgcccactttctaca |
| | | | | 5 | ggcagatcctgagcaagctga |
| | | | | 6 | gatcctgagcaagctgaagct |
| | | | | 7 | ccatcccgcccactttctaca |
| | | | | 8 | ggaggtgatttccatctacaa |
| | | | | 9 | ccgaaaatgccatcccgccca |
| | | | | 10 | cactttctacagaccctactt |
| | | | 23-mer | 1 | cctgagcaagctgaagctcacca |
| | | | | 2 | gagtactacgccaaggaggttta |
| | | | | 3 | ccatcccgcccactttctacaga |
| | | | | 4 | ccgcccactttctacagaccta |
| | | | | 5 | cagatcctgagcaagctgaagct |
| | | | | 6 | ccggaggtgatttccatctacaa |
| | | | | 7 | ctccgaaaatgccatcccgccca |
| | | | | 8 | cactttctacagaccctacttca |
| | | | | 9 | ccagtggtgatcagaaaactata |
| | | | | 10 | ggaagaccccacatctcctgcta |
| | | | 25-mer | 1 | gcgggcagatcctgagcaagctgaa |
| | | | | 2 | ggcagatcctgagcaagctgaagct |
| | | | | 3 | cagatcctgagcaagctgaagctca |
| | | | | 4 | ccccggaggtgatttccatctacaa |
| | | | | 5 | ccggaggtgatttccatctacaaca |
| | | | | 6 | ctccgaaaatgccatcccgcccact |
| | | | | 7 | gaaaatgccatcccgcccactttct |
| | | | | 8 | cgcccactttctacagaccctactt |
| | | | | 9 | cactttctacagaccctacttcaga |
| | | | | 10 | ccagtggtgatcagaaaactataaa |

TABLE 4

Sequences for COX-2 (SEQ ID NOS 142-171,
respectively in order of appearance):

| Organism | Gene | homology | Length | No. | Sense Sequences |
|---|---|---|---|---|---|
| Human Mouse | COX-2 | Human Mouse | 21-mer | 1 | caaaagctgggaagccttctc |
| | | | | 2 | gatgtttgcattctttgccca |
| | | | | 3 | cattctttgcccagcacttca |
| | | | | 4 | catcagttttcaagacagat |
| | | | | 5 | cagttttcaagacagatcat |
| | | | | 6 | gttttcaagacagatcataa |
| | | | | 7 | ctgcgccttttcaaggatgga |
| | | | | 8 | gtctttggtctggtgcctggt |
| | | | | 9 | ctttggtctggtgcctggtct |
| | | | | 10 | ggagcaccattctccttgaaa |
| | | | 23-mer | 1 | gatgtttgcattctttgcccagc |
| | | | | 2 | catcagttttcaagacagatca |
| | | | | 3 | cagttttcaagacagatcataa |
| | | | | 4 | ctgcgccttttcaaggatggaaa |
| | | | | 5 | gtctttggtctggtgcctggtct |
| | | | | 6 | ctttggtctggtgcctggtctga |
| | | | | 7 | ggtctggtgcctggtctgatgat |
| | | | | 8 | ctggtgcctggtctgatgatgta |
| | | | | 9 | gcctggtctgatgatgtatgcca |
| | | | | 10 | gagcaccattctccttgaaagga |
| | | | 25-mer | 1 | gatgtttgcattctttgcccagcac |
| | | | | 2 | catcagttttcaagacagatcata |
| | | | | 3 | gttttcaagacagatcataagcga |
| | | | | 4 | gtctttggtctggtgcctggtctga |
| | | | | 5 | ggtctggtgcctggtctgatgatgt |
| | | | | 6 | gtgcctggtctgatgatgtatgcca |
| | | | | 7 | gagcaccattctccttgaaaggact |
| | | | | 8 | caccattctccttgaaaggacttat |
| | | | | 9 | cctcaattcagtctctcatctgcaa |
| | | | | 10 | caattcagtctctcatctgcaataa |

TABLE 5

Sequences for HoxB13 (SEQ ID NOS 172-189, 187, 186 and 190-199, respectively in order of appearance):

| | | | | | |
|---|---|---|---|---|---|
| Human Mouse | HoxB13 Human Mouse | 21-mer | 1 | ggctccatggagcccggcaat |
| | | | 2 | ccagcctatggccagttacct |
| | | | 3 | ccatggagcccggcaattatg |
| | | | 4 | gcccggcaattatgccacctt |
| | | | 5 | caaggatatcgaaggcttgct |
| | | | 6 | gatatcgaaggcttgctggga |
| | | | 7 | gtggctggaacagccagatgt |
| | | | 8 | gctggaacagccagatgtgtt |
| | | | 9 | gatctcggcagccaccagcct |
| | | | 10 | cgccagattaccatctggttt |
| | | 23-mer | 1 | ggctccatggagcccggcaatta |
| | | | 2 | catggagcccggcaattatgcca |
| | | | 3 | ggagcccggcaattatgccacct |
| | | | 4 | gtggctggaacagccagatgtgt |
| | | | 5 | cgccagattaccatctggtttca |
| | | | 6 | ccagattaccatctggtttcaga |
| | | | 7 | atctggtttcagaaccgccgggt |
| | | | 8 | aagatctcggcagccaccagcct |
| | | | 9 | ccagattaccatctggtttcaga |
| | | | 10 | cgccagattaccatctggtttca |
| | | 25-mer | 1 | ggctccatggagcccggcaattatg |
| | | | 2 | ccatggagcccggcaattatgccac |
| | | | 3 | ggagcccggcaattatgccaccttg |
| | | | 4 | caaggatatcgaaggcttgctggga |
| | | | 5 | ggtggctggaacagccagatgtgtt |
| | | | 6 | gctggaacagccagatgtgttgcca |
| | | | 7 | ggacaagaggcgcaagatctcggca |
| | | | 8 | gcaagatctcggcagccaccagcct |
| | | | 9 | cgccagattaccatctggtttcaga |
| | | | 10 | ccatctggtttcagaaccgccgggt |

TABLE 6

Sequences for PDGF a (SEQ ID NOS 200-229, respectively in order of appearance):

| Organism | Gene | homology | Length | No. | Sense Sequences |
|---|---|---|---|---|---|
| Human Mouse | PDGF a | Human Mouse | 21-mer | 1 | caccctcctccgggccgcgct |
| | | | | 2 | ctcctccgggccgcgctccct |
| | | | | 3 | gtactgaatttcgccgccaca |
| | | | | 4 | ctgaatttcgccgccacagga |
| | | | | 5 | ggagcgcccgccccgcggcct |
| | | | | 6 | ctgctgctcctcggctgcgga |
| | | | | 7 | gctgctcctcggctgcggata |
| | | | | 8 | gatccacagcatccgggacct |
| | | | | 9 | ccacagcatccgggacctcca |
| | | | | 10 | catccgggacctccagcgact |
| | | | 23-mer | 1 | gccaccctcctccgggccgcgct |
| | | | | 2 | ccctcctccgggccgcgctccct |
| | | | | 3 | gatggtactgaatttcgccgcca |
| | | | | 4 | ctggagcgcccgccccgcggcct |
| | | | | 5 | gcgcccgccccgcggcctcgcct |
| | | | | 6 | gcctcgggacgcgatgaggacct |
| | | | | 7 | ggcttgcctgctgctcctcggct |
| | | | | 8 | gcctgctgctcctcggctgcgga |
| | | | | 9 | cagatccacagcatccgggacct |
| | | | | 10 | gaccaggacggtcatttacgaga |
| | | | 25-mer | 1 | gcgccaccctcctccgggccgcgct |
| | | | | 2 | caccctcctccgggccgcgctccct |
| | | | | 3 | gggatggtactgaatttcgccgcca |
| | | | | 4 | gatggtactgaatttcgccgccaca |
| | | | | 5 | ggtactgaatttcgccgccacagga |
| | | | | 6 | ggctggagcgcccgccccgcggcct |
| | | | | 7 | gagcgcccgccccgcggcctcgcct |
| | | | | 8 | ccagcgcctcgggacgcgatgagga |
| | | | | 9 | gcgcctcgggacgcgatgaggacct |
| | | | | 10 | gcctgctgctcctcggctgcggata |

TABLE 7

Sequences for Lamin B1 (SEQ ID NOS 230-232 and 232-258, respectively in order of appearance):

| Human Mouse | Lamin B1 | Human Mouse | 21-mer | 1 | ggagacggagaacagcgcgct |
|---|---|---|---|---|---|
| | | | | 2 | ggagaacagcgcgctgcagct |
| | | | | 3 | gaacagcgcgctgcagctgca |
| | | | | 4 | gaacagcgcgctgcagctgca |
| | | | | 5 | gaggctgggagatgatcagaa |
| | | | | 6 | ggctgggagatgatcagaaaa |
| | | | | 7 | gagccttactgaggacttgga |
| | | | | 8 | cagttagcagatgaaacttta |
| | | | | 9 | gttagcagatgaaactttact |
| | | | | 10 | caatgggaggctgggagatga |
| | | | 23-mer | 1 | ctggagacggagaacagcgcgct |
| | | | | 2 | gagaacagcgcgctgcagctgca |
| | | | | 3 | gagccttactgaggacttggagt |
| | | | | 4 | gggaggctgggagatgatcagaa |
| | | | | 5 | cagagccttactgaggacttgga |
| | | | | 6 | cgacacggcccgcgagcgcgcca |
| | | | | 7 | cagttagcagatgaaactttact |
| | | | | 8 | gttagcagatgaaactttactta |
| | | | | 9 | ccaatgggaggctgggagatgat |
| | | | | 10 | gaagatgtgaaggttatattgaa |
| | | | 25-mer | 1 | gcctggagacggagaacagcgcgct |
| | | | | 2 | cggagaacagcgcgctgcagctgca |
| | | | | 3 | gagccttactgaggacttggagttt |
| | | | | 4 | gggaggctgggagatgatcagaaaa |
| | | | | 5 | gtcagagccttactgaggacttgga |
| | | | | 6 | gacgacacggcccgcgagcgcgcca |
| | | | | 7 | gacacggcccgcgagcgcgccaagc |
| | | | | 8 | cagttagcagatgaaactttactta |
| | | | | 9 | gatcaaccaatgggaggctgggaga |
| | | | | 10 | ccaatgggaggctgggagatgatca |

TABLE 8

Sequences for VEGF A (SEQ ID NOS 259-287 and 281, respectively in order of appearance):

| Organism | Gene | homology | Length | No. | Sense Sequences |
|---|---|---|---|---|---|
| Human Mouse | VEGFA | Human Mouse | 21-mer | 1 | gtgtgcgcagacagtgctcca |
| | | | | 2 | ccaccatgccaagtggtccca |
| | | | | 3 | cctggtggacatcttccagga |
| | | | | 4 | gcacataggagagatgagctt |
| | | | | 5 | caagatccgcagacgtgtaaa |
| | | | | 6 | ggcgaggcagcttgagttaaa |
| | | | | 7 | cttgagttaaacgaacgtact |
| | | | | 8 | ggaaggagcctccctcagggt |
| | | | | 9 | cactttgggtccggagggcga |
| | | | | 10 | cagtattcttggttaatattt |
| | | | 23-mer | 1 | gcctccgaaaccatgaactttct |
| | | | | 2 | ctccaccatgccaagtggtccca |
| | | | | 3 | cctggtggacatcttccaggagt |
| | | | | 4 | cagcacataggagagatgagctt |
| | | | | 5 | gcttgagttaaacgaacgtactt |
| | | | | 6 | gttaaacgaacgtacttgcagat |
| | | | | 7 | ggaaggagcctccctcagggttt |
| | | | | 8 | ctccctcagggtttcgggaacca |
| | | | | 9 | ctaatgttattggtgtcttcact |
| | | | | 10 | gagaaagtgttttatatacggta |
| | | | 25-mer | 1 | cctccgaaaccatgaactttctgct |
| | | | | 2 | ccaccatgccaagtggtcccaggct |
| | | | | 3 | cctggtggacatcttccaggagta |
| | | | | 4 | gatccgcagacgtgtaaatgttcct |
| | | | | 5 | cgcagacgtgtaaatgttcctgcaa |
| | | | | 6 | gtaaatgttcctgcaaaaacacaga |
| | | | | 7 | cagcttgagttaaacgaacgtactt |
| | | | | 8 | gttaaacgaacgtacttgcagatgt |
| | | | | 9 | ccatgccaagtggtcccaggctgca |
| | | | | 10 | cctggtggacatcttccaggagta |

TABLE 9

Sequences for FGF-2 (SEQ ID NOS 288-311, 310 and 312-316, respectively in order of appearance):

| Organism | Gene | homology | Length | No. | Sense Sequences |
|---|---|---|---|---|---|
| Human | FGF-2 | Human | 21-mer | 1 | cttcaaggaccccaagcggct |
| Mouse | | Mouse | | 2 | ggccacttcaaggaccccaag |
| | | | | 3 | ggcttcttcctgcgcatccat |
| | | | | 4 | caagcagaagagagaggagtt |
| | | | | 5 | cagaagagagaggagttgtgt |
| | | | | 6 | gagaggagttgtgtctatcaa |
| | | | | 7 | gaagagagaggagttgtgtct |
| | | | | 8 | gaatctaataactacaatact |
| | | | | 9 | cagttggtatgtggcactgaa |
| | | | | 10 | cactgaaacgaactgggcagt |
| | | | 23-mer | 1 | cacttcaaggaccccaagcggct |
| | | | | 2 | caagcagaagagagaggagttgt |
| | | | | 3 | gcagaagagagaggagttgtgtt |
| | | | | 4 | cagaagagagaggagttgtgtct |
| | | | | 5 | gaagagagaggagttgtgtctat |
| | | | | 6 | gagagaggagttgtgtctatcaa |
| | | | | 7 | ggaatctaataactacaatactt |
| | | | | 8 | ggtatgtggcactgaaacgaact |
| | | | | 9 | gttggtatgtggcactgaaacga |
| | | | | 10 | gtggcactgaaacgaactgggca |
| | | | 25-mer | 1 | gccacttcaaggaccccaagcggct |
| | | | | 2 | caagcagaagagagaggagttgtgt |
| | | | | 3 | gaagagagaggagttgtgtctatca |
| | | | | 4 | cagaagagagaggagttgtgtctat |
| | | | | 5 | gaagagagaggagttgtgtctatca |
| | | | | 6 | ggaatctaataactacaatacttac |
| | | | | 7 | ctaataactacaatacttaccggtc |
| | | | | 8 | cagttggtatgtggcactgaaacga |
| | | | | 9 | gtggcactgaaacgaactgggcagt |
| | | | | 10 | tcttccaatgtctgctaagagctga |

Example 15

Method for siRNA Cocktail Preparation

This invention provides the therapeutic siRNA cocktail targeting multiple disease controlling genes in the same treatment. This invention provides for RNAi agents, such as siRNA oligonucleotides, that are chemically similar to the same source of supply and the same manufacturing process, and they are comprised of four types of nucleotides with different sequences. The invention provides an siRNA cocktail drug for improvement of scarless wound healing by targeting genes involved in the wound healing process, including TGF-β, COX-2, HoxB13 and others.

In a preferred embodiment, the siRNA cocktail has the following characteristics:

(1) The siRNA cocktail contains at least three siRNA duplexes targeting at least three different genes (not three sequences of the same gene) at a ratio needed for the therapy.

(2) The siRNA cocktails for each combination target the roles of each gene in a background of a system biology network, where these genes are functioning either in the same pathway or in a different one.

TABLE A

The siRNA cocktail targeting HoxB13, COX-2 and TGF-β1 (SEQ ID NOS 1, 3, 5, 1, 9, 15, 1, 46, 83, 40, 9 and 83, respectively in order of appearance).

siRNA Cocktail Combinations (siRNA sequences)

HoxB13
COX-2
TGF-β1                   Human and Mouse homologues

| Cocktail 1 | HoxB13 | 5'-caaggauaucgaaggcuugcuggga-3' |
| | COX-2 | 5'-gucuuuggucuggugccuggucuga-3' |
| | TGF-β1 | 5'-ccccggaggugauuuccaucuacaa-3' |
| Cocktail 2 | HoxB13 | 5'-caaggauaucgaaggcuugcuggga-3' |
| | COX-2 | 5'-ggucuggugccuggucugaugaugu-3' |
| | TGF-β1 | 5'-ccggaggugauuuccaucuacaaca-3' |
| Cocktail 3 | HoxB13 | 5'-caaggauaucgaaggcuugcuggga-3' |
| | COX-2 | 5'-gagcaccauucuccuugaaaggacu-3' |
| | TGF-β1 | 5'-cgcccacuuucuacagacccuacuu-3' |
| Cocktail 4 | HoxB13 | 5'-cgccagauuaccaucugguuucaga-3' |
| | COX-2 | 5'-ggucuggugccuggucugaugaugu-3' |
| | TGF-β1 | 5'-cgcccacuuucuacagacccuacuu-3' |

TABLE B

The second siRNA cocktail targeting HoxB13, COX-2 and VEGFA (SEQ ID NOS 1, 3, 317, 1, 46, 317, 40, 9 and 317, respectively in order of appearance).
siRNA Cocktail Combinations (targeted sequences)

HoxB13
COX-2
VEGFA        Human and Mouse homologues

Cocktail 1   HoxB13   5'-caaggauaucgaaggcuugcuggga-3'
             COX-2    5'-gucuuuggucuggugccuggucuga-3'
             VEGFA    5'-ccaugccaagugguccaggcugca-3'

Cocktail 2   HoxB13   5'-caaggauaucgaaggcuugcuggga-3'
             COX-2    5'-ggucuggugccuggucugaugaugu-3'
             VEGFA    5'-ccaugccaagugguccaggcugca-3'

Cocktail 3   HoxB13   5'-caaggauaucgaaggcuugcuggga-3'
             COX-2    5'-gagcaccauucccuugaaggacu-3'
             VEGFA    5'-ccaugccaagugguccaggcugca-3'

Cocktail 4   HoxB13   5'-cgccagauuaccaucugguuucaga-3'
             COX-2    5'-ggucuggugccuggucugaugaugu-3'
             VEGFA    5'-ccaugccaagugguccaggcugca-3'

TABLE C

An Alternative siRNA cocktail targeting HoxB13, COX-2, TGF-β1 & TGF-β2 (SEQ ID NOS 318-321, 1, 9, 13, 15, 1, 46, 42, 80, 40, 9, 42, and 80, repetively in order of appearance):
siRNA Cocktail Combinations (targeted sequences)

HoxB13
COX-2
TGF-β1
TGF-β2       Human and Mouse homologues

Cocktail 1   HoxB13   5'-caaggauaucgaaggcuugcu-3'
             COX-2    5'-gucuuuggucuggugccuggu-3'
             TGF-β1   5'-cacgagcccaagggcuaccau-3'
             TGF-β2   5'-ggaggugauuuccaucuacaa-3'

Cocktail 2   HoxB13   5'-caaggauaucgaaggcuugcuggga-3'
             COX-2    5'-ggucuggugccuggucugaugaugu-3'
             TGF-β1   5'-cacgagcccaagggcuaccaugcca-3'
             TGF-β2   5'-ccggaggugauuuccaucuacaaca-3'

Cocktail 3   HoxB13   5'-caaggauaucgaaggcuugcuggga-3'
             COX-2    5'-gagcaccauucccuugaaggacu-3'
             TGF-β1   5'-ggauccacgagcccaagggcuacca-3'
             TGF-β2   5'-cagauccugagcaagcugaagcuca-3'

Cocktail 4   HoxB13   5'-cgccagauuaccaucugguuucaga-3'
             COX-2    5'-ggucuggugccuggucugaugaugu-3'
             TGF-β1   5'-ggauccacgagcccaagggcuacca-3'
             TGF-β2   5'-cagauccugagcaagcugaagcuca-3'

TABLE D

An Alternative siRNA cocktail targeting HoxB13, TGF-β1 &TGF-β2 (SEQ ID NOS 318, 320, 119, 1, 13, 136, 1, 42, 134, 40, 42 and 134, respectively in order of appearance):
siRNA Cocktail Combinations (targeted sequences)

HoxB13
TGF-β1
TGF-β2       Human and Mouse homologues

Cocktail 1   HoxB13   5'-caaggauaucgaaggcuugcu-3'
             TGF-β1   5'-cacgagcccaagggcuaccau-3'
             TGF-β2   5'-ggaggtgatttccatctacaa-3'

TABLE D-continued

An Alternative siRNA cocktail targeting HoxB13, TGF-β1 &TGF-β2 (SEQ ID NOS 318, 320, 119, 1, 13, 136, 1, 42, 134, 40, 42 and 134, respectively in order of appearance):
siRNA Cocktail Combinations (targeted sequences)

HoxB13
TGF-β1
TGF-β2       Human and Mouse homologues

Cocktail 2   HoxB13   5'-caaggauaucgaaggcuugcuggga-3'
             TGF-β1   5'-cacgagcccaagggcuaccaugcca-3'
             TGF-β2   5'-ccggaggtgatttccatctacaaca-3'

Cocktail 3   HoxB13   5'-caaggauaucgaaggcuugcuggga-3'
             TGF-β1   5'-ggauccacgagcccaagggcuacca-3'
             TGF-β2   5'-cagatcctgagcaagctgaagctca-3'

Cocktail 4   HoxB13   5'-cgccagauuaccaucugguuucaga-3'
             TGF-β1   5'-ggauccacgagcccaagggcuacca-3'
             TGF-β2   5'-cagatcctgagcaagctgaagctca-3'

TABLE E

An Alternative siRNA cocktail targeting HoxB13, COX-2 and TGF-β1 (SEQ ID NOS 318, 322, 320, 1, 9, 42, 1, 46, 42, 40, 9 and 42, respectively in order of appearance):
siRNA Cocktail Combinations (siRNA sequences)

HoxB13
COX-2
TGF-β1       Human and Mouse homologues

Cocktail 1   HoxB13   5'-caaggauaucgaaggcuugcu-3'
             COX-2    5'-gucuuuggucuggugccuggucu-3'
             TGF-β1   5'-cacgagcccaagggcuaccau-3'

Cocktail 2   HoxB13   5'-caaggauaucgaaggcuugcuggga-3'
             COX-2    5'-ggucuggugccuggucugaugaugu-3'
             TGF-β1   5'-ggauccacgagcccaagggcuacca-3'

Cocktail 3   HoxB13   5'-caaggauaucgaaggcuugcuggga-3'
             COX-2    5'-gagcaccauucccuugaaggacu-3'
             TGF-β1   5'-ggauccacgagcccaagggcuacca-3'

Cocktail 4   HoxB13   5'-cgccagauuaccaucugguuucaga-3'
             COX-2    5'-ggucuggugccuggucugaugaugu-3'
             TGF-β1   5'-ggauccacgagcccaagggcuacca-3'

TABLE F

An Alternative siRNA cocktail targeting HoxB13, COX-2, TGF-β1 and PDGFa (SEQ ID NOS 318, 322, 320, 202, 1, 9, 42, 1, 46, 42, 323, 40, 9, 42 and 323, respectively in order of appearance):
siRNA Cocktail Combinations (siRNA sequences)

HoxB13
COX-2
TGF-β1
PDGFa        Human and Mouse homologues

Cocktail 1   HoxB13   5'-caaggauaucgaaggcuugcu-3'
             COX-2    5'-gucuuuggucuggugccuggucu-3'
             TGF-β1   5'-cacgagcccaagggcuaccau-3'
             PDGF a   5'-gtactgaatttcgccgccaca-3'

Cocktail 2   HoxB13   5'-caaggauaucgaaggcuugcuggga-3'
             COX-2    5'-ggucuggugccuggucugaugaugu-3'
             TGF-β1   5'-ggauccacgagcccaagggcuacca-3'
             PDGF a   5'-gggaugguacugaauuucgccgcca-3'

Cocktail 3   HoxB13   5'-caaggauaucgaaggcuugcuggga-3'
             COX-2    5'-gagcaccauucccuugaaggacu-3'

TABLE F-continued

An Alternative siRNA cocktail targeting HoxB13, COX-2, TGF-β1 and PDGFa (SEQ ID NOS 318, 322, 320, 202, 1, 9, 42, 321, 1, 46, 42, 323, 40, 9, 42 and 323, respectively in order of appearance):
siRNA Cocktail Combinations (siRNA sequences)

HoxB13
COX-2
TGF-β1
PDGFa                      Human and Mouse homologues

|  |  |  |
|---|---|---|
|  | TGF-β1 | 5'-ggauccacgagcccaagggcuacca-3' |
|  | PDGF a | 5'-gggaugguacugaauuucgccgcca-3' |
| Cocktail 4 | HoxB13 | 5'-cgccagauuaccaucugguuucaga-3' |
|  | COX-2 | 5'-ggucuggugccuggucugaugaugu-3' |
|  | TGF-β1 | 5'-ggauccacgagcccaagggcuacca-3' |
|  | PDGF a | 5'-gggaugguacugaauuucgccgcca-3' |

TABLE G

An Alternative siRNA cocktail targeting HoxB13, COX-2, TGF-β1 and Lamin (SEQ ID NOS 318, 322, 320, 324, 1, 9, 42, 324, 1, 46, 42, 325, 40, 9, 42 and 325, respectively in order of appearance):
siRNA Cocktail Combinations (siRNA sequences)

HoxB13
COX-2
TGF-β1
Lamin                      Human and Mouse homologues

| Cocktail 1 | HoxB13 | 5'-caaggauaucgaaggcuugcu-3' |
|---|---|---|
|  | COX-2 | 5'-gucuuuggucuggugccuggucu-3' |
|  | TGF-β1 | 5'-cacgagcccaagggcuaccau-3' |
|  | Lamin | 5'-gagccuuacugaggacuuggaguuu-3' |
| Cocktail 2 | HoxB13 | 5'-caaggauaucgaaggcuugcuggga-3' |
|  | COX-2 | 5'-ggucuggugccuggucugaugaugu-3' |
|  | TGF-β1 | 5'-ggauccacgagcccaagggcuacca-3' |
|  | Lamin | 5'-gagccuuacugaggacuuggaguuu-3' |
| Cocktail 3 | HoxB13 | 5'-caaggauaucgaaggcuugcuggga-3' |
|  | COX-2 | 5'-gagcaccauucuccuugaaaggacu-3' |
|  | TGF-β1 | 5'-ggauccacgagcccaagggcuacca-3' |
|  | Lamin | 5'-gucagagccuuacugaggacuugga-3' |
| Cocktail 4 | HoxB13 | 5'-cgccagauuaccaucugguuucaga-3' |
|  | COX-2 | 5'-ggucuggugccuggucugaugaugu-3' |
|  | TGF-β1 | 5'-ggauccacgagcccaagggcuacca-3' |
|  | Lamin | 5'-gucagagccuuacugaggacuugga-3' |

TABLE H

An Alternative siRNA cocktail targeting HoxB13, COX-2 and Lamin (SEQ ID NOS 318, 322, 324, 1, 9, 324, 1, 46, 325, 40, 9 and 325, respectively in order of appearance):
siRNA Cocktail Combinations (siRNA sequences)

HoxB13
COX-2
Lamin                      Human and Mouse homologues

| Cocktail 1 | HoxB13 | 5'-caaggauaucgaaggcuugcu-3' |
|---|---|---|
|  | COX-2 | 5'-gucuuuggucuggugccuggucu-3' |
|  | Lamin | 5'-gagccuuacugaggacuuggaguuu-3' |
| Cocktail 2 | HoxB13 | 5'-caaggauaucgaaggcuugcuggga-3' |
|  | COX-2 | 5'-ggucuggugccuggucugaugaugu-3' |
|  | Lamin | 5'-gagccuuacugaggacuuggaguuu-3' |
| Cocktail 3 | HoxB13 | 5'-caaggauaucgaaggcuugcuggga-3' |
|  | COX-2 | 5'-gagcaccauucuccuugaaaggacu-3' |
|  | Lamin | 5'-gucagagccuuacugaggacuugga-3' |

TABLE H-continued

An Alternative siRNA cocktail targeting HoxB13, COX-2 and Lamin (SEQ ID NOS 318, 322, 324, 1, 9, 324, 1, 46, 325, 40, 9 and 325, respectively in order of appearance):
siRNA Cocktail Combinations (siRNA sequences)

HoxB13
COX-2
Lamin                      Human and Mouse homologues

| Cocktail 4 | HoxB13 | 5'-cgccagauuaccaucugguuucaga-3' |
|---|---|---|
|  | COX-2 | 5'-ggucuggugccuggucugaugaugu-3' |
|  | Lamin | 5'-gucagagccuuacugaggacuugga-3' |

Example 16

Additional siRNA Constructs

Designing siRNA Targeting both Human and Mouse mRNA Sequences

Figure 23:
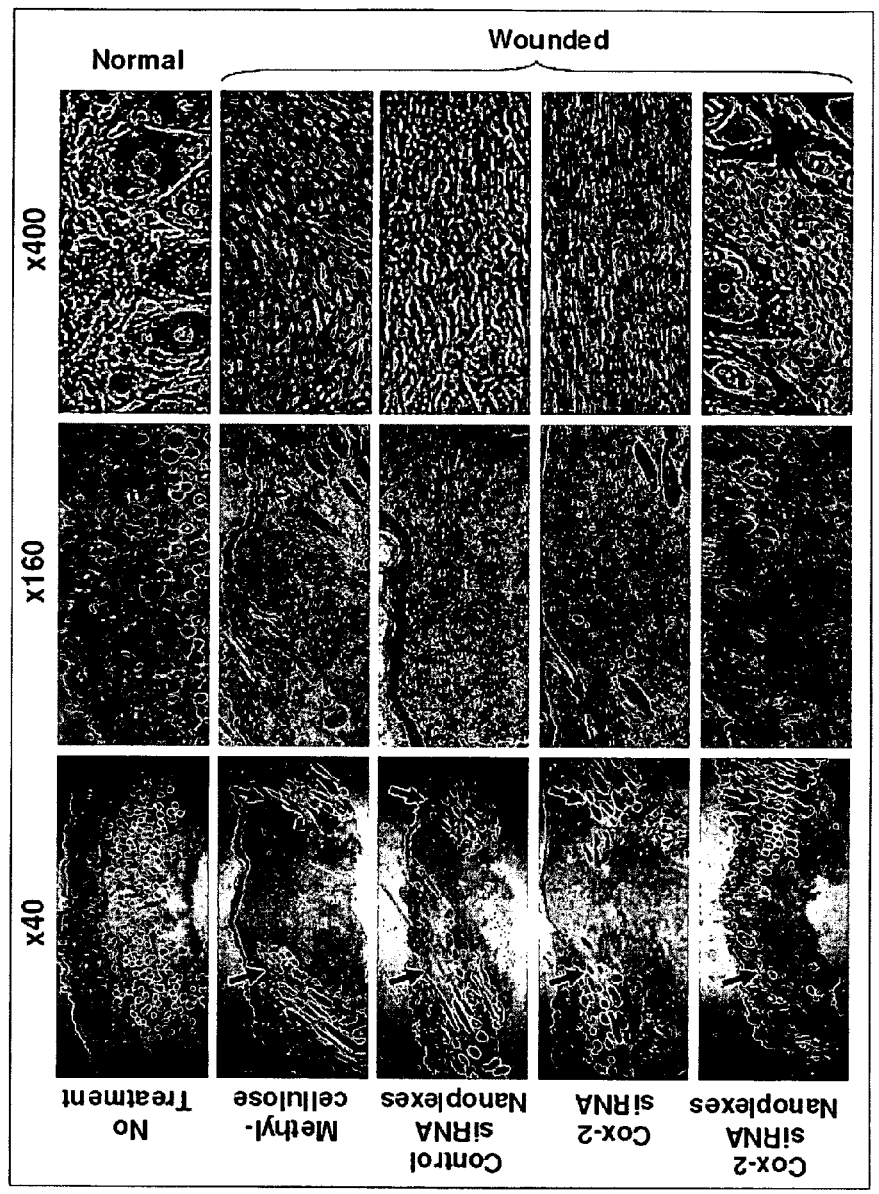
FIG. 23. Nanoparticle/Cox-2 siRNA treatment resulted in similar tissue structures. Neodermis in treated wounds looks more like normal dermis; the collagen has interwoven loose structure. By contrast, the collagen fibers in the neodermis of sham control wounds and control siRNA-nanoplexes treated wounds are placed in an abnormal parallel pattern.

One effort we have put into the siRNA design is that all 25 mer siRNA sequences are able to target the homologues sequences of both human and mouse in the same gene. For example, the siRNA duplex sequence targeting Hoxb13 is able to target both human Hoxb13 and mouse Hoxb13 genes. Sequences have been designed in silico using the general rules for siRNA design and a proprietary algorithm to ensure the following characteristics: (1) optimum thermodynamics, (2) enhance RISC binding, (3) eliminate immune stimulation motifs, (4) human-mouse homology, (5) "off-target" potential blasted and (6) multi-targeted siRNA cocktail. Each sequence is able to target both human and mouse corresponding genes. Therefore, the potent sequences defined from the mouse cell study can be further confirmed using human cells. Potent siRNA Duplexes Targeting TGF-β1, Cox-2, and Hoxb13 mRNA were Identified Among ten in silico designed 25 mer siRNA sequences, we first pick three for testing. Before testing those siRNA oligos (synthesized by Qiagen) in the corresponding cells, such as human PC-3 cell (a bone metastasis of a grade N prostatic adenocarcinoma), we first use RT-PCR to survey the presence of the target gene expression in the total RNA samples (FIG. 14). Interestingly enough, we found substantial expression of human TGF-β1, Cox-2 and Hoxb13 mRNA in the PC-3 cells. We further surveyed the expression of these three genes in the mouse C166 cell. The RT-PCR results again indicated that all three genes are expressed in the C166 cell. Therefore, we can transfect the three selected siRNA oligos targeting a particular gene into the corresponding cell and then evaluate their gene silencing potential, followed by total RNA isolation and RT-PCR analysis. Three doses were used for each transfection on the 6-well plate: 0.5 ug, 1 ug and 2 ug, with Lipo2000 following the vendor's direction. To avoid the over amplification and plateau effects of the RT-PCR, we only run 25-30 cycles of amplification, in order to distinguish silencing activities of each siRNA oligo targeting a particular gene. The RT-PCR products were also subjected to the gel electrophoreses and quantification. FIG. 23 demonstrates the selections of the potent siRNA oligos targeting TGF-β, Cox-2 and Hoxb13 genes. Based on the RT-PCR analyses of total RNA samples isolated from human PC-3 cells and mouse C166 cells, after transfections of these siRNA oligos targeting TGF-β1, Cox-2 and Hoxb13 mRNA sequences, we have selected the following potent 25 mer siRNA duplexes for further evaluation of their potential therapeutic activities for improvement of scarless skin wound healing: (1) hmTF-2: sense, 5'-CCCAAGGGCUACCAUGCCAACUUCU-3' (SEQ ID NO: 11), antisense, 5'-AGAAGUUGGCAUGGUAGCCCU-UGGG-3' (SEQ ID NO: 12); (2) hmCX-1: sense, 5'-GGU-CUGGUGCCUGGUCUGAUGAUGU-3' (SEQ ID NO: 9), antisense, 5'-ACAUCAUCAGACCAGG CACCAGACC-3' (SEQ ID NO: 10); (3) hmHX-1: sense, 5'-GGUGGCUG-GAACAGCCAGAUGUGUU-3' (SEQ ID NO: 7), antisense, 5'-AACACAUCUGGCUGUUCCAGCCACC-3' (SEQ ID NO: 8).

Skin Excision Wound Model for Wound Healing Analysis

Figure 15:
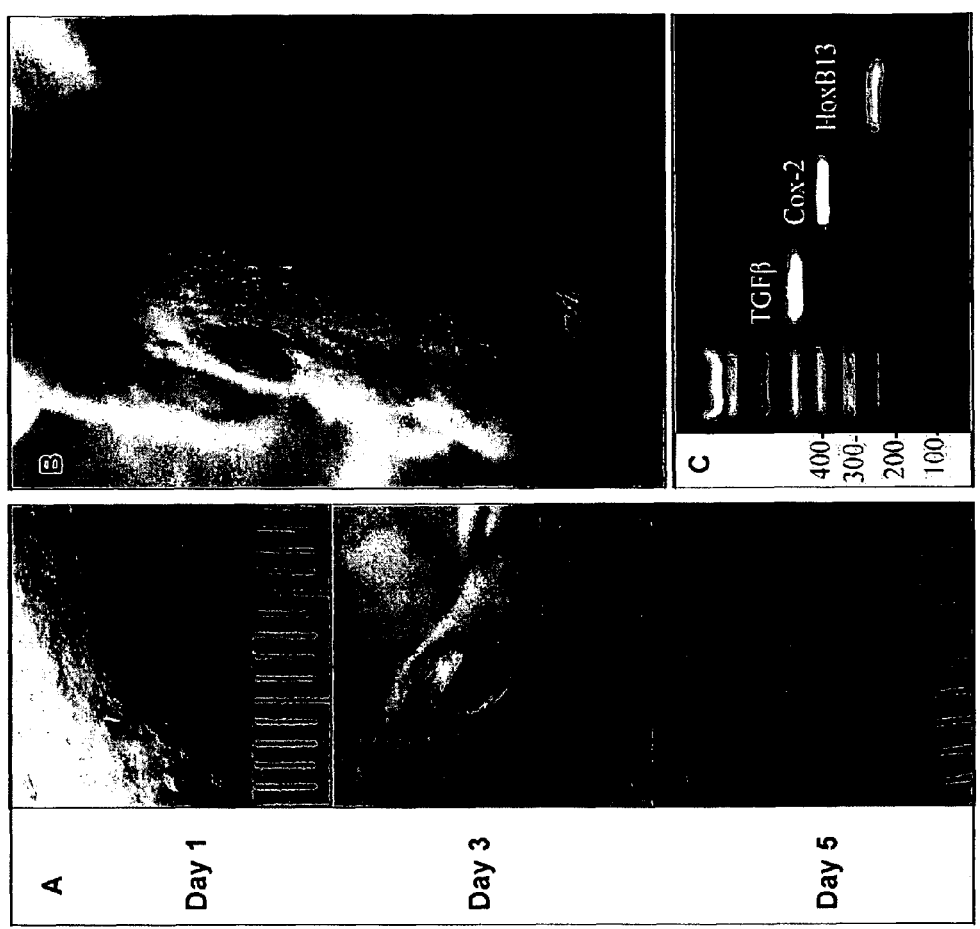
FIG. 15. Mouse skin excisional wound model. A. Comparison of control group and treatment group at Day 1, 3 and 5. B. Observation on Day 5 of a paired 5 mm diameter full-thickness excisional skin wounds created on both sides of the dorsal mid-line of a C57 mouse. C. RT-PCR detection of target gene expression from the total RNA isolated from the mouse skin samples.

A paired 5 mm diameter full-thickness excisional skin wounds were created on both sides of the dorsal midline the depilated dorsum of a mouse (use either C57 mouse or Balb/c mouse, FIG. 15). The control and treated wounds can be observed for wound healing phenotype such as changes of wound closure and target gene knockdown and histopathological changes. In order to evaluate the siRNA-mediated gene expression knockdown in the mouse skin tissue, we use RT-PCR to detect mRNA expressions of TGF-β1, Cox-2 and Hoxb13 in the mouse skin total RNA samples. Total RNA samples were extracted form skin samples according to the manufacture's instructions (RNAqueous-4PCR, Ambion). 0.25 µg of total RNA was incubated at 70° C. for 3 min with oligo (dT) primers and then reverse-transcribed at 42° C. for 30 min in 20 µl reaction mixture containing reverse transcriptase followed by PCR (35 cycles) using specific primers for TGF-β1, Cox-2 and HoxB13 genes. (1) Mouse TGF-β, forward: 5'-CTACTGTGTGCTGAGCACCTT-3' (SEQ ID NO: 62), reverse: 5'-CGCTGCTCGGCCACTCTGGCT-3' (SEQ ID NO: 63), and product: 488 bp; (2) Mouse Cox-2, forward: 5'-GGAAGCCTTCTCCAACCTCT-3' (SEQ ID NO: 58), reverse: 5'-GGATACACCTCTCCACCAAT-3' (SEQ ID NO: 59), product: 371 bp; (3) Mouse HoxB13, forward 5'-CTCCAGCTCCTGTGCCTTAT-3' (SEQ ID NO: 17), reverse: 5'-ACTGGCCATAGGCTGGTATG-3' (SEQ ID NO: 18), product: 205 bp.

Histidine-Lysine Polymer for siRNA Delivery In Vivo

Figure 16:
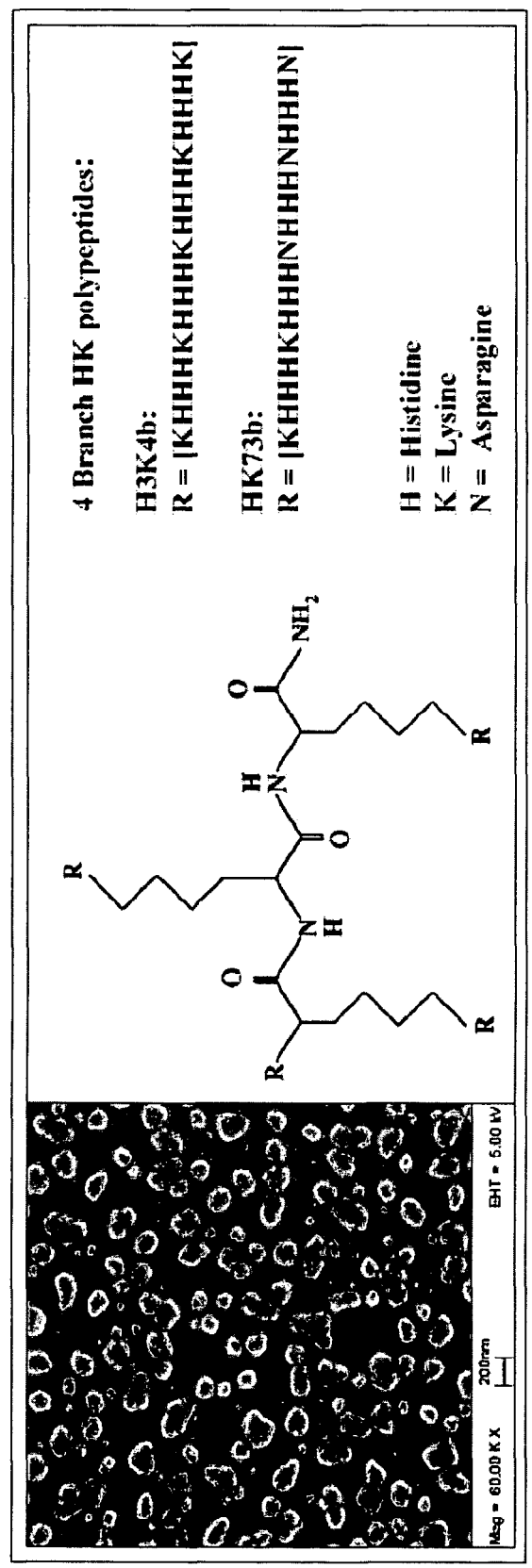
FIG. 16. HK polymer for in vivo siRNA delivery. When HKP mixed with siRNA in the aqueous solution, nanoparticle was formed as seen in the left panel, observed with Scaning Electron Microscope (SEM). Two species of HK polymer have been used for the skin wound siRNA delivery. H3K4b disclosed as SEQ ID NO: 65. HK73b disclosed as SEQ ID NO: 326.
Figure 17:
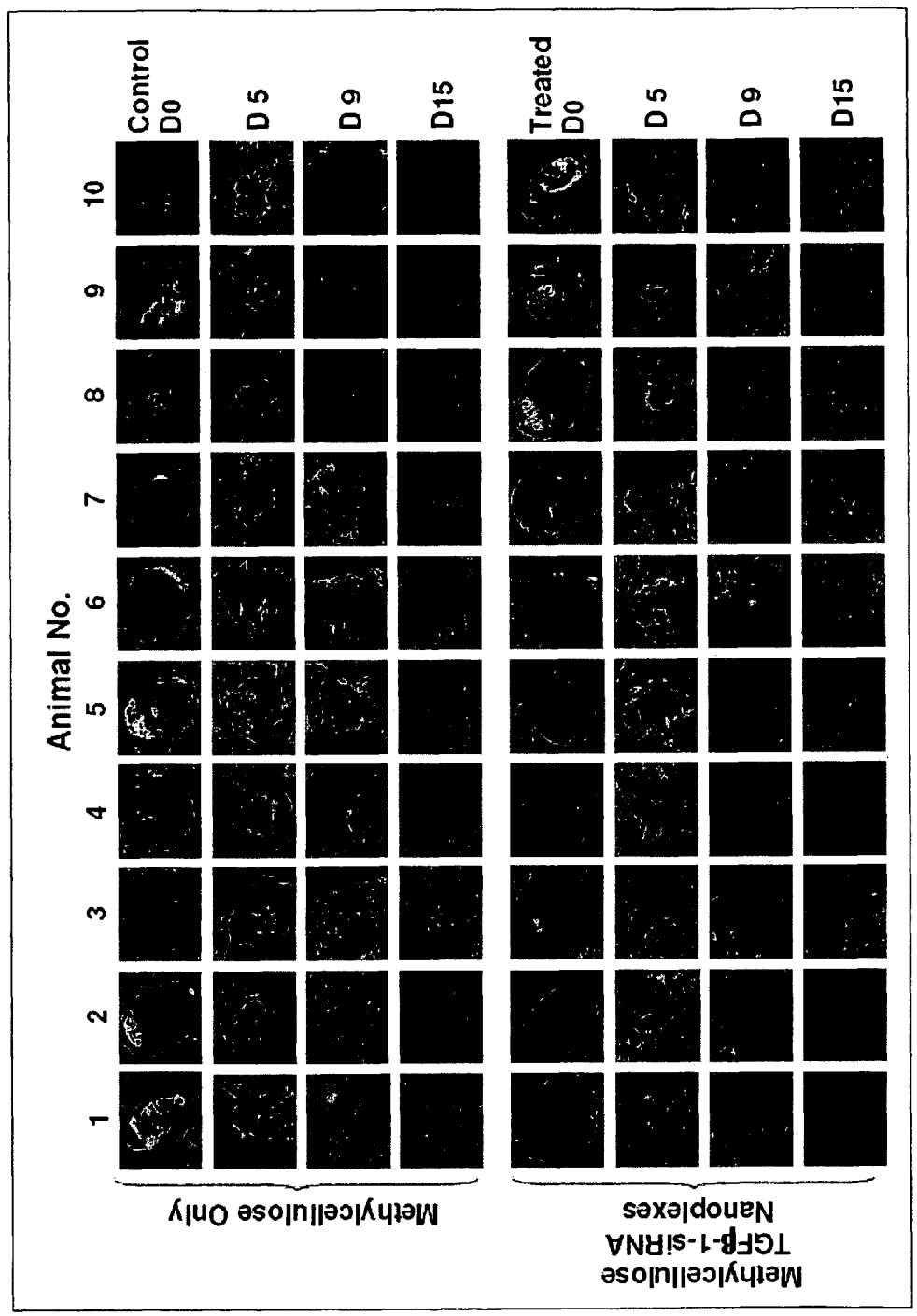
FIG. 17. Animal Skin Model for Wound Healing. Use mouse skin excisional wound model to analyze the therapeutic benefit of the nanoparticle-enhanced topical delivery of TGFβ-1-siRNA. Ten mice were used with two wound on the back skin. The diameter of each wound was measured and the images of each wound were also recorded with photo images.
Figure 18:
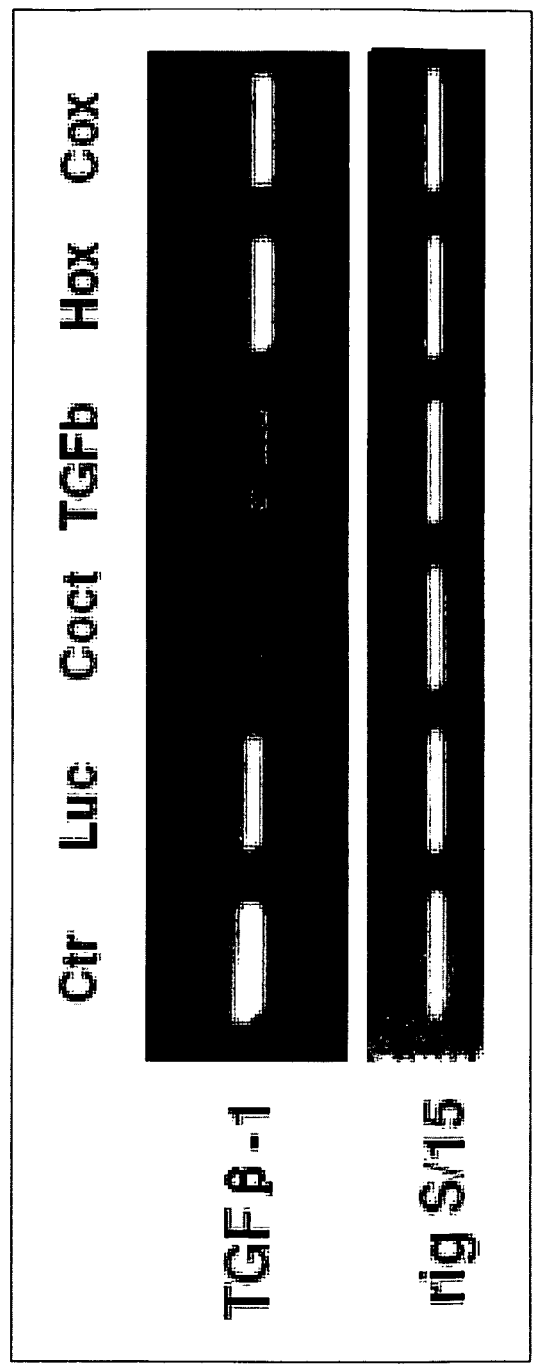
FIG. 18. The therapeutic benefit of nanoparticle-TGFβ-1 siRNA was results of target gene knockdown. The RT-PCR analysis demonstrated the TGFβ-1 specific knockdown with either specific siRNA or cocktail siRNA contains TGFβ-1 specific siRNA. The lower row shows the house keeping gene expression.
Figure 19:
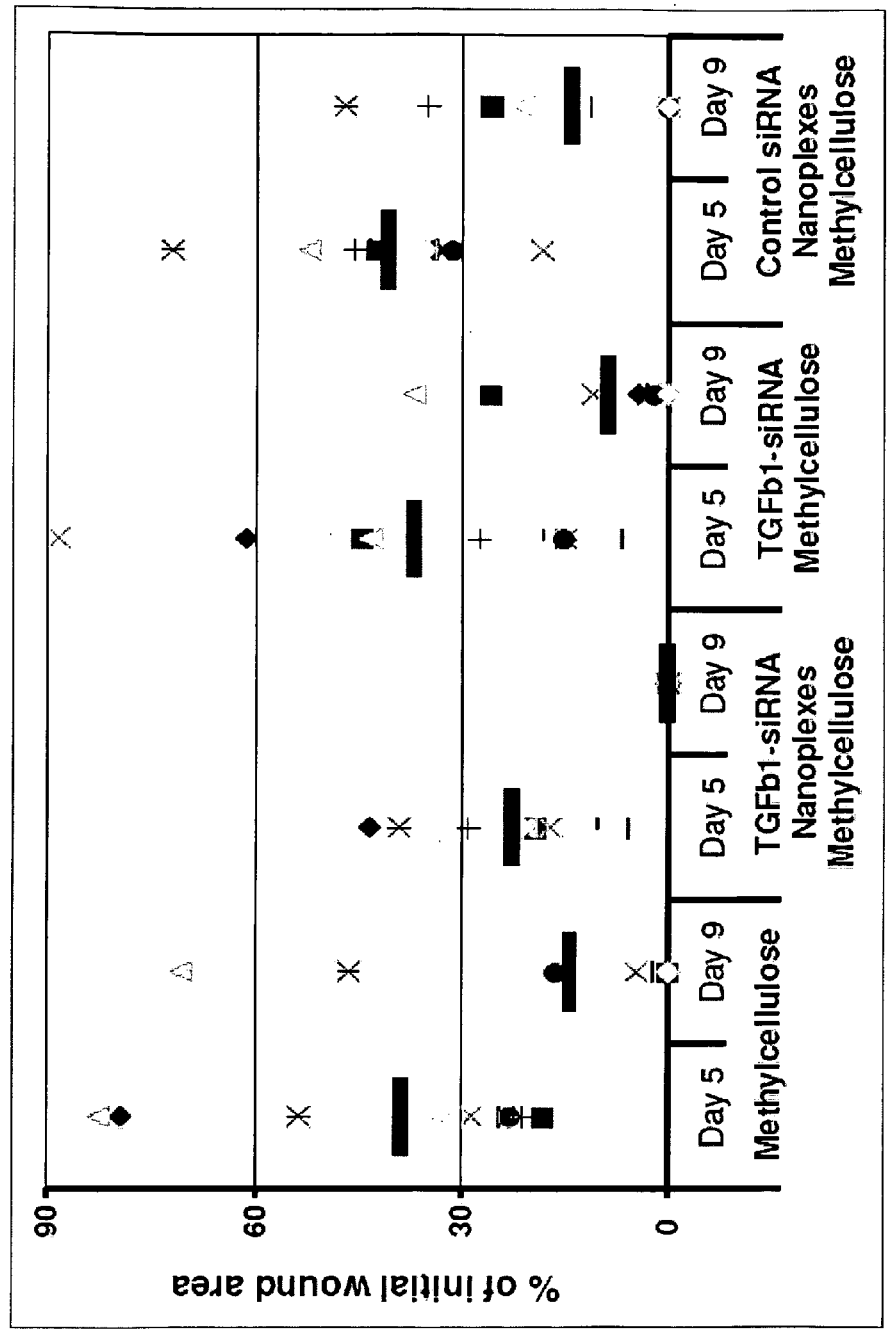
FIG. 19. Nanoparticle-TGFβ-1 siRNA for Wound Healing. Among four groups, group 2 demonstrated smaller wounds on day $5^{th}$ and achieved completed closure on day $9^{th}$. The only active TGFβ-1 siRNA without HK polymer nanoparticle (group 3) showed weaker effect and the control siRNA showed no effect even packaged with HK polymer.
Figure 20:
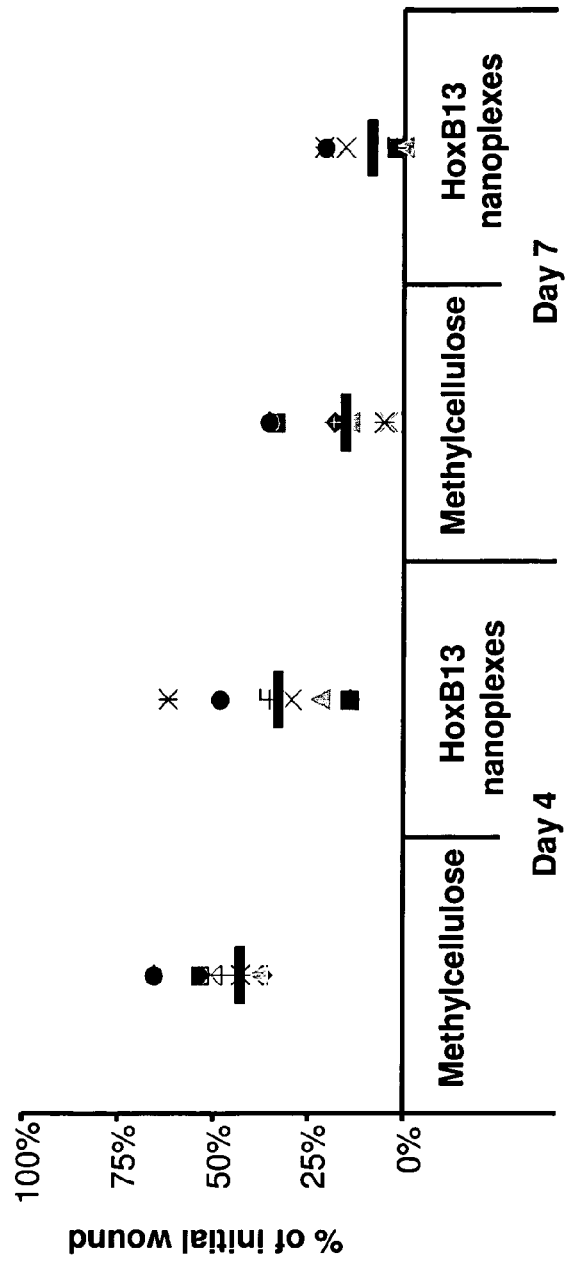
FIG. 20. Similar Effects of the Hoxb13 siRNA on the Wound Closure. Using nanoparticle packaged Hoxb13 siRNA, we can observe the quantified results regarding wound closure at day 4 and day 7. Hoxb13 siRNA packaged with HK polymer had better and faster wound closure.

Optimized histidine-lysine polymers (HKP) have been applied for siRNA deliveries in vitro and in vivo. A pair of the HK polymer species, H3K4b and PT73, has a Lysine backbone with four branches containing multiple repeats of Histidine, Lysine or Asparagine. When this HKP aqueous solution was mixed with siRNA in aqueous solution at a N/P ratio of 4:1 by mass, the nanoparticles (average size of 100-200 nm in diameter) were self-assembled (FIG. 16). Optimal branched histidine-lysine polymer, HKP, was synthesized on a Ranin Voyager synthesizer (PTI, Tucson, Ariz.). The two species of the HKP used in the study were H3K4b and PT73 with a structure of (R)K(R)-K(R)-(R)K(X), for H3K4b where R=KHHHKHHHKHHHKHHHK (SEQ ID NO: 65); and for PT73 where R=KHHHKHHHNHHHNHHHN (SEQ ID NO: 326), X=C(O)NH2, K=lysine, H=histidine and N=Asperagine. The HKP was dissolved in aqueous solution and then mixed with siRNA aqueous solution at a ratio of 4:1 by mass, forming nanoparticles of average size of 150-200 nm in diameter. The HKP-siRNA aqueous solution was semi-transparent without noticeable aggregation of precipitate, and can be stored at 4° C. for at least three months. We applied HKP for skin wound siRNA delivery with Methylcellulose. Using Skin Excisional Wound Model for Wound Healing Analysis The first experiment we did with the skin excisional wound model is to analyze the therapeutic benefit of TGFβ-siRNA with Histidine-Lysine polymer-mediated topical administration. Ten mice were used in the experiment with a paired 5 mm diameter full-thickness excisional skin wounds on both sides of the dorsal midline the depilated dorsum of the Balb/c mouse). The conventional methylcellulose was used as the topical administration carrier with or without nanoparticle/siRNA. Two wounds on each mouse were either treated with only methylcellulose or methylcellulose plus nanoparticle/siRNA daily for the first 5 days. The observations were taken on day 0, 5, 9 and $15^{th}$. When the images were put together (FIG. 17), we found an evident therapeutic benefit on the closure of the skin wounds treated with the nanoparticle-enhanced siRNA delivery. The speed of wound closure at day $5^{th}$ was much faster in treated group than those in the control group. On day $9^{th}$, almost all treated wound were pretty much closed while the control group still had many opened wounds. On day $15^{th}$, the superficial observation showed no significant difference between the two groups.

Quantification of Closures of the Skin Excisional Wound

The second experiment we did was to quantify the wound closure at each time point. At same time, we also asked if the therapeutic benefit is the result of HK polymer or siRNA itself. Four groups of the treatment with 10 samples each were used in the study: 1) Methylcellulose only, 2) Methylcellulose plus nanoparticle/TGFβ-1-siRNA, 3) Methylcellulose plus TGFβ-1-siRNA, and 4) Methylcellulose plus nanoparticle/control-siRNA. By averaging the measurements of the wound samples of each group on day $5^{th}$ and $9^{th}$, we found significant differences (P<0.05) between group 2 and other three groups, even though some effects were seen with group 3. Clearly, The therapeutic benefit for faster skin wound closure is results of nanoparticle-enhanced TGFβ-1-siRNA delivery.

Evidence of Target Gene Knockdown in Samples of the Skin Excisional Wound

Figure 21:
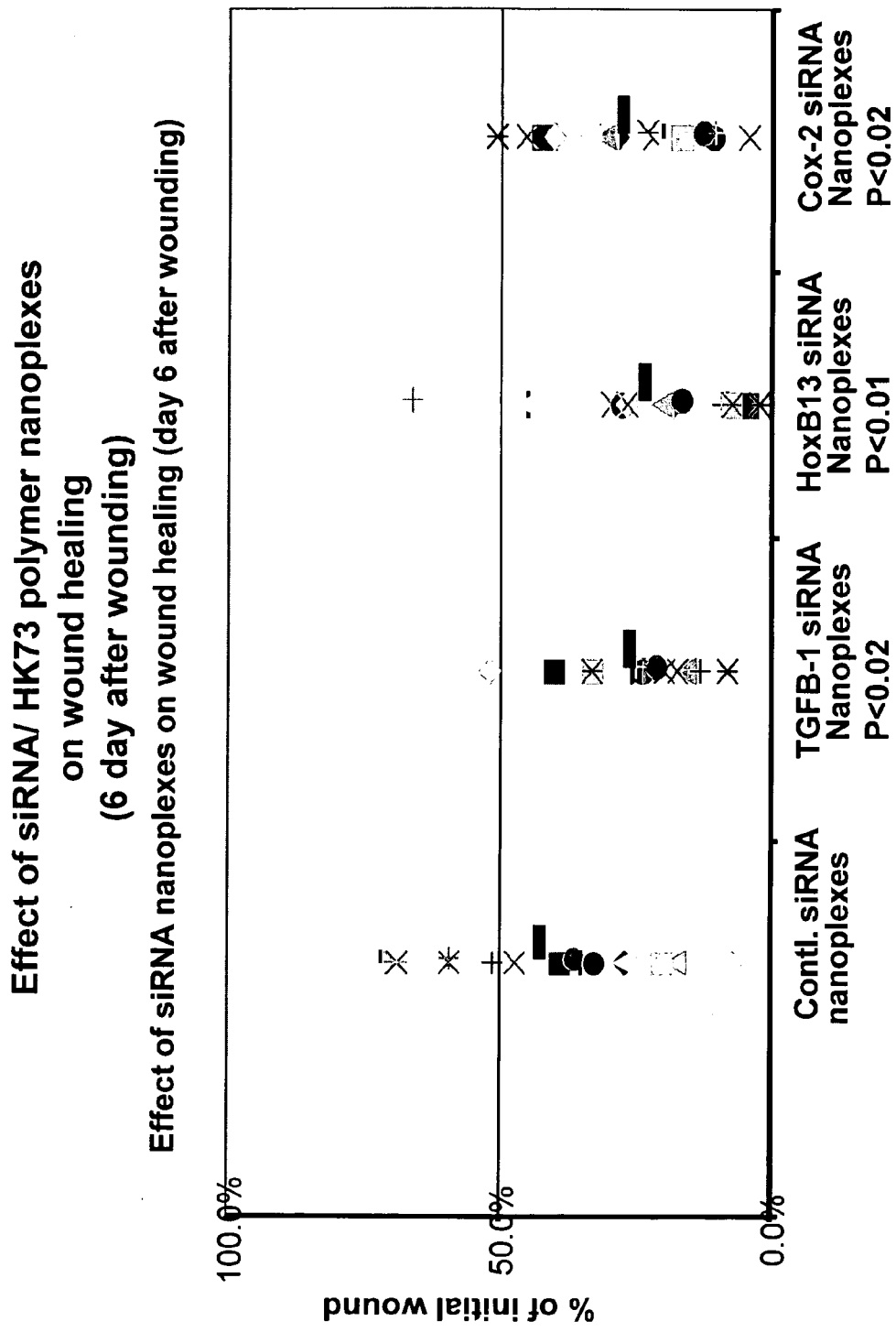
FIG. 21. Nanoparticle for TGFβ-1, Hoxb13 and Cox-2 siRNA delivery The skin delivery of nanoparticle packaged TGFβ-1, Hoxb13 and Cox-2 siRNA duplexes showed better wound healing using mouse skin wound FIG. 22. Collagen organization in WT mouse wound biopsies. Column A: low magnification of (10× or 20×) of WT mouse wound biopsies; Column B: high magnification (100×) of WT mouse wound biopsies; Column C: low magnification (10× or 20×) of Hoxb13 KO mouse wound biopsies; Column D: high magnification (100×) of mouse wound biopsies. Row 1: unwounded skin; row 2: day 20 wound biopsies; row 3: day 30 wound biopsies; row 4: day 60 wound biopsies. Arrows identify India ink location.

As we knew that nanoparticle-enhanced TGFβ-1 was responsible to the therapeutic benefic for the skin wound closure, a key question appears that if the target gene in the surround tissue of the wound was down regulated. For answering such a question, the total RNA was isolated from the representative samples of each group followed by RT-PCR analysis. As shown in FIG. 21, the specific knockdown of TGFβ-1 expression in the wound tissue treated with the nanoparticle-enhanced TGFβ-1 siRNA delivery, compared to the control groups. Interestingly, the siRNA cocktail targeting TGFβ-1, Hoxb13 and Cox-2 packaged with HK polymer demonstrated similar knockdown activity as TGFβ-1 siRNA package with HK polymer, while siRNA duplexes specific to either Hoxb13 or Cox-2 packaged with HK polymer did show TGFβ-1 down regulation.

Histopathology Images of Dermal Tissue Structure during Wound Healing Process

Figure 22:
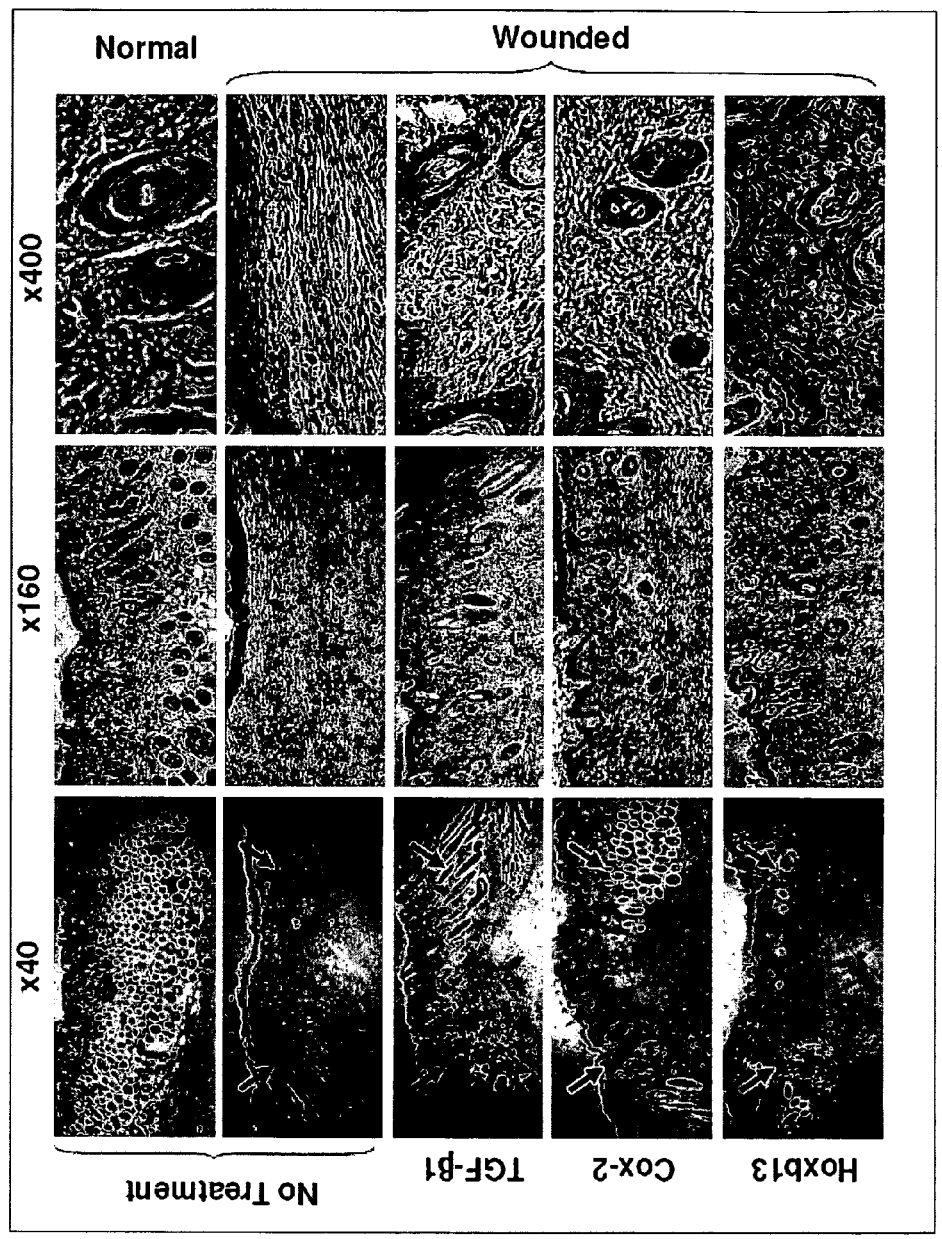

Three different magnifications were used to demonstrate the dermal tissue structure surrounding the wounded area as indicated with arrows. Skin samples were harvested 14 days after wounding, paraformaldehyde-fixed and subjected to Masson's trichrom staining to detect collagenous scar tissue. Restoration of the normal tissue architecture can be seen in wounds treated with TGFβ1 siRNA-, Cox-2 siRNA- and Hoxb13 siRNA—nanoplexes. The architecture of the neodermis of wounds treated with TGFβ1 siRNA-, Cox-2 siRNA-, and Hoxb13 siRNA-nanoplexes resembles that of normal dermis with the reticulate collagen fibers loosely arranged in the basket weave pattern. By contrast, the collagen fibers in the neodermis of sham control wounds and control siRNA-nanoplexes treated wounds are densely placed in an abnormal parallel pattern. These events allow collagen fibers to lie closer together (FIG. 22), facilitating collagen cross-linking and ultimately decreasing scar thickness. Intramolecular and intermolecular collagen cross-links result in increased wound bursting strength.

Nanoparticle-Enhanced Cox-2-siRNA Delivery Resulted in Normal Tissue like Structure As we knew that nanoparticle-enhanced TGFβ-1 was responsible to the therapeutic benefit for the skin wound closure. We also see that siRNA duplexes targeting Cox-2 and Hoxb13 genes were able to enhance the wound closure. At the same time, we want to confirm that the histopathological changes are the result of nanoparticle/siRNA (FIG. 23). The images are showing that nanoparticle/Cox-2 siRNA are the potent contributors resulting similar skin structure as the normal tissue. The tensile strength of a wound is a measurement of its load capacity per unit area. The bursting strength of a wound is the force required to break a wound regardless of its dimension. Bursting strength varies with skin thickness. Peak tensile strength of a wound occurs approximately 60 days after injury. A healed wound only reaches approximately 80% of the tensile strength of unwounded skin.

Antifungal Efficacy of Histidine-Lysine Peptides

Figure 24:
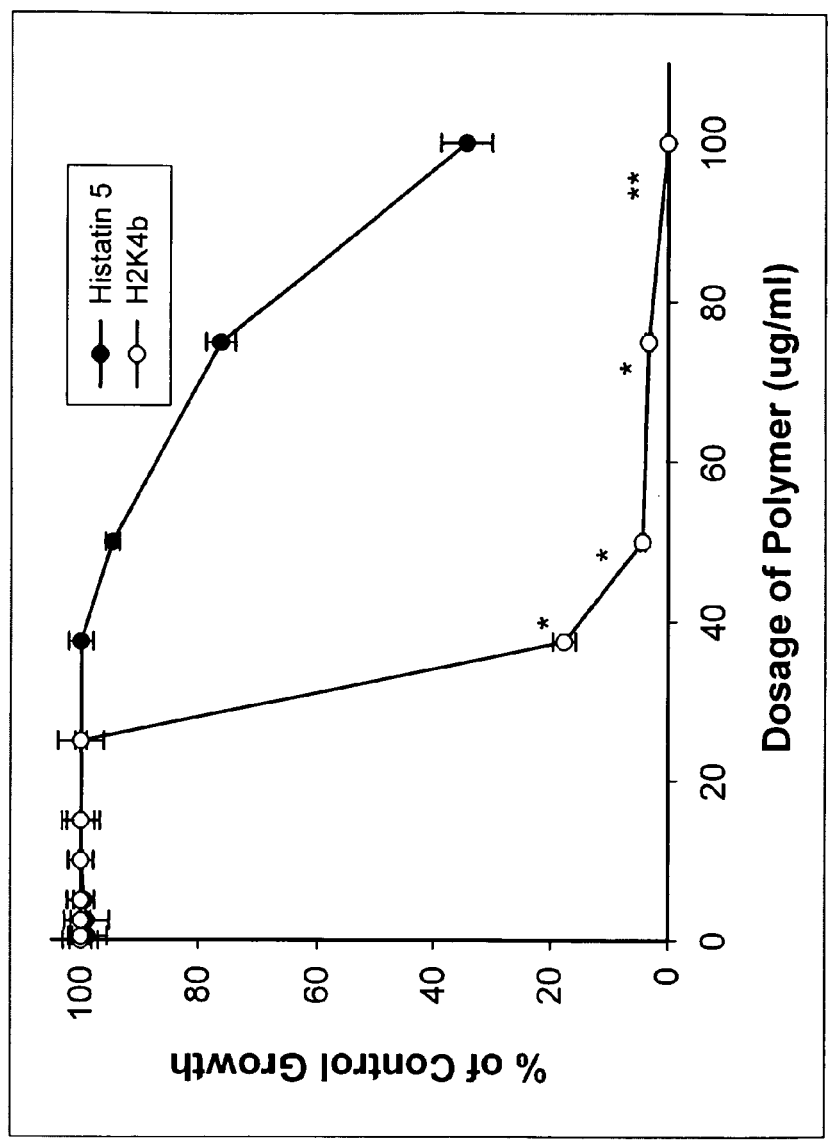
FIG. 24. H2K4b demonstrated potent antifungal activity. Several doses of H2K4b or histatin 5 ranging up to 100 mg/ml were added to YM (yeast-maltose) medium containing C. albicans. The fungi were then rotated at RT for 24 h and growth inhibition by the polymer was determined as indicated in FIG. 2. Experiments were performed in triplicate and the data are represented as means±standard errors. *, P<0.001, **, P<0.01; H2K4b vs. Histatin 5.
Figure 25:
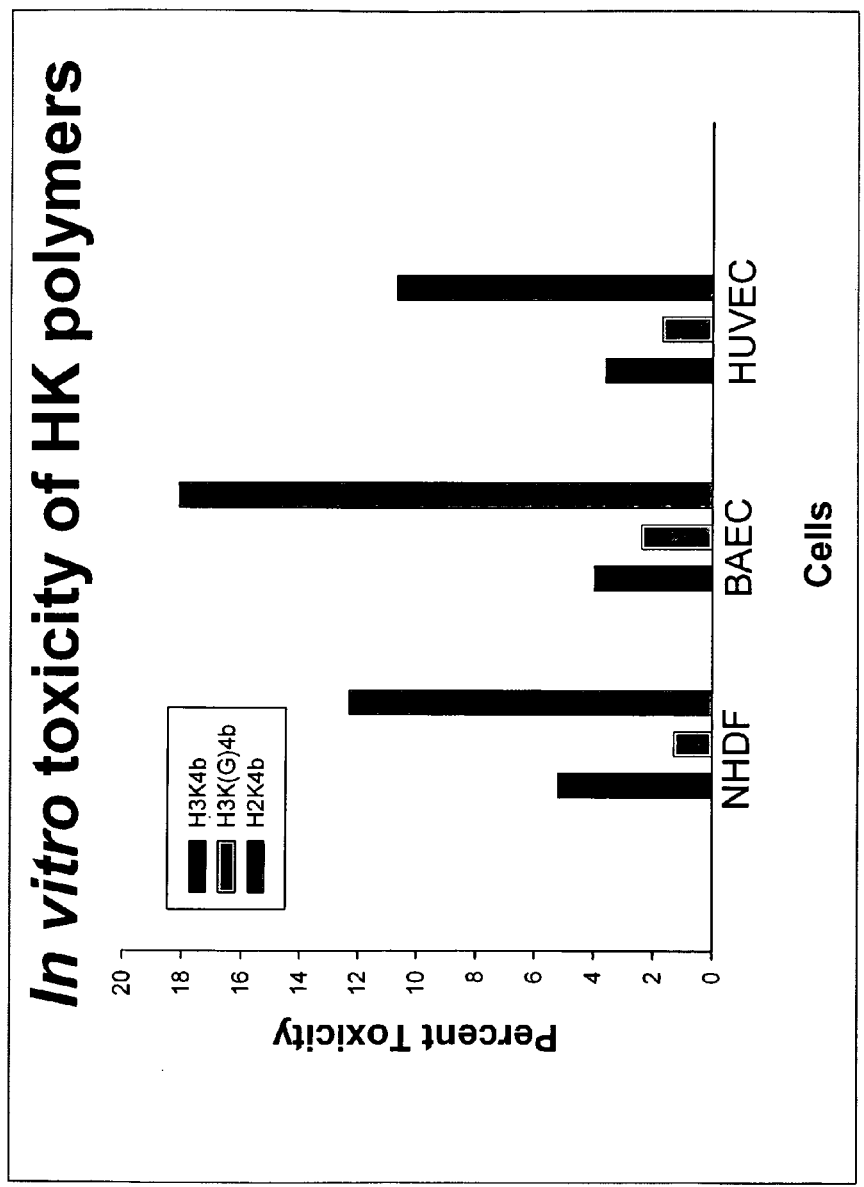
FIG. 25. Cytotoxicity Study of HK polymers. LDH-cytotoxicity assay of BHKP Peptides (H3K4b, H3(G)K4b (PT73), and H2K4b) were added to medium of normal human dermal fibroblasts (NHDF), bovine endothelial cells (BAEC) or human umbilical vasculature endothelial cells (HUVEC). Cytotoxicity was assessed by the LDH-cytotoxicity assay kit. Experimental values represent the average of three experiments.

In our previous studies, it was shown that HK peptides are more effective delivering siRNA into cells than their linear counterparts. To determine whether the branched HK peptides are more effective antifungal agents, HK peptides that varied in their number of branches were studied for inhibition of *C. albicans* growth (FIG. 24). H2K3b reduced growth of *C. albicans* by 11.3% at 37.5 µg/ml (4.5 µM) and by 61.7% at 50 µg/ml (6.0 µM). H2K4b, had the strongest antifungal effect reducing growth of *C. albicans* to nearly 40% at 37.5 µg/ml (3.4 µM) and 85% at 50 µg/ml (4.5 µM). These results show that more highly branched HK peptides were more effective at inhibiting the growth of *C. albicans* than their lesser-branched counterparts. Relative to in vitro toxicity, the in vivo toxicity differences among these peptides are more striking. Preliminary data indicate no acute or subacute toxicity (lung, liver, and kidney) in mice administered H3K(G)4b at does up to 1000 µg (50 mg/kg) intravenously over a 10-second period (FIG. 25). In contrast, preliminary studies indicate that at 1000 µg, H2K4b was toxic to the liver, lung, and kidney 24 h after injection, whereas H3K4b was minimally toxic to the kidney. Of the three organs examined, the kidney appears to be the most sensitive to these peptides. Relative to H2K4b, a decrease in cationic charge in the terminal branches of H3K4b and H3K(G)K4b may, in part, account for their reduced toxicity in vitro and in vivo; the reduction in charge may decrease their interaction with negatively charged cell membranes. With eight additional glycines, H3K(G)4b polymer has a reduced charge per total number of amino acids relative to H3K4b. Because there are five lysines in each terminal arm of H3K(G)4b and H3K4b, however, we doubt that minimal charge differences readily explain the reduced toxicity of H3K(G)4b relative to H3K4b. An alternative possibility is that glycines may disrupt alpha helices in the terminal branches, thereby enhancing the flexibility of the polymer and allowing enzymatic degradation. Several secondary structure programs for peptides predict a marked difference in the alpha helical content between a glycine containing peptide, H3K(G)4b, and the non-glycine containing peptides, H2K4b and H3K4b. Indeed, preliminary data with circular dichroism spectroscopy demonstrate that H3K(G)4b have less alpha helical structure relative to its H3K4b counterpart.

In summary, based on the intensive studies on the siRNA therapeutics for improving skin scarless wound healing with several mouse models, we are very confident that branched Histidine-Lysine peptides is a very potent delivery agent for siRNA in vivo (dermal).

Example 17

Experimental Design for Future Studies

To reach the goals of the proposed study: developing a clinically viable RNAi therapeutic protocol for improvement of adult skin wound healing with less scar tissue formation without decreasing tensile strength and disrupting reepithelialization, we have set three specific aims:
Identify the most Potent siRNA Duplexes for Silencing TGF-β, COX-2 and Hoxb13 Expression in vitro As described in the Table 1, we did design 10 siRNA sequences in silico for each of the targeted genes, Hoxb13, COX-2 and TGF-β1. We then took 3 siRNA duplexes from each of those 10 siRNA sequences and test their potencies for target gene knockdown in the respected cell cultures, human cell PC-3 and mouse cell C166.

Selection of the most Potent siRNA Duplex for each Targeted Gene

To ensure that the most potent siRNA duplex is to be selected for the future therapeutic application, we decided to use those identified siRNA duplexes as a bench mark to further evaluate three additional siRNA duplexes for each of these targeted genes: TGF-β1, Cox-2 and Hoxb13. In terms of the siRNA control sequence, we selected an siRNA duplex targeting a non-related sequence and without any homology to both human and mouse genomes: CT-1: (sense, 5'-GAG-GAGCCUUCAGGAUUACAAGAUU-3' (SEQ ID NO: 50) and antisense, 5'-AAUCUUGUAAUCCUGAAGGCUC-CUC-3' (SEQ ID NO: 51)), which has been validated in several our previous publications (35, 49). The three additional siRNA duplexes targeting both human and mouse Hoxb13 are: hmHX-1: (sense, 5'-CAAGGAUAUCGAAG-GCUUGCUGGGA-3' (SEC) ID NO: 1), antisense, 5'-UC-CCAGCAAGCCUUCGAUAUCCUUG-3' (SEQ ID NO: 2)); hmHX-2: (sense, 5'-GGACAAGAGGCGCAAGAUCUCG-GCA-3' (SEQ ID NO: 69), antisense, 5'-UGCCGAGAUCU-UGCG CCUCUUGUCC-3' (SEQ ID NO: 327)); hmHX-3: (sense, 5'-GCAAGAUCUCGGCAGCCACCAGCCU-3' (SEQ ID NO: 68), antisense, 5'-AGGCUGGUGGCUGC-CGAGAUCUUGC-3' (SEQ ID NO: 328)). The three additional siRNA duplexes targeting both human and mouse Cox-2 are: hmCX-1: (sense, 5'-CAUCAGUUUUUCAAGA-CAGAUCAUA-3' (SEQ ID NO: 73), antisense, 5'-UAUGAUCUGUCUUGAAAAACUGAUG-3' (SEQ ID NO: 329)); hmCX-2: (sense, 5'-GUCUUUGGUCUG-GUGCCUGGUCUGA-3' (SEQ ID NO: 3), antisense, 5'-UCAGACCAGGCACCAGACCAAAGAC-3' (SEQ ID NO: 4)); hmCX-3: (sense, 5'-GUGCCUGGUCU GAUGAUGUAUGCCA-3' (SEQ ID NO: 75), antisense, 5'-UGGCAUACAUCAUCAGACCAGGCAC-3' (SEQ ID NO: 330)). The three additional siRNA duplexes targeting both human and mouse TGF-β1 are: hmTF-1: (sense, 5'-GAUCCACGAGCCCAAGGGCUACCAU-3' (SEQ ID NO: 331), antisense, 5'-AUGGUAGCCCU-UGGGCUCGUGGAUC-3' (SEQ ID NO: 332)); hmTF-2: (sense, 5'-CACGAGCCCAAGGGCUACCAUGCCA-3' (SEQ ID NO: 13), antisense, 5'-UGGCAUGGUAGCCCU-UGGGCUCGUG-3' (SEQ ID NO: 14)); hmTF-3: (sense, 5'-GGCGCCGCCUCCCCCAUGCCGCCCU-3' (SEQ ID NO: 333), antisense, 5'-AGGGCGGC AUGGGGGAGGCG-GCGCC-3' (SEQ ID NO: 64)). A series of transfection experiments are going to be conducted followed by RNA isolation and RT-PCR analyses, to determine if any these additional siRNA duplexes is any better then those already identified.

Transfection of siRNA Duplexes into the Specific Cell Cultures

Since we have found out that human PC-3 cells are very well suited for the siRNA-mediated gene silencing tests for all three gene targets, we will stay with the PC-3 cells for in vitro studies of the gene expression knockdown at both mRNA and protein levels, using three additional siRNA duplexes to compare with the identified siRNA duplexes. Similarly, the mouse C166 cell can also be useful for these siRNA duplexes testing for silencing all three genes. These two cell lines will be cultured on 10-cm plates in DMEM supplemented with 10% fetal bovine serum (FBS), 100 μg/ml streptomycin, and 100 U/ml penicillin and transfected with the siRNA duplexes using Lipofectamin 2000. The cells should be washed twice with PBS and incubated in FBS-free medium for 24 h. FBS-free medium was replaced with medium containing 10% FBS to initiate the cell cycle. The transfection experiments will have reagent control group, non-specific siRNA control group, three different dosages for transfecting the specific siRNA duplexes: 0.5, 1.0 and 2.0 ug per well on 6 well plate. Potential pitfalls: the transfection of those cells with Lipofectamin 2000 may not always work efficiently. Alternative transfection methods can be used, such as electroporation or other transfection agents. The efficient transfection and following RT-PCR analysis may need to work in concert to achieve satisfactory data.

Measurement of mRNA Levels Using RT-PCR

Total RNA from each of those transfected cell lines: PC-3 and C166. For detection of Hoxb13 amplicon (mouse), an RT reaction will be followed with a PCR reaction using forward primer, 5'-CTCCAGCTCCTGTGCCTTAT-3' (SEQ ID NO: 17) and the reverse primer, 5'-ACT GGCCATAGGCTGG-TATG-3' (SEQ ID NO: 18). For detection of Cox-2 amplicon (human), an RT reaction will be followed with a PCR reaction using forward primer, 5'-CGGGCTGGGC-CATGGGGTGGA-3' (SEQ ID NO: 56) and the reverse primer, 5'-CCTATCAGTATTAGCCTGCTT-3' (SEQ ID NO: 57). For detection of TGF-β1 amplicon (mouse), an RT reaction will be followed with a PCR reaction using forward primer, 5'-CTACTGTGTGCTGAGCACCTT-3' (SEQ ID NO: 62) and the reverse primer, 5'-CGCTGCTCGG CCACTCTGGCT-3' (SEQ ID NO: 63). The PCR products should be loaded on a 1% agarose gel and stained with ethidium bromide. The PCR product should exhibit the levels of the knockdown of each particular mRNA using the particular siRNA duplexes. The result from this experiment will determine the potency of each siRNA duplex and provide the first look if a particular siRNA duplex should be the most potent one. The RT-PCR analysis may need to work closely with the transfection experiment so that a proper condition can be optimized for efficient transfection for particular cell line, in order to achieve sufficient amount of total RNA for the PCR analysis. In addition, the selection of the most potent siRNA duplex for each gene will be based on three repeated experiments. The silencing efficacies will be compared between the additional three siRNA duplexes and the previously identified siRNA duplexes.

Measurement of Protein Levels Using ELISA

To measure protein levels of the cells transfected with corresponding siRNA duplexes, the Western blot analysis and ELISA analysis should be sufficient and satisfactory. The cell lysates or cell culture media would be used for the protein detection. Although the ELISA assay for detection of mouse Hoxb13 is not commercially available, we can use the a rat polycolonal antibody to mouse Hoxb13 (Aviva Systems Biologics, San Diego, Calif.) to detect siRNA-mediated knockdown in the Hoxb13 expressing REK cells with a Western blot analysis. Rabbit anti-Hoxb13 antibody was generated against the N-terminal (amino acids 1-7 9) portion of mouse Hoxb13. This antibody should recognize both the WT and knockout Hoxb13 protein. The latter is a truncated protein that stops at amino acid 33 of the homeodomain. Before use, the antisera should be positively affinity purified followed by negative affinity purification against mouse Hoxc13 and chicken Hoxd13 to eliminate possible cross-reactivity with the other Hox13 proteins. Staining should be viewed using a Leica DMLB microscope, and images should be captured using an Optronics DEI750D Digital System (Goleta, Calif.). The human COX-2 will be analyzed using COX-2 ELISA kit (Zymed, San Francisco, Calif.) which is an enzyme-linked immunosorbent sandwich assay for quantitative detection of human COX-2 in cell culture supernatants and cell lysates. Since Cyclooxygenase (COX) is a membrane-bound enzyme, which has a molecular weight of 71 kDa, the cell lysate should be prepared for the ELISA analysis. The mouse TGF-β1 will be analyzed using Human/Mouse TGF-β1 (Transforming Growth Factor beta 1, TGF-β1/TGF-β1) ELISA Ready-SET-Go Kit (with Pre-Coated Plates). The selection of the most potent siRNA duplex for each gene should be based on three repeated experiments.

The potential pitfall is that sometime the most potent siRNA duplex selected from the mRNA knockdown is not correlated with the one selected from the protein knockdown. When that situation happens, we will rely on the data from the mRNA level knockdown, since that it is the direct reflection of RNAi mechanism of action. The discrepancy of the protein level knockdown some time may be due to the non-specific or so call "off-target" effect, which is not the result of the RNAi mechanism of action.

Select the most Efficacious siRNA Cocktail in vivo

After selection of the most potent siRNA duplex for each of the following three genes, Hoxb13, COX-2 and TGF-β1 based on the cell culture studies, we will combine them together as the siRNA cocktail with several ratios. The combinations can be used as 1:1:1, 2:1:1 and 3:1:1, etc. Because of the importance of Hoxb13 in the adult skin wound healing, we will focus on the ratio change of the siRNA duplex specific to Hoxb13. In addition, we will evaluate the appropriate mouse models and siRNA nanoparticle formulations, so that we can define the most suitable siRNA-nanoparticle formulation for potential therapeutic protocol.

The Mouse Model for Evaluation of Multi-Targeted siRNA Cocktails

In order to evaluate the appropriate siRNA cocktail and most suitable formulation, we will obtain the Hoxb13 knockout (KO) adult mouse from Dr. Ling Li's lab, since Hoxb13 KO wounds exhibit several characteristics of early gestational fetal wounds, including faster closure, increased tensile strength, and less dermal scarring when compared with wounds from their wild-type (WT) counterparts. Biochemical evaluation revealed that levels of epidermal and dermal hyaluronic acid (HA) are significantly higher in unwounded adult Hoxb13 KO skin compared with WT skin. Based on these results, we postulate that Hoxb13 in adult skin promotes differentiation, whereas its absence creates a more fetal-like environment, and that one consequence of this fetal-like state is enhanced wound healing. In addition to a well accepted model using the back skin wounds in Hoxb13 KO mice, we have also established a mouse lip surgery model to mimic cleft lip and palate surgery. In our study, under general anesthesia and sterile conditions, Hoxb13 KO and WT adult mice (8-16 week old) will be given a single 0.5 cm full thickness skin incisional wound in parallel with their front teeth followed by suturing (6.0 Nylon) the wound, mimicking the cleft lip and palate surgery.

The Formulations Used for Delivery of the Multi-Targeted siRNA Cocktail

To establish a polymer-siRNA nanoparticle, we decided to first test the Histidine-Lysine branched polymer for this formulation. The biopolymer core facility at the University of Maryland will synthesize polymers on a Ranin Voyager synthesizer (PTI, Tucson, Ariz.). The branched HK polymer, effective for in vivo siRNA transfer, was complexed with siRNA duplexes for local administration. The polymer will be purified by HPLC (Beckman, Fullerton, Calif.). The second branched H (histidine) and K (Lysine) polymers used in this study should be R-KR-KR-KR, where R=[HHHKHHHKH-HHKHHH]2 KH4NH4]. H3K4b is a branched polymer with the same core and structure described above except the R branches differ: R=KHHHKHHHKHHHKHHHK (SEQ ID NO: 65). The HKP can be dissolved in aqueous solution and then mixed with siRNA aqueous solution at a ratio of 4:1 by mass, forming nanoparticles of average size of 150-200 nm in diameter. The HKP-siRNA aqueous solutions were semi-transparent without noticeable aggregation of precipitate, and can be stored at 4° C. for at least three months (50). In addition to HK polymers, we may also test two different types of polymer carriers, pegylated PEI and PAMAM dendrimer, with our siRNA cocktail for efficient delivery into the areas of the skin wounds. All these siRNA polymer formulations will be dissolved in the RNAse free D5W solution and then incorporated into 2% Methylcellulose (1:1) or 2% Methylcellulose:PBS (1:1). The formulation will be applied onto the wound beds and either covered or not with transparent Tegaderm dressing.

Administration of the Multi-Targeted siRNA Cocktail in the Skin Wounds

To test the various formulations in two different skin wound models, we will first test the fixed formulations with three different ratios of three different siRNA duplexes. The three ratios will be siRNA duplexes targeting Hoxb13, Cox-2 and TGF-β1 at 1:1:1, 2:1:1 and 3:1:1 formulated with H3K4b polymer. The study groups are going to be: G1: 20 µg of Control siRNA-HK polymer formulation (50 µL) for each lip surgery wound; G2: 20 µg of Hoxb13 siRNA-HK polymer formulation (50 µL) for each lip surgery wound; G3: 20 µg of Cox-2 siRNA-HK polymer formulation (50 µL) for each lip surgery wound; G4: 20 µg of TGF-β1 siRNA-HK polymer formulation (50 µL) for each lip surgery wound; G5: 20 µg of ratio one cocktail siRNA-HK polymer formulation (50 µL) for each lip surgery wound; G6: 20 µg of ratio two siRNA-HK polymer formulation (50 µL) for each lip surgery wound; and G7: 20 µg of ratio three siRNA-HK polymer formulation (50 µL) for each lip surgery wound. Four animals are in each group. The same administration will be available to both Hoxb13 KO and WT mouse. The outcome of this study is to demonstrate the synergistic benefit of the cocktail siRNA formulations comparing to the single siRNA formulation. The comparison between the results from either KO animal and WT animal will provide an insight how different testing models will response to the novel therapeutic formulations.

The Impacts of Different Formulations on the Wound Healing

Since three formulations are going to be tested with the siRNA cocktail, we plan to only test the three formulations with mouse lip surgery model of Hoxb13 WT mouse. The experiment will focus on one ratio of siRNA combination such as 1:1:1. The experiment will include G1: 20 µg of control siRNA-HK polymer formulation (50 µL); G2: 20 µg of control siRNA-Pegylated PEI polymer formulation (50 µL); G3: 20 µg of control siRNA-PAMAM dendritic polymer formulation (50 µL); G4: 20 µg of cocktail siRNA-HK polymer formulation (50 µL); G5: 20 µg of cocktail siRNA-pegylated PEI polymer formulation (50 µL), and G6: 20 µg of cocktail siRNA-PAMAM dendritic polymer formulation (50 µL). Each group will have four animals. The mRNA and protein level analyses will be followed as other in vivo studies. This study will help us to determine the best formulation of the multi-targeted siRNA cocktail for a clinical protocol.

Target Gene Knockdown in vivo at both mRNA and Protein Levels

Skin samples will be excised from both Hoxb13 KO and WT mouse, either the back skin wound or lip surgery wounds, and immersed in high-glucose DMEM containing 10% FBS and antibiotics/fungizone, surface sterilized in 70% ethanol, dissected into ~5-mm$^2$ sections, and digested in dispase in DMEM (5 mg/ml) overnight at 4° C. Total RNA samples from tissue and cells will be reverse transcribed using the RETROscript kit and protocol (Ambion). For antibody staining, paraformaldehyde-fixed adult WT and Hoxb13 KO skin samples should be processed, embedded in paraffin, sectioned (6 µm), and baked overnight at 55°. The similar method of RNA isolation and sample preparation for immunohistochemistry can be used for Cox-2 and TGF-β1 detections in vivo. The judgment of the most potent siRNA cocktail formulation should be made in consideration of the skin wound model, the genotype of Hoxb13 and the ratio of each siRNA duplex. The same principle should be considered that mRNA level knockdown is the key indication of the potency of the multi-target siRNA cocktail.

The Potential Therapeutic Benefits of the Multi-Targeted siRNA Cocktail

To have an initial evaluation of the potential therapeutic benefits of the siRNA cocktail, we are going to carry out two analyses: Histological and HA analysis. Paraformaldehyde-fixed skin samples will be processed, embedded in paraffin, and sectioned (6 µm). Slides should be baked overnight at 55° C. and stained with hematoxylin and eosin or Masson's trichrome for collagen, using standard protocols. For HA detection, skin sections will be blocked in 2% FBS, incubated with biotinylated HA binding protein (bHABP, 1 µg/ml in PBS; Associates of Cape Cod, Inc., Falmouth, Mass.) overnight at 4° C., rinsed in PBS, incubated with Cy-3-streptavidin (1:500; Jackson Immunoresearch Laboratories) for 30 min at room temperature, rinsed in PBS, and mounted as previously described. As a negative control, tissue should be incubated in PBS alone. Immunofluoresence should be viewed using a Leica DMLB microscope and images captured using an Optronics DEI-750D Digital System. The histology analysis will provide graphic information about the morphological difference between the treated and untreated skin wounds and the intensities of presence of the HA protein.

Develop Clinical Protocol for Multi-Targeted siRNA Cocktail

A proper ratio of siRNA cocktail will be defined with an optimized polymer formulation, and correlated with a particular mouse model. We will design the experiments to test this candidate therapeutic protocol for the pharmacological characteristics and any visible toxicity or adverse effect. In order to present a clear picture, we just assume that the lip surgery model is going to be the one we select at the time (although the real result can only be reached when we complete the first two studies).

The Dose Dependent Curve of the Multi-Targeted siRNA Cocktail Formulation

To define the appropriate dosage of the defined therapeutic candidate siRNA cocktail formulations, we will have 6 different dosage being tested in the mouse lip surgery model. The testing groups are going to be G1: apply 2 μg/50 μL onto the wound; G2: apply 10 μg/50 μL onto the wound; G3: apply 20 μg/50 μL onto the wound; G4: apply 30 μg/50 μL onto the wound, G5: apply 40 μg/50 μL onto the wound and G6: apply 60 μg/50 μL onto the wound. Each group will contain four animals. The molecular biological and biochemical readouts should be measured along with the histology and morphology evaluation.

Histological and HA Analysis

Paraformaldehyde-fixed skin samples will be processed, embedded in paraffin, and sectioned (6 μm). Slides will be baked overnight at 55° C. and stained with hematoxylin and eosin or Masson's trichrome for collagen, using standard protocols. For HA detection, skin sections will be blocked in 2% FBS, incubated with biotinylated HA binding protein (bHABP, 1 μg/ml in PBS; Associates of Cape Cod, Inc., Falmouth, Mass.) overnight at 4° C., rinsed in PBS, incubated with Cy-3-streptavidin (1:500; Jackson Immunoresearch Laboratories) for 30 min at room temperature, rinsed in PBS, and mounted as previously described. As a negative control, tissue should be incubated in PBS alone. Immunofluoresence should be viewed using a Leica DMLB microscope and images captured using an Optronics DEI-750D Digital System. The histology analysis will provide graphic information about the morphological difference between the treated and untreated skin wounds and the intensities of presence of the HA protein.

Quantification of Collagen Content

Collagen content will be determined by measuring hydroxyproline contents of samples. In brief, full-thickness dorsal skin samples (≈16 mg) harvested from 8- to 16-wk-old adult mice (n=6 each for WT and Hoxb13 KO) will be lyophilized overnight and hydrolyzed in 6 N HCl for 18 h at 110° C. (use enough to cover the tissue), and the pH are then adjusted to between 6 and 7 with NaOH. The samples will be diluted to 5 ml with $H_2O$ and filtered using Whatman filter paper. The following solutions will be added successively to 1.0 ml of each sample: chloramine T solution (1.0 ml, 0.05 M, room temperature for 20 min), perchloric acid (1.0 ml, 3.15 M, room temperature for 5 min), and 20% p-dimethylaminobenzaldehyde (1.0 ml). The samples should be incubated at 60° C. for 20 min and cooled to room temperature. Absorbances are going to be read at a wavelength of 557.5 nm, and hydroxyproline concentrations are going to be determined using a standard curve. The following calculation should be used to determine collagen content: μg of hydroxyproline×7.46=μg of collagen. Values are reported as μg/mg dry weight.

Measurement of Tensiometry

For this study, the incisional wound plus surrounding skin will be carefully excised and the tissue will be fixed in 4% paraformaldehyde overnight. All tissue need to be fixed for the same time, and tensiometry at all time points will be conducted the day after wound collection. Before tensiometric analysis, samples should be carefully cut to a uniform length and width, and the thickness of the skin at the wound site will be determined. Tensiometry studies will be conducted using an Instron testing system. Results should be reported as Y-modulus and the Y-modulus is derived by calculating stress/strain and is representative of the overall wound strength. Stress is the amount of force required to break the wound apart/cross-sectional area of the wound. Strain is the original length of the sample/length at breaking. The raw strain values and cross-sectional areas will not vary significantly at any time point postwounding between WT and Hoxb13 KO wounds (data not shown). Thus, the differences in the Y-modulus values are primarily due to the force component of the stress value.

In conclusion, we believe that the abundant data set from the proposed study will provide us substantial information for understanding the characteristics of the multi-targeted siRNA cocktail formulation and therefore, define a clinical protocol for improvement of adult skin wound healing with less scar tissue formation. stronger tensile strength, and faster closure. The multi-targeted siRNA cocktail represents a novel therapeutic approach to treat various skin wounds and will be very valuable for both pharmaceutical and cosmaceutical markets.

REFERENCES

1. Singer A J, Clark R A: Cutaneous wound healing. *N Engl J Med* 1999, 341:738-746.
2. Martin P: Wound healing: aiming for perfect skin regeneration. *Science* 1997, 276:75-81.
3. Rowlatt U: Intrauterine wound healing in a 20 week human fetus. *Virchows Arch A Pathol Anat Histol* 1979, 381:353-361.
4. Lin R Y, et al. Exogenous transforming growth factor-beta amplifies its own expression and induces scar formation in a model of human fetal skin repair. *Ann Surg* 1995, 222:146-154.
5. Cowin A J, et al. Expression of TGF-beta and its receptors in murine fetal and adult dermal wounds. *Eur J Dermatol* 2001, 11:424-431.
6. Krummel T M, et al. Transforming growth factor beta (TGF-beta) induces fibrosis in a fetal wound model. *J Pediatr Surg* 1988, 23:647-652.
7. Lanning D A, et al. TGF-beta1 alters the healing of cutaneous fetal excisional wounds. *J Pediatr Surg* 1999, 34:695-700.
8. Soo C, et al. Ontogenetic transition in fetal wound transforming growth factor-beta regulation correlates with collagen organization. *Am J Pathol* 2003, 163:2459-2476.
9. Sullivan K M, et al. A model of scarless human fetal wound repair is deficient in transforming growth factor beta. *J Pediatr Surg* 1995, 30:198-202202-193.
10. Stelnicki E J, et al. A new in vivo model for the study of fetal wound healing. *Ann Plast Surg* 1997, 39:374-380.
11. Whitby D J and Ferguson M W: Immunohistochemical localization of growth factors in fetal wound healing. *Dev Biol* 1991, 147:207-215.
12. Roberts A B, et al. Transforming growth factor type beta: rapid induction of fibrosis and angiogenesis in vivo and stimulation of collagen formation in vitro. *Proc Natl Acad Sci USA* 1986, 83:4167-4171.
13. Shah M, et al. Neutralising antibody to TGF-beta 1, 2 reduces cutaneous scarring in adult rodents. *J Cell Sci* 1994, 107:1137-1157.
14. Shah M, et al. Control of scarring in adult wounds by neutralising antibody to transforming growth factor beta. *Lancet* 1992, 339:213-214.
15. Choi B M, et al. Control of scarring in adult wounds using antisense transforming growth factor-beta 1 oligodeoxynucleotides. *Immunol Cell Biol* 1996, 74:144-150.
16. Wu K K: Cyclooxygenase 2 induction: molecular mechanism and pathophysiologic roles. *J Lab Clin Med* 1996, 128:242-245.
20. Wilgus T A, et al. Topical application of a selective cyclooxygenase inhibitor suppresses UVB mediated cutaneous inflammation. *Prostaglandins Other Lipid Mediat* 2000, 62:367-384.

21. Sun W H, et al. Cyclooxygenase-2 inhibitors suppress epithelial cell kinetics and delay gastric wound healing in rats. *J Gastroenterol Hepatol* 2000, 15:752-761.
22. Guo J S, et al. Antiangiogenic effect of a highly selective cyclooxygenase-2 inhibitor on gastric ulcer healing in rats. *Toxicol Appl Pharmacol* 2002, 183:41-45.
23. Simon A M, et al. Cyclooxygenase 2 function is essential for bone fracture healing. *J Bone Miner Res* 2002, 17:963-976.
24. Blomme E A, et al. Selective cyclooxygenase-2 inhibition does not affect the healing of cutaneous full-thickness incisional wounds in SKH-1 mice. *Br J Dermatol* 2003, 148:211-223.
25. Muller-Decker K, et al. The effects of cyclooxygenase isozyme inhibition on incisional wound healing in mouse skin. *J Invest Dermatol* 2002, 119:1189-1195.
26. Muscara M N, et al. Wound collagen deposition in rats: effects of an NO-NSAID and a selective COX-2 inhibitor. *Br J Pharmacol* 2000, 129:681-686.
27. Futagami A, et al. Wound healing involves induction of cyclooxygenase-2 expression in rat skin. *Lab Invest* 2002, 82:1503-1513.
28. Wilgus T A, et al. Reduction of scar formation in full-thickness wounds with topical celecoxib treatment. *Wound Repair Regen* 2003, 11:25-34.
29. Mack, J. A. et al. HoxB13 knockout adult skin exhibits high levels of hyaluronan and enhanced wound healing. *FASEB J.* 2003 July; 17(10):1352-4. Epub 2003 May 20.
30. Mack, J. A. et al. HoxB13 up-regulates transglutaminase activity and drives terminal differentiation in an epidermal organotypic model. *J Biol Chem.* 2005 Aug. 19; 280(33):29904-11. Epub 2005 Jun. 17.
31. Stelnicki, E. J. et al. Modulation of the human homeobox genes PRX-2 and HOXB13 in scarless fetal wounds. *J Invest Dermatol.* 1998 July; 111(1):57-63.
32. Wilgus, T. A. et al. Reduction of scar formation in full-thickness wounds with topical celecoxib treatment. *Wound Repair Regen.* 2003 January-February; 11(1):25-34.
33. Manus, M. T. and P. A. Sharp (2002) Gene silencing in mammals by small interfering RNAs. *Nature Review, Genetics.* 3(10):737-747.
34. Lu, P. Y. et al. (2003) siRNA-mediated antitumorigenesis for drug target validation and therapeutics. *Current Opinion in Molecular Therapeutics.* 5(3):225-234.
35. Kim, B. et al. (2004) Inhibition of ocular angiogenesis by siRNA targeting vascular endothelial growth factor-pathway genes; therapeutic strategy for herpetic stromal keratitis. *Am. J Pathol.* 165 (6): 2177-85.
36. Tuschl, Zamore, Lehmann, Bartel and Sharp (1999), *Genes & Dev.* 13: 3191-3197.
37. Elbashir, Lendeckel and Tuschl (2001). *Genes & Dev.* 15: 188-200.
38. Kim, D H, J. J. Rossi et al. Synthetic dsRNA Dicer substrates enhance RNAi potency and efficacy, *Nat Biotechnol.* 2005 February; 23(2):222-6.
39. Reynolds A, et al. Induction of the interferon response by siRNA is cell type- and duplex length-dependent. *RNA.* 2006, 12(6):988-93.
40. Fedorov Y, et al. Off-target effects by siRNA can induce toxic phenotype. *RNA.* 2006, 12(7):1188-96.
41. Lu, P. Y. and M. Woodle (2005) Delivering siRNA in vivo For functional genomics can novel therapeutics. In *RNA Interference Technology.* Cambridge University Press. P 303-317.
42. Lu, P. Y. et al. (2005) Modulation of angiogenesis with siRNA inhibitors for novel therapeutics. *TRENDS in Molecular Medicine.* 11(3), 104-13.
43. Lu P Y, Xie F, Woodle M C. (2005) In vivo application of RNA interference: from functional genomics to therapeutics. *Adv Genet.* 54:117-42.
44. Leng, Q. J. and Mixson A. J. Small interfering RNA targeting Raf-1 inhibits tumor growth in vitro and in vivo. *Cancer Gene Therapy.* (2005), 1-9. See also [http://www.pubmedcentral.nih.gov/articlerender.fcgi?artid=29747; Nucleic Acids Res. 2001 Mar. 15; 29(6): 1334-1340. Copyright© 2001 Oxford University Press Branched co-polymers of histidine and lysine are efficient carriers of plasmids, Qing-Rong Chen, Lei Zhang, Sanford A. Stass, and A. James Mixson]
45. Sutton D. et al. Efficient suppression of secretory clusterin levels by polymer-siRNA nanocomplexes enhances ionizing radiation lethality in human MCF-7 breast cancer cells in vitro. International Journal of Nanomedicine 2006:1(2) 155-162
46. Braun C., et al. Structure/Function Relationships of Polyamidoamine/DNA Dendrimers as Gene Delivery Vehicles, J. of Pharm. Sci., 94(2) (2005).
47. Woodle, M C and P Y Lu, Nanoparticles for RNAi Therapy. *Nanotoday*, August 2005, 34-41.
48. Xie, Y. F., M. Woodle and P Y Lu. Harnessing in vivo siRNA delivery for functional genomics and novel therapeutics. *Drug Discovery Today,* 2006 January; 11(1-2):67-73.
49. Li B. J. et al, Using siRNA in prophylactic and therapeutic regimens against SARS coronavirus in Rhesus macaque. 2005, *Nature Medicine,* 11, 944-951.

All publications, including issued patents and published applications, and database entries identified by accession numbers are incorporated herein by reference in their entirety.

What is claimed is:

1. A composition comprising at least three siRNA molecules and a pharmaceutically acceptable carrier, wherein each siRNA molecule binds an mRNA molecule that is encoded by a gene selected from the group consisting of TGF-β1, Cox-2, and Hoxb13, wherein said molecules inhibit expression of said genes in both human and mouse cells, wherein said composition comprises a nanoparticle, and wherein said siRNA molecules comprise the following oligonucleotides:

(1) hmTF-2: sense, 5'-CCCAAGGGCUACCAUGCCAACUUCU-3'
(SEQ ID NO: 11)
antisense, 5'AGAAGUUGGCAUGGUAGCCCUUGGG-3';
(SEQ ID NO: 12)

(2) hmCX-1: sense, 5'-GGUCUGGUGCCUGGUCUGAUGAUGU-3',
(SEQ ID NO: 9)
antisense, 5'-ACAUCAUCAGACCAGGCACCAGACC-3';
(SEQ ID NO: 10) and (3) hmHX-1: sense, 5'-GGUGGCUGGAACAGCCAGAUGUGUU-3'
(SEQ ID NO: 7)
antisense, 5'-AACACAUCUGGCUGUUCCAGCCACC-3'
(SEQ ID NO: 8).

2. The composition of claim 1, wherein said pharmaceutically acceptable carrier comprises a branched histidine polypeptide or a branched lysine polypeptide.

3. A method for treating a dermal or epidermal wound in a subject, wherein said wound is characterized at least in part by inflammation and neovascularization, said method comprising administering to said subject a pharmaceutically effective amount of the composition of claim 1.

4. The method of claim 3 wherein said subject is a mammal.

5. The method of claim 3 wherein said subject is a human.

6. A composition comprising at least three siRNA molecules, wherein each siRNA molecule binds an mRNA molecule that is encoded by a gene selected from the group consisting of TGF-β1, Cox-2, and Hoxb13, and a pharmaceutically acceptable carrier, wherein said siRNA molecules comprise the following oligonucleotides:

(1) hmTF-2: sense, 5'-CCCAAGGGCUACCAUGCCAACUUCU-3'
(SEQ ID NO: 11)
antisense, 5'AGAAGUUGGCAUGGUAGCCCUUGGG-3';
(SEQ ID NO: 12)

(2) hmCX-1: sense, 5'-GGUCUGGUGCCUGGUCUGAUGAUGU-3',
(SEQ ID NO: 9)
antisense, 5'-ACAUCAUCAGACCAGGCACCAGACC-3';
(SEQ ID NO: 10) and (3) hmHX-1: sense, 5'-GGUGGCUGGAACAGCCAGAUGUGUU-3'
(SEQ ID NO: 7)
antisense, 5'-AACACAUCUGGCUGUUCCAGCCACC-3'
(SEQ ID NO: 8).

7. The composition of claim 1, wherein said pharmaceutically acceptable carrier comprises a branched histidine-lysine peptide.

8. The composition of claim 6, wherein said pharmaceutically acceptable carrier comprises a branched histidine polypeptide or a branched lysine polypeptide.

9. The composition of claim 6, wherein said pharmaceutically acceptable carrier comprises a branched histidine-lysine peptide.

10. The composition of claim 6, wherein said composition comprises a nanoparticle.

11. The composition of claim 8, wherein said composition comprises a nanoparticle.

12. The composition of claim 9, wherein said composition comprises a nanoparticle.

* * * * *